(12) United States Patent
Beard et al.

(10) Patent No.: US 9,974,772 B2
(45) Date of Patent: *May 22, 2018

(54) AMIDE DERIVATIVES OF N-UREA SUBSTITUTED AMINO ACIDS AS FORMYL PEPTIDE RECEPTOR LIKE-1 (FPRL-1) RECEPTOR MODULATORS

(71) Applicant: Allergan, Inc., Irvine, CA (US)

(72) Inventors: Richard L. Beard, Newport Beach, CA (US); Tien T. Duong, Rancho Santa Margarita, CA (US); John E. Donello, Dana Point, CA (US); Veena Viswanath, Irvine, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/408,643

(22) Filed: Jan. 18, 2017

(65) Prior Publication Data

US 2017/0119737 A1  May 4, 2017

Related U.S. Application Data

(60) Continuation of application No. 15/138,823, filed on Apr. 26, 2016, now Pat. No. 9,579,307, which is a continuation of application No. 14/608,503, filed on Jan. 29, 2015, now Pat. No. 9,351,948, which is a continuation of application No. 14/102,145, filed on Dec. 10, 2013, now Pat. No. 8,993,780, which is a division of application No. 13/658,523, filed on Oct. 23, 2012, now Pat. No. 8,658,803.

(60) Provisional application No. 61/551,772, filed on Oct. 26, 2011.

(51) Int. Cl.

| | | |
|---|---|---|
| *A61K 31/417* | (2006.01) |
| *A61K 31/198* | (2006.01) |
| *A61K 31/17* | (2006.01) |
| *A61K 31/4045* | (2006.01) |
| *A61K 31/216* | (2006.01) |
| *A61K 31/197* | (2006.01) |
| *C07C 323/60* | (2006.01) |
| *C07C 317/50* | (2006.01) |
| *C07C 323/44* | (2006.01) |
| *C07C 317/42* | (2006.01) |
| *C07D 233/64* | (2006.01) |
| *C07C 275/30* | (2006.01) |
| *C07D 209/20* | (2006.01) |
| *C07K 5/062* | (2006.01) |
| *C07K 5/078* | (2006.01) |
| *C07K 5/072* | (2006.01) |

(52) U.S. Cl.
CPC ............ *A61K 31/417* (2013.01); *A61K 31/17* (2013.01); *A61K 31/197* (2013.01); *A61K 31/198* (2013.01); *A61K 31/216* (2013.01); *A61K 31/4045* (2013.01); *C07C 275/30* (2013.01); *C07C 317/42* (2013.01); *C07C 317/50* (2013.01); *C07C 323/44* (2013.01); *C07C 323/60* (2013.01); *C07D 209/20* (2013.01); *C07D 233/64* (2013.01); *C07K 5/0606* (2013.01); *C07K 5/06017* (2013.01); *C07K 5/06034* (2013.01); *C07K 5/06052* (2013.01); *C07K 5/06113* (2013.01); *C07K 5/06147* (2013.01); *C07K 5/06156* (2013.01)

(58) Field of Classification Search
CPC combination set(s) only.
See application file for complete search history.

(56) References Cited

U.S. PATENT DOCUMENTS

| | | | |
|---|---|---|---|
| 5,492,896 A | 2/1996 | Habich | |
| 6,423,689 B1 | 7/2002 | Booth ................ | C07K 5/06008 514/15.1 |
| 6,548,637 B1 * | 4/2003 | Persons .............. | C07K 5/06078 530/331 |
| 7,678,913 B2 | 3/2010 | Song et al. | |
| 2004/0266766 A1 * | 12/2004 | Sperl .................. | C07K 5/06069 514/230.5 |
| 2007/0287716 A1 | 12/2007 | Hu et al. | |
| 2008/0188521 A1 | 8/2008 | Grimm et al. | |
| 2014/0213611 A1 | 7/2014 | Evans ................... | C07C 237/22 514/311 |

FOREIGN PATENT DOCUMENTS

| | | |
|---|---|---|
| EP | 0457195 A3 | 11/1991 |
| FR | 2533210 | 12/1984 |
| JP | 6172288 A | 6/1994 |
| WO | 1995012612 A1 | 5/1995 |
| WO | WO 1995012612 A1 | 5/1995 |

(Continued)

OTHER PUBLICATIONS

Moeller et al. "Synthesis and spectroscopic characterization of 4-chlorophenyl isocyanate (1-chloro-4-isocyanatobenzene) adducts with amino acids as potential dosimeters for the biomonitoring of isocyanate exposure." Helv. Chim. Acta 1998, 81, 1254-1263 (Year: 1998).*
Higgins et al. "N-terminus urea-substituted chemotactic peptides: new potent agonists and antagonists toward the neutrophil fMLF receptor." J. Med. Chem. 1996, 39, 1013-1015 (Year: 1996).*
Cross, L.C. et al, Rules for the Nomenclature of Organic Chemistry, Section E: Stereochemistry, Pure & Appl. Chem., 1976, 11-30, 45.
Heinrich Stahl, Pharmaceutical Salts, Handbook of Pharmaceutical Salts, 2002, 329-345, International Union of Pure and Applied Chemistry, Verlag Helvetica Chemica Acta—Zürich.
Higgins, John et al, N-Terminus Urea-Substituted Chemotactic Peptides: New Potent Agonists and Antagonists Toward the Neutrophil fMLF Receptor, Journal of Medicinal Chemistry, Mar. 1, 1996, 1013-1015, 39(5).

(Continued)

*Primary Examiner* — Amanda L Aguirre

(74) *Attorney, Agent, or Firm* — Barbara C. Potts

(57) ABSTRACT

The present invention relates to novel amide derivatives of N-urea substituted amino acids, processes for preparing them, pharmaceutical compositions containing them and their use as pharmaceuticals as modulators of the N-formyl peptide receptor like-1 (FPRL-1) receptor.

6 Claims, No Drawings

(56) References Cited

FOREIGN PATENT DOCUMENTS

| WO | 9965932 | 12/1999 | |
| WO | 2004039765 A1 | 5/2004 | |
| WO | WO 2004039765 A1 | 5/2004 | |
| WO | WO 2004087643 A1 | 10/2004 | ........... C07C 275/28 |
| WO | 2005-047899 | 5/2005 | |
| WO | 2006063113 A2 | 6/2006 | |

OTHER PUBLICATIONS

Perretti, Mauro et al, Therapeutic Anti-Inflammatory Potential of Formyl-Peptide Receptor Agonists, Pharmacology & Research, 2010, 175-188, 127.

Marianne Moller et al.; Synthesis and Spectroscopic Characterization of 4-Chlorophenylisocyanate ( = 1-Chloro-4-isocyanatobenzene) Adducts with Amino Acids as Potential Dosimeters for the Biomonitoring of Isocyanate Exposure; Helvetica Chimica Acta—vol. 81 (1998); pp. 1254-1283.

Dianqing Sun et al.; Solid-Phase Synthesis of a Thymidinyl Dipeptide Urea Library; J. Comb. Chem. 2007, 9, pp. 370-385; Department of Pharmaceutical Sciences, University of Tennessee Health Science Center, Memphis, Tennessee 38163.

Isabelle Migeotie, et al.; Formyl peptide receptors: A promiscuous subfamily of G protein-coupled receptors controlling immune responses; Cytokine & Growth Factor Reviews 17 (2006) 501-519; Belgium.

Zeng Guangzhi; Structure-Activity Relationships of Di- and Tripeptide Sweeteners; Chinese Journal of Applied Chemistry 1990, pp. 1-9; Shanghai Institute of Organic Chemistry, Academia Sinica, Shanghai.

International Search Report for PCT/US2012/061448, dated Mar. 27, 2013.

Sun et al. "Solid-Phase Synthesis of a Thymidinyl Dipeptide Urea Library" J. Comb. Chem. 2007, 9, 370-385.

Scozzafava et al. "Protease Inhibitors: Synthesis of Matrix Metalloproteinase and Bacterial Collagenase Inhibitors Incorporating 5-Amino-2-mercapto-1,3,4-thiadiazole Zinc Binding Functions" Bioorg. Med. Chem. Lett. 2002, 12, 2667-2672.

Moller et al. "Synthesis and Spectroscopic Characterization of 4-Chlorophenyl Isocyanate (= 1-Chloro-4-isocyanatobenzene) Adducts with Amino Acids as Potential Dosimeters for the Biomonitoring of Isocyanate Exposure" Helv. Chim. Acta. 1998, 81, 1254-1263.

\* cited by examiner

AMIDE DERIVATIVES OF N-UREA SUBSTITUTED AMINO ACIDS AS FORMYL PEPTIDE RECEPTOR LIKE-1 (FPRL-1) RECEPTOR MODULATORS

CROSS REFERENCE TO RELATED APPLICATIONS

This application is a continuation of U.S. patent application Ser. No. 15/138,823 filed on Apr. 26, 2016, which is a continuation of U.S. patent application Ser. No. 14/608,503 filed on Jan. 29, 2015, issued as U.S. Pat. No. 9,351,948 B2 on May 31, 2016, which is a continuation of U.S. patent application Ser. No. 14/102,145 filed on Dec. 10, 2013, issued as U.S. Pat. No. 8,993,780 B2 on Mar. 31, 2015, which is a divisional of U.S. patent application Ser. No. 13/658,523 filed on Oct. 23, 2012, issued as U.S. Pat. No. 8,658,803 B2 on Feb. 25, 2014, which claims the benefit of priority to U.S. Provisional Application Ser. No. 61/551,772 filed on Oct. 26, 2011, each of which is hereby incorporated by reference in its entirety.

FIELD OF THE INVENTION

The present invention relates to novel amide derivatives of N-urea substituted amino acids, processes for preparing them, pharmaceutical compositions containing them and their use as pharmaceuticals as modulators of the N-formyl peptide receptor like-1 (FPRL-1) receptor. The invention relates specifically to the use of these compounds and their pharmaceutical compositions to treat disorders associated with the N-formyl peptide receptor like-1 (FPRL-1) receptor modulation.

BACKGROUND OF THE INVENTION

The N-formyl peptide receptor like-1 (FPRL-1) receptor is a G protein-coupled receptor that is expressed on inflammatory cells such as monocytes and neutrophils, as well as T cells and has been shown to play a critical role in leukocyte trafficking during inflammation and human pathology. FPRL-1 is an exceptionally promiscuous receptor that responds to a large array of exogenous and endogenous ligands, including Serum amyloid A (SAA), chemokine variant sCKβ8-1, the neuroprotective peptide human, anti-inflammatory eicosanoid lipoxin A4 (LXA4) and glucocorticoid-modulated protein annexin A1. FPRL-1 transduces anti-inflammatory effects of LXA4 in many systems, but it also can mediate the pro-inflammatory signaling cascade of peptides such as SAA. The ability of the receptor to mediate two opposite effects is proposed to be a result of different receptor domains used by different agonists (Parmentier, Marc et al. Cytokine & Growth Factor Reviews 17 (2006) 501-519).

Activation of FPRL-1 by LXA4 or its analogs and by Annexin I protein has been shown to result in anti-inflammatory activity by promoting active resolution of inflammation which involves inhibition of polymorphonuclear neutrophil (PMN) and eosinophil migration and also stimulate monocyte migration enabling clearance of apoptotic cells from the site of inflammation in a nonphlogistic manner. In addition, FPRL-1 has been shown to inhibit natural killer (NK) cell cytotoxicity and promote activation of T cells which further contributes to down regulation of tissue damaging inflammatory signals. FPRL-1/LXA4 interaction has been shown to be beneficial in experimental models of ischemia reperfusion, angiogenesis, dermal inflammation, chemotherapy-induced alopecia, ocular inflammation such as endotoxin-induced uveitis, corneal wound healing, re-epithelialization etc. FPRL-1 thus represents an important novel pro-resolutionary molecular target for the development of new therapeutic agents in diseases with excessive inflammatory responses.

JP 06172288 discloses the preparation of phenylalanine derivatives of general formula:

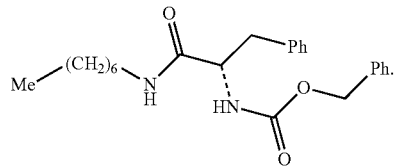

as inhibitors of acyl-coenzyme A:cholesterol acyltransferase derivatives useful for the treatment of arteriosclerosis-related various diseases such as angina pectoris, cardiac infarction, temporary ischemic spasm, peripheral thrombosis or obstruction.

Journal of Combinatorial Chemistry (2007), 9(3), 370-385 teaches a thymidinyl dipeptide urea library with structural similarity to the nucleoside peptide class of antibiotics:

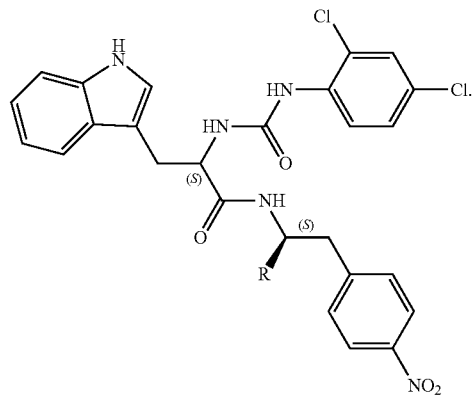

WO 9965932 discloses tetrapeptides or analogs or peptidomimetics that selectively bind mammalian opioid receptors:

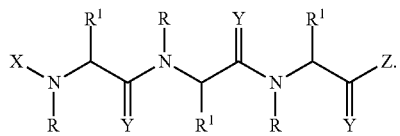

Helvetica Chimica Acta (1998), 81(7), 1254-1263 teaches the synthesis and spectroscopic characterization of 4-chlorophenyl isocyanate (1-chloro-4-isocyanatobenzene) adducts with amino acids as potential dosimeters for the biomonitoring of isocyanate exposure:

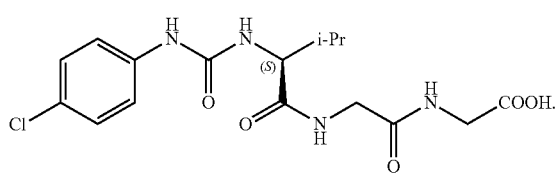

EP 457195 discloses the preparation of peptides having endothelin antagonist activity and pharmaceutical compositions comprising them:

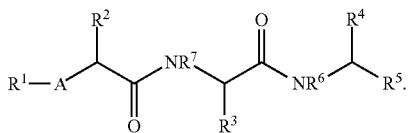

Yingyong Huaxue (1990), 7(1), 1-9 teaches the structure-activity relations of di- and tripeptide sweeteners and of L-phenyl alanine derivatives:

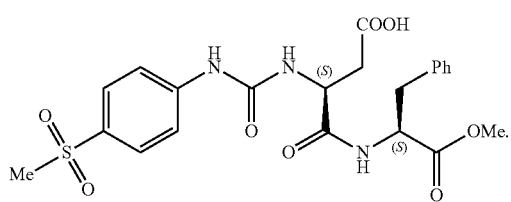

FR 2533210 discloses L-phenyl alanine derivatives as synthetic sweeteners:

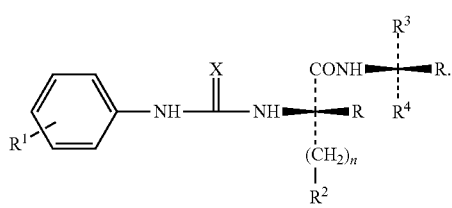

WO2005047899 discloses compounds which selectively activate the FPRL-1 receptor represented by the following scaffolds:

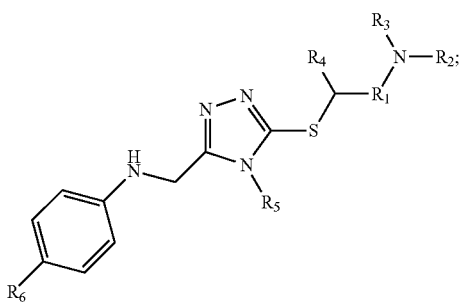

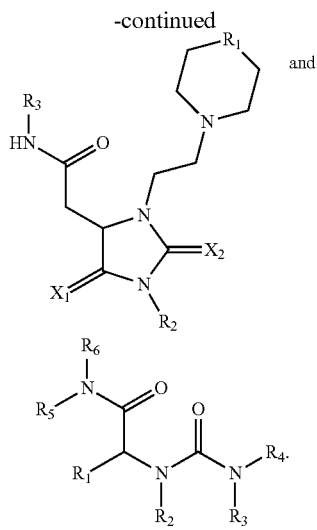

SUMMARY OF THE INVENTION

A group of amide derivatives of N-urea substituted amino acids, which are potent and selective FPRL-1 modulators, has been discovered. As such, the compounds described herein are useful in treating a wide variety of disorders associated with modulation of FPRL-1 receptor. The term "modulator" as used herein, includes but is not limited to: receptor agonist, antagonist, inverse agonist, inverse antagonist, partial agonist, and partial antagonist.

This invention describes compounds of Formula I, which have FPRL-1 receptor biological activity. The compounds in accordance with the present invention are thus of use in medicine, for example in the treatment of humans with diseases and conditions that are alleviated by FPRL-1 modulation.

In one aspect, the invention provides a compound represented by Formula I or the individual geometrical isomers, individual enantiomers, individual diastereoisomers, individual tautomers, individual zwitterions or a pharmaceutically acceptable salt thereof:

Formula I

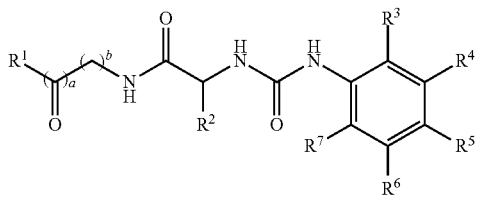

wherein:
a is 0 or 1;
b is 0, 1, 2, 3 or 4;
$R^1$ is optionally substituted $C_{1-8}$ alkyl, optionally substituted $C_{3-8}$ cycloalkyl, optionally substituted heterocycle, optionally substituted $C_{3-8}$ cycloalkyl, optionally substituted $C_{6-10}$ aryl, optionally substituted $C_{3-8}$ cycloalkenyl, —$NH_2$, —OH, —O($C_{1-8}$ alkyl),
$R^2$ is optionally substituted $C_{1-8}$ alkyl, optionally substituted $C_{6-10}$ aryl, $R^3$ is H, optionally substituted $C_{1-8}$ alkyl, halogen, —COOH, —OH, —NH$_2$, NO$_2$, optionally substituted heterocycle, optionally substituted $C_{3-8}$ cycloalkyl, optionally substituted $C_{6-10}$ aryl, optionally substituted $C_{3-8}$ cycloalkenyl;

$R^4$ is H, optionally substituted $C_{1-8}$ alkyl, halogen, —COOH, —OH, —NH$_2$, —NO$_2$, optionally substituted heterocycle, optionally substituted $C_{3-8}$ cycloalkyl, optionally substituted $C_{6-10}$ aryl, optionally substituted $C_{3-8}$ cycloalkenyl;

$R^5$ is optionally substituted $C_{1-8}$ alkyl, halogen, —COOH, —OH, —NH$_2$, —NO$_2$, optionally substituted heterocycle, optionally substituted $C_{3-8}$ cycloalkyl, optionally substituted $C_{6-10}$ aryl, optionally substituted $C_{3-8}$ cycloalkenyl;

$R^6$ is H, optionally substituted $C_{1-8}$ alkyl, halogen, —COOH, —OH, —NH$_2$, —NO$_2$, optionally substituted heterocycle, optionally substituted $C_{3-8}$ cycloalkyl, optionally substituted $C_{6-10}$ aryl, optionally substituted $C_{3-8}$ cycloalkenyl;

$R^7$ is H, optionally substituted $C_{1-8}$ alkyl, halogen, —COOH, —OH, —NH$_2$, —NO$_2$, optionally substituted heterocycle, optionally substituted $C_{3-8}$ cycloalkyl, optionally substituted $C_{6-10}$ aryl, optionally substituted $C_{3-8}$ cycloalkenyl;

and compounds:

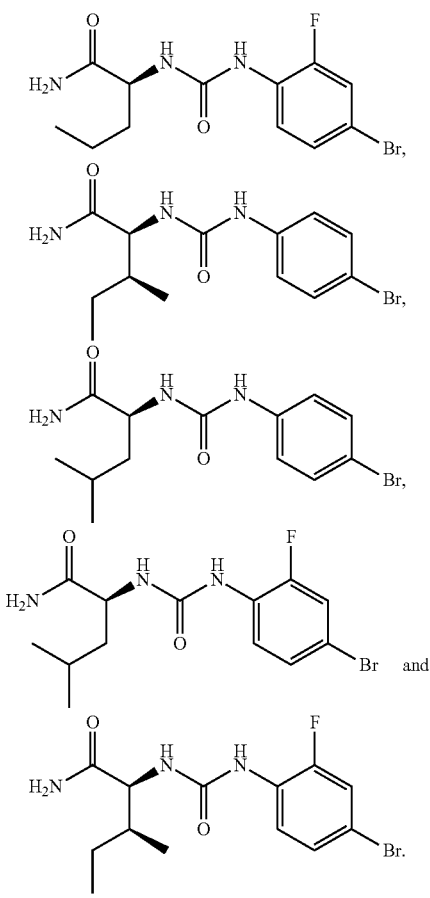

In another aspect, the invention provides a compound represented by Formula II or the geometrical isomers, enantiomers, diastereoisomers, tautomers, zwitterions, hydrates, crystal forms, solvates or a pharmaceutically acceptable salt thereof:

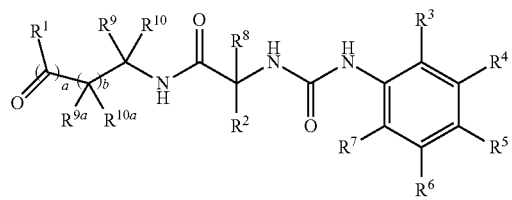

Formula II wherein:

a is 1 and b is 0;

a is 0 and b is 1;

a is 1 and b is 1;

$R^1$ is optionally substituted $C_{1-8}$ alkyl, optionally substituted $C_{3-8}$ cycloalkyl, optionally substituted heterocycle, optionally substituted $C_{3-8}$ cycloalkyl, optionally substituted $C_{6-10}$ aryl, optionally substituted $C_{3-8}$ cycloalkenyl, —NR$^{11}$R$^{12}$ or —OR$^{13}$;

$R^2$ is optionally substituted $C_{1-8}$ alkyl or optionally substituted $C_{6-10}$ aryl;

$R^3$ is hydrogen, optionally substituted $C_{1-8}$ alkyl, halogen, —COOR$^{15}$, —OR$^{13}$, —NR$^{11}$R$^{12}$, NO$_2$, optionally substituted heterocycle, optionally substituted $C_{3-8}$ cycloalkyl, optionally substituted $C_{6-10}$ aryl or optionally substituted $C_{3-8}$ cycloalkenyl;

$R^4$ is hydrogen, optionally substituted $C_{1-8}$ alkyl, halogen, —COOR$^{15}$, —OR$^{13}$, —NR$^{11}$R$^{12}$, NO$_2$, optionally substituted heterocycle, optionally substituted $C_{3-8}$ cycloalkyl, optionally substituted $C_{6-10}$ aryl or optionally substituted $C_{3-8}$ cycloalkenyl;

$R^5$ is halogen, —CF$_3$ or —S(O)$_n$R$^{14}$;

n is 0, 1 or 2;

$R^6$ is hydrogen, optionally substituted $C_{1-8}$ alkyl, halogen, —COOR$^{15}$, —OR$^{13}$, —NR$^{11}$R$^{12}$, NO$_2$, optionally substituted heterocycle, optionally substituted $C_{3-8}$ cycloalkyl, optionally substituted $C_{6-10}$ aryl or optionally substituted $C_{3-8}$ cycloalkenyl;

$R^7$ is hydrogen, optionally substituted $C_{1-8}$ alkyl, halogen, —COOR$^{15}$, —OR$^{13}$, —NR$^{11}$R$^{12}$, NO$_2$, optionally substituted heterocycle, optionally substituted $C_{3-8}$ cycloalkyl, optionally substituted $C_{6-10}$ aryl or optionally substituted $C_{3-8}$ cycloalkenyl;

$R^8$ is hydrogen, optionally substituted $C_{1-8}$ alkyl or optionally substituted $C_{6-10}$ aryl;

$R^9$ is hydrogen, optionally substituted $C_{1-8}$ alkyl or optionally substituted $C_{6-10}$ aryl;

$R^{19}$ is hydrogen, optionally substituted $C_{1-8}$ alkyl or optionally substituted $C_{6-10}$ aryl;

$R^{9a}$ is hydrogen, optionally substituted $C_{1-8}$ alkyl or optionally substituted $C_{6-10}$ aryl;

$R^{10a}$ is hydrogen, optionally substituted $C_{1-8}$ alkyl or optionally substituted $C_{6-10}$ aryl;

$R^{11}$ is hydrogen or optionally substituted $C_{1-8}$ alkyl;

$R^{12}$ is hydrogen or optionally substituted $C_{1-8}$ alkyl;

$R^{13}$ is hydrogen or optionally substituted $C_{1-8}$ alkyl;

$R^{14}$ is hydrogen, CF$_3$ or optionally substituted $C_{1-8}$ alkyl;

$R^{15}$ is hydrogen or optionally substituted $C_{1-8}$ alkyl;

with the provisos:

a). when a=1 and b=0 then:

$R^9$ is not optionally substituted benzyl; and $R^1$ is not:
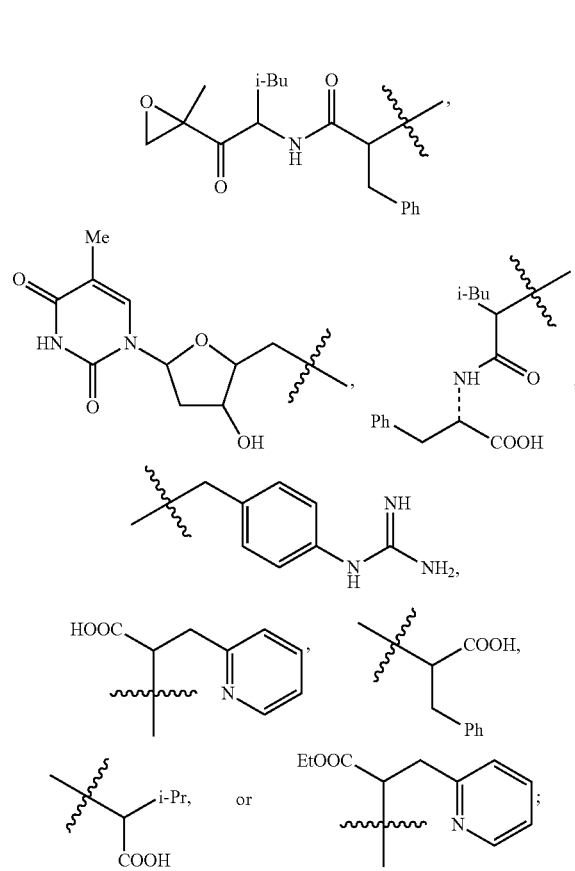
and
the compound of Formula II is not of structures:
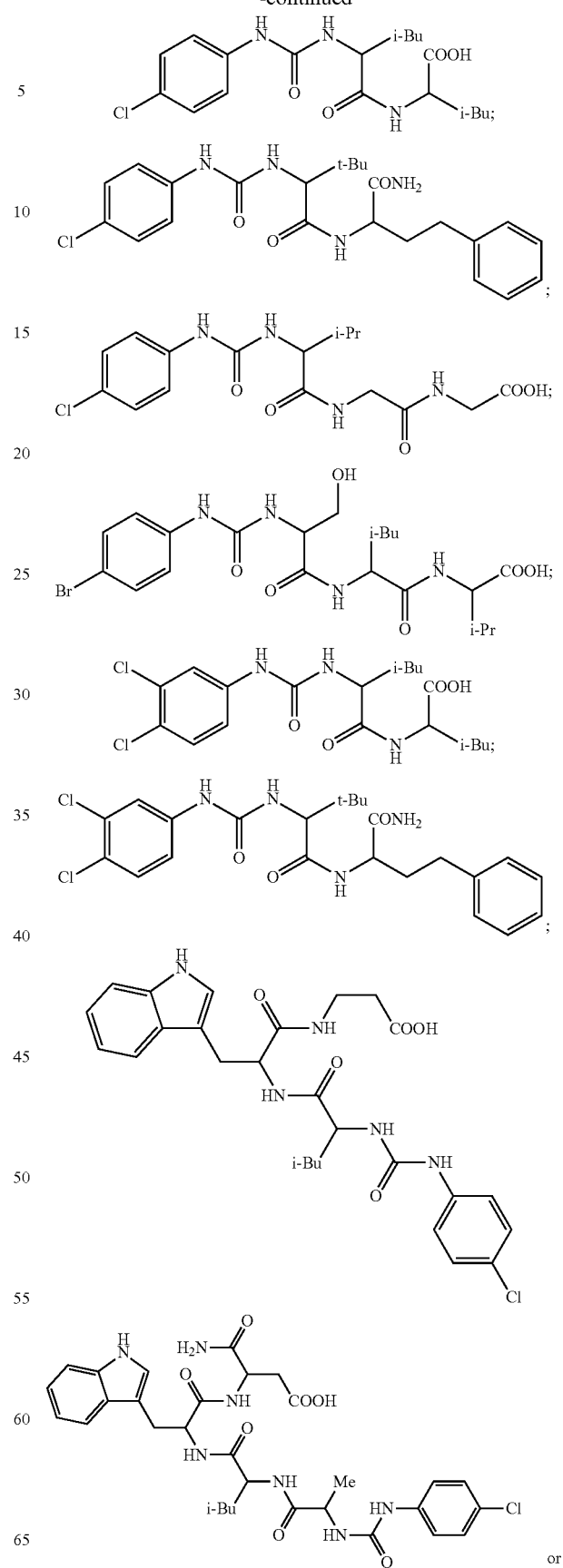

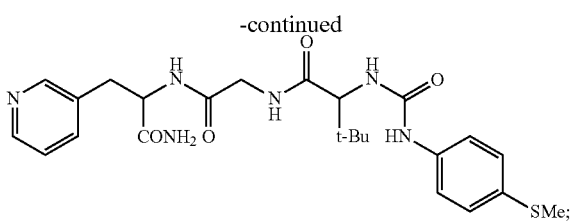

and b). when a=0 and b=1 then:
R$^1$ is OR$^{13}$; and
the compound of Formula II is not of structure:

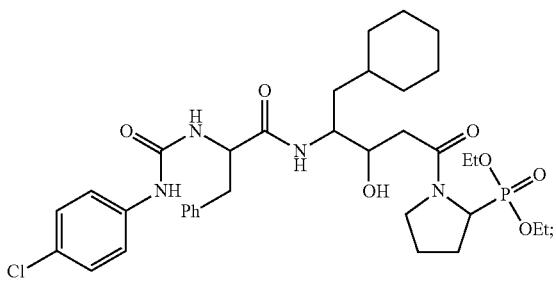 [SMILES: CCOP(=O)(OCC)C1CCCN1C(=O)CC(O)C(CC1CCCCC1)NC(=O)C(Cc1ccccc1)NC(=O)Nc1ccc(Cl)cc1]

and c). when a=1 and b=1 then:
R$^{11}$ is not:

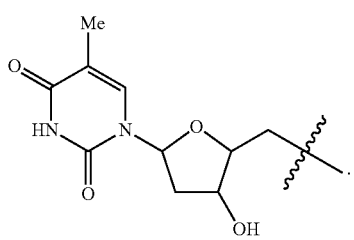

In another aspect, the invention provides a compound represented by Formula II,
wherein:
a is 1 and b is 0;
R$^1$ is optionally substituted C$_{1-8}$ alkyl, optionally substituted C$_{3-8}$ cycloalkyl, optionally substituted heterocycle, optionally substituted C$_{3-8}$ cycloalkyl, optionally substituted C$_{6-10}$ aryl, optionally substituted C$_{3-8}$ cycloalkenyl, —NR$^{11}$R$^{12}$ or —OR$^{13}$;
R$^2$ is optionally substituted C$_{1-8}$ alkyl or optionally substituted C$_{6-10}$ aryl;
R$^3$ is hydrogen, optionally substituted C$_{1-8}$ alkyl, halogen, —COOR$^{15}$, —OR$^{13}$, —NR$^{11}$R$^{12}$, NO$_2$, optionally substituted heterocycle, optionally substituted C$_{3-8}$ cycloalkyl, optionally substituted C$_{6-10}$ aryl or optionally substituted C$_{3-8}$ cycloalkenyl;
R$^4$ is hydrogen, optionally substituted C$_{1-8}$ alkyl, halogen, —COOR$^{15}$, —OR$^{13}$, —NR$^{11}$R$^{12}$, NO$_2$, optionally substituted heterocycle, optionally substituted C$_{3-8}$ cycloalkyl, optionally substituted C$_{6-10}$ aryl or optionally substituted C$_{3-8}$ cycloalkenyl;
R$^5$ is halogen, —CF$_3$ or —S(O)$_n$R$^{14}$;
n is 0, 1 or 2;
R$^6$ is hydrogen, optionally substituted C$_{1-8}$ alkyl, halogen, —COOR$^{15}$, —OR$^{13}$, —NR$^{11}$R$^{12}$, NO$_2$, optionally substituted heterocycle, optionally substituted C$_{3-8}$ cycloalkyl, optionally substituted C$_{6-10}$ aryl or optionally substituted C$_{3-8}$ cycloalkenyl;

R$^7$ is hydrogen, optionally substituted C$_{1-8}$ alkyl, halogen, —COOR$^{15}$, —OR$^{13}$, —NR$^{11}$R$^{12}$, NO$_2$, optionally substituted heterocycle, optionally substituted C$_{3-8}$ cycloalkyl, optionally substituted C$_{6-10}$ aryl or optionally substituted C$_{3-8}$ cycloalkenyl;

R$^8$ is hydrogen, optionally substituted C$_{1-8}$ alkyl or optionally substituted C$_{6-10}$ aryl;

R$^9$ is hydrogen, optionally substituted C$_{1-8}$ alkyl or optionally substituted C$_{6-10}$ aryl;

R$^{10}$ is hydrogen, optionally substituted C$_{1-8}$ alkyl or optionally substituted C$_{6-10}$ aryl;

R$^{11}$ is hydrogen or optionally substituted C$_{1-8}$ alkyl;

R$^{12}$ is hydrogen or optionally substituted C$_{1-8}$ alkyl;

R$^{13}$ is hydrogen or optionally substituted C$_{1-8}$ alkyl;

R$^{14}$ is hydrogen, CF$_3$ or optionally substituted C$_{1-8}$ alkyl;

R$^{15}$ is hydrogen or optionally substituted C$_{1-8}$ alkyl;

with the provisos:

R$^9$ is not optionally substituted benzyl; and

R$^{11}$ is not:

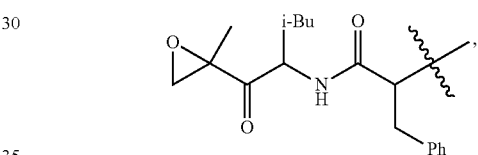

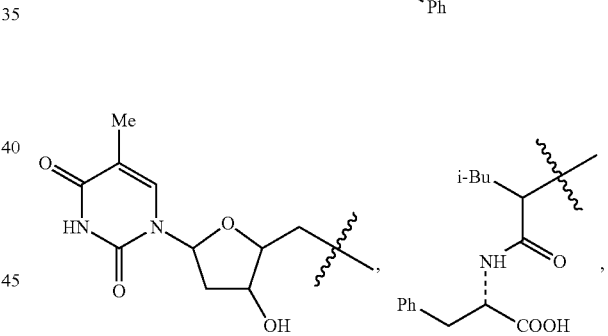

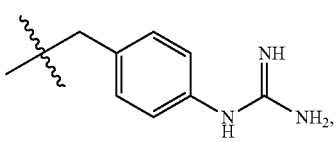

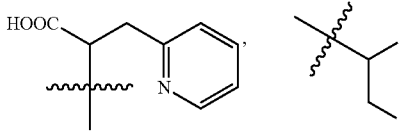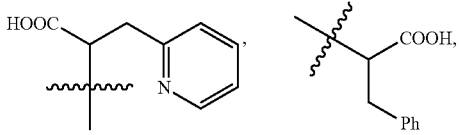

-continued

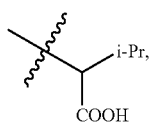 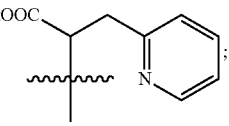

and the compound of Formula II is not of structures:

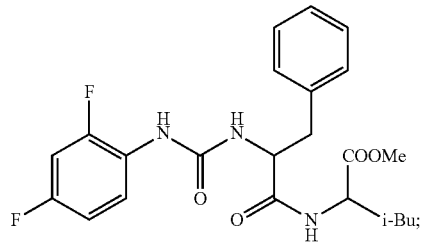

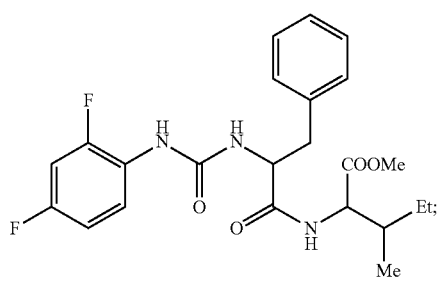

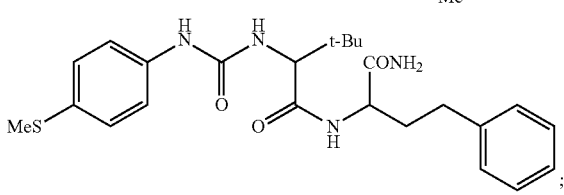

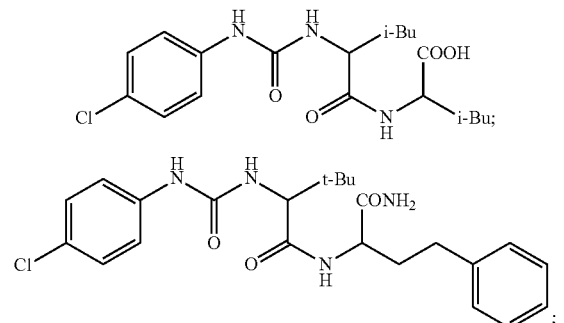

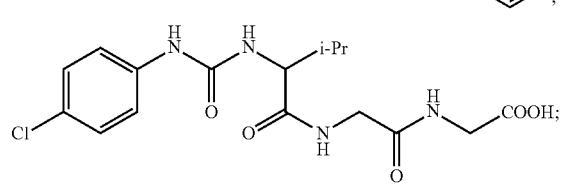

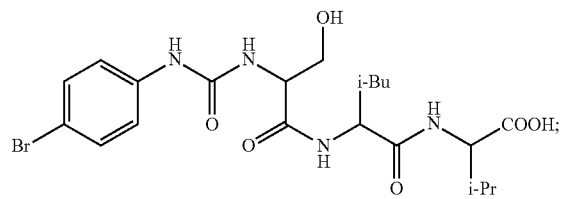

-continued

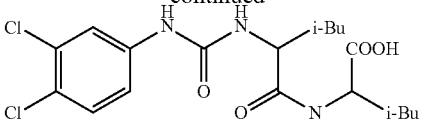

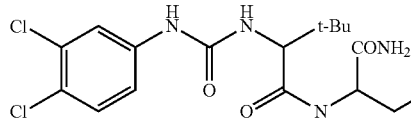

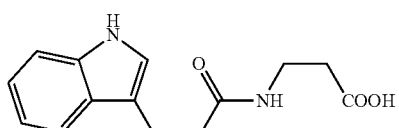

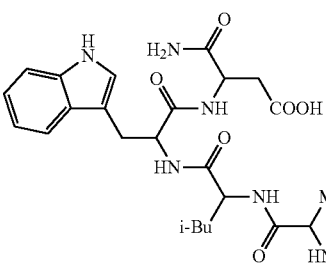

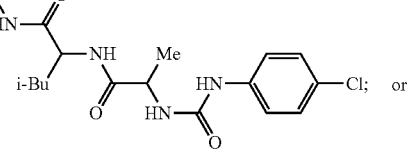

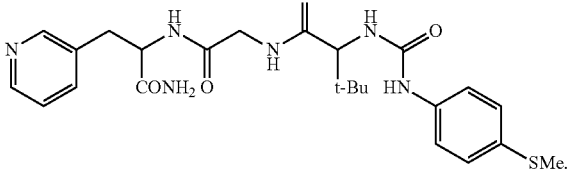

In another aspect, the invention provides a compound represented by Formula II, wherein:

a is 1 and b is 0;

$R^1$ is optionally substituted $C_{1-8}$ alkyl, optionally substituted $C_{3-8}$ cycloalkyl, optionally substituted heterocycle, optionally substituted $C_{3-8}$ cycloalkyl, optionally substituted $C_{6-10}$ aryl, optionally substituted $C_{3-8}$ cycloalkenyl, —$NR^{11}R^{12}$ or —$OR^{13}$;

$R^2$ is optionally substituted $C_{1-8}$ alkyl or optionally substituted $C_{6-10}$ aryl;

$R^3$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;

$R^4$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;

R⁵ is S(O)ₙR¹⁴;

n is 0, 1 or 2;

R⁶ is hydrogen, optionally substituted C₁₋₈ alkyl, halogen, —COOR¹⁵, —OR¹³, —NR¹¹R¹², NO₂, optionally substituted heterocycle, optionally substituted C₃₋₈ cycloalkyl, optionally substituted C₆₋₁₀ aryl or optionally substituted C₃₋₈ cycloalkenyl;

R⁷ is hydrogen, optionally substituted C₁₋₈ alkyl, halogen, —COOR¹⁵, —OR¹³, —NR¹¹R¹², NO₂, optionally substituted heterocycle, optionally substituted C₃₋₈ cycloalkyl, optionally substituted C₆₋₁₀ aryl or optionally substituted C₃₋₈ cycloalkenyl;

R⁸ is hydrogen, optionally substituted C₁₋₈ alkyl or optionally substituted C₆₋₁₀ aryl;

R⁹ is hydrogen, optionally substituted C₁₋₈ alkyl or optionally substituted C₆₋₁₀ aryl;

R¹⁰ is hydrogen, optionally substituted C₁₋₈ alkyl or optionally substituted C₆₋₁₀ aryl;

R¹¹ is hydrogen or optionally substituted C₁₋₈ alkyl;

R¹² is hydrogen or optionally substituted C₁₋₈ alkyl;

R¹³ is hydrogen or optionally substituted C₁₋₈ alkyl;

R¹⁴ is hydrogen, CF₃ or optionally substituted C₁₋₈ alkyl;

R¹⁵ is hydrogen or optionally substituted C₁₋₈ alkyl;

with the provisos:

R⁹ is not optionally substituted benzyl; and

R¹¹ is not:

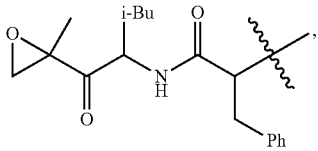

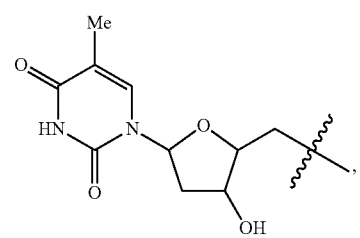 [SMILES: *CC1OC(n2cc(C)c(=O)[nH]c2=O)CC1O] 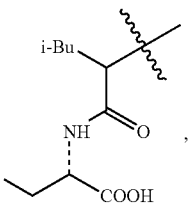

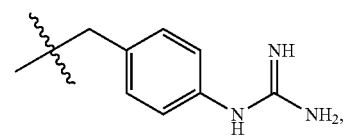

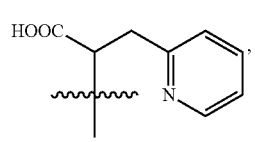 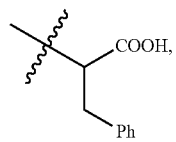

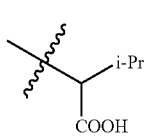 or 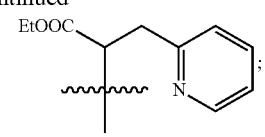;

and the compound of Formula II is not of structures:

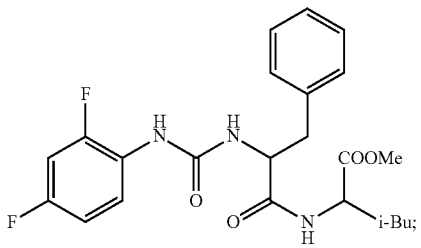

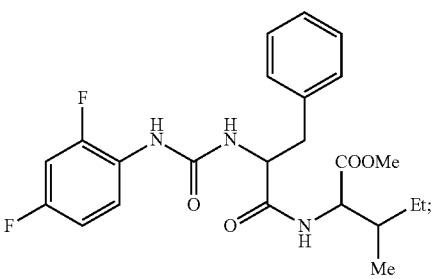

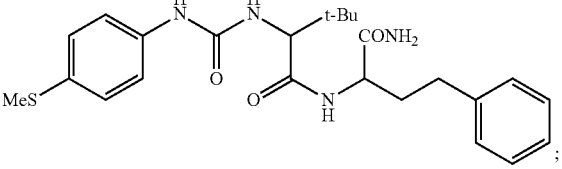;

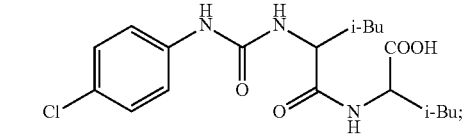

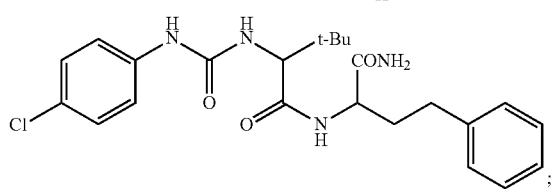;

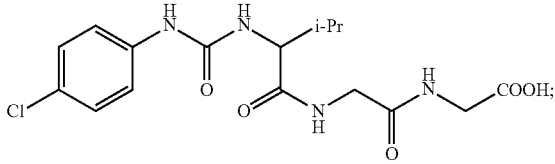

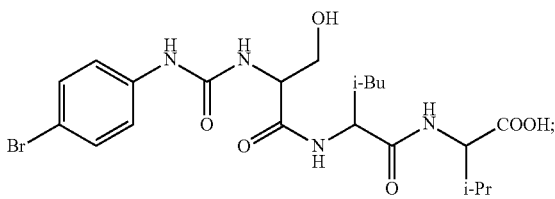

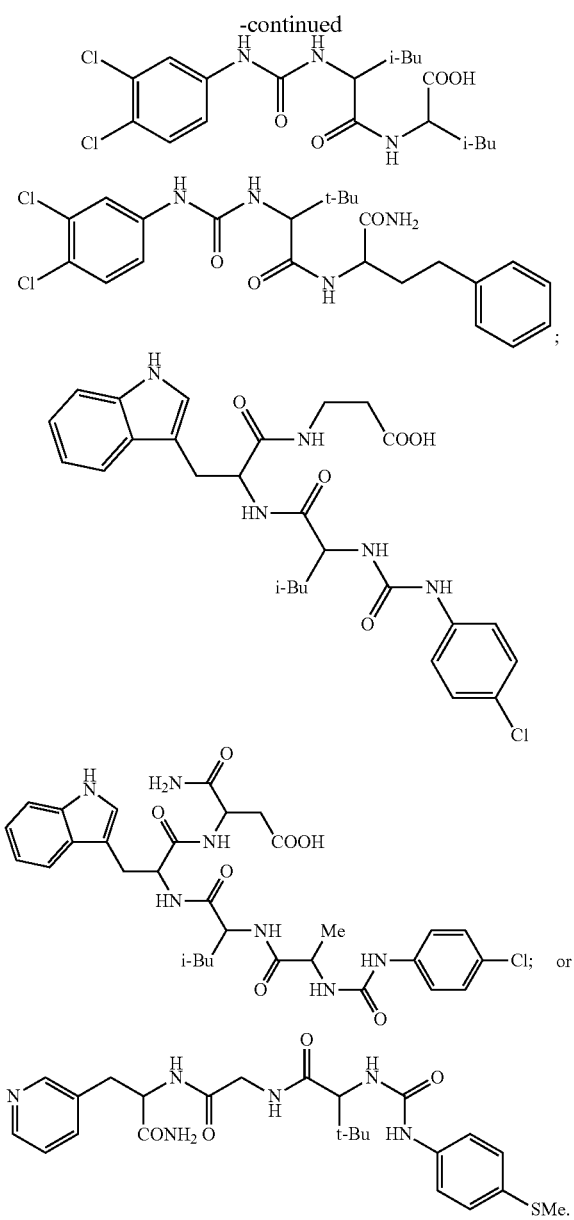

In another aspect, the invention provides a compound represented by Formula II,
wherein:
a is 1 and b is 0;
$R^1$ is optionally substituted $C_{1-8}$ alkyl, optionally substituted $C_{3-8}$ cycloalkyl, optionally substituted heterocycle, optionally substituted $C_{3-8}$ cycloalkyl, optionally substituted $C_{6-10}$ aryl, optionally substituted $C_{3-8}$ cycloalkenyl, —$NR^{11}R^{12}$ or —$OR^{13}$;
$R^2$ is optionally substituted $C_{1-8}$ alkyl or optionally substituted $C_{6-10}$ aryl;
$R^3$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^4$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^5$ is —$CF_3$;
$R^6$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^7$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^8$ is hydrogen, optionally substituted $C_{1-8}$ alkyl or optionally substituted $C_{6-10}$ aryl;
$R^9$ is hydrogen, optionally substituted $C_{1-8}$ alkyl or optionally substituted $C_{6-10}$ aryl;
$R^{10}$ is hydrogen, optionally substituted $C_{1-8}$ alkyl or optionally substituted $C_{6-10}$ aryl;
$R^{11}$ is hydrogen or optionally substituted $C_{1-8}$ alkyl;
$R^{12}$ is hydrogen or optionally substituted $C_{1-8}$ alkyl;
$R^{13}$ is hydrogen or optionally substituted $C_{1-8}$ alkyl;
$R^{15}$ is hydrogen or optionally substituted $C_{1-8}$ alkyl;
with the provisos:
$R^9$ is not optionally substituted benzyl; and
$R^{11}$ is not:

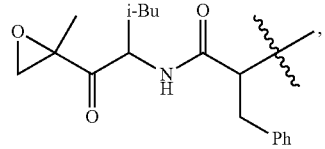

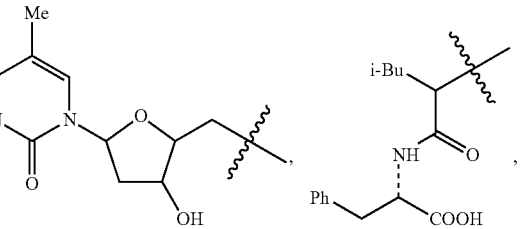

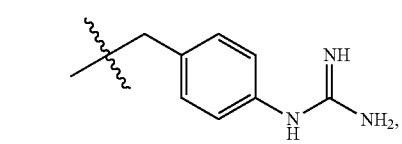

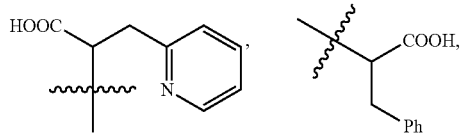

-continued

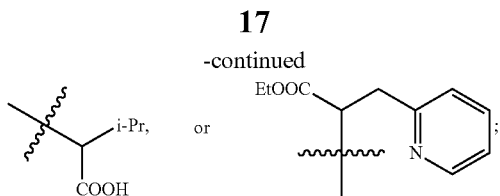

and the compound of Formula II is not of structures:

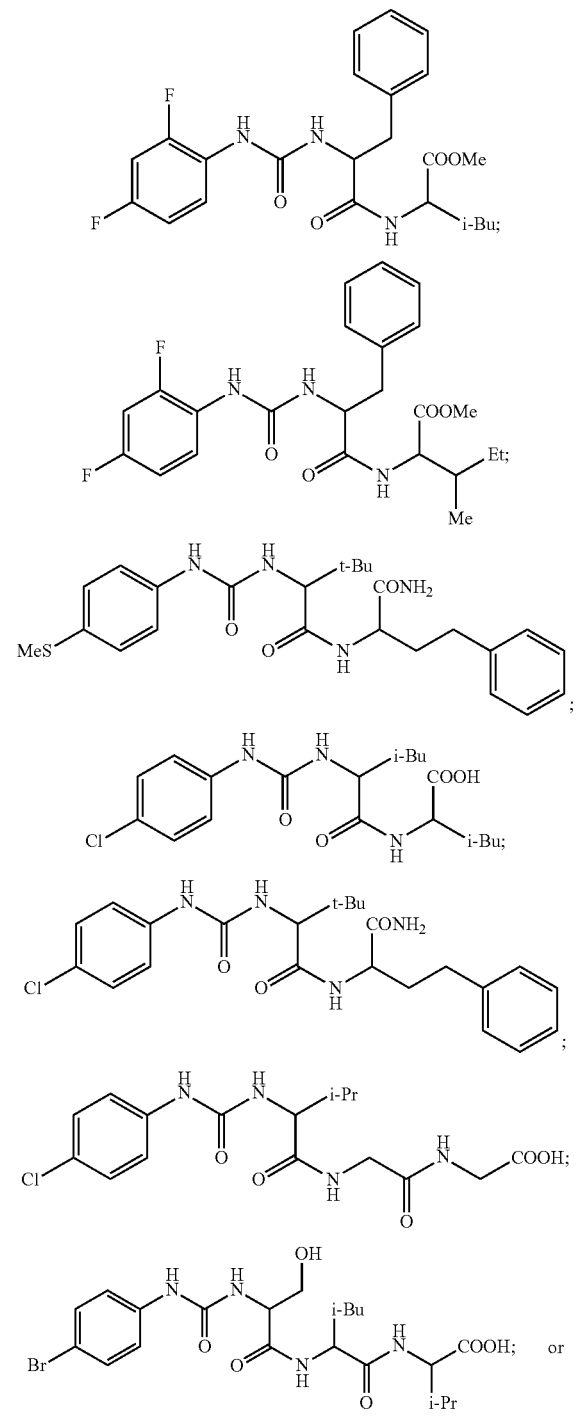

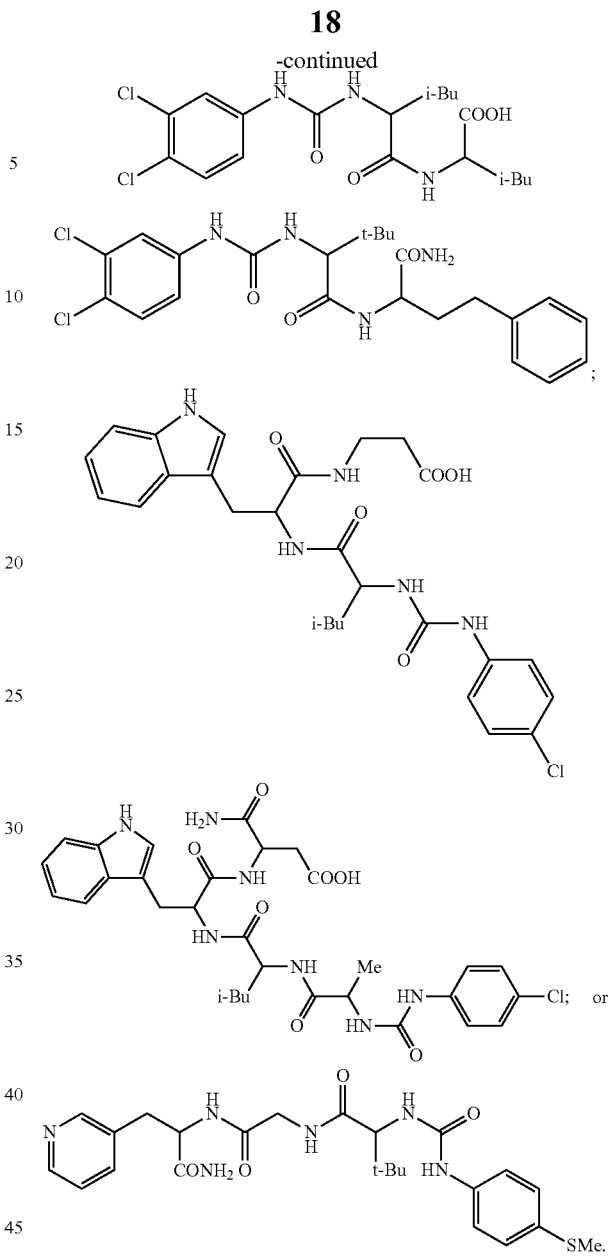

In another aspect, the invention provides a compound represented by Formula II, wherein:

a is 1 and b is 0;

$R^1$ is optionally substituted $C_{1-8}$ alkyl, optionally substituted $C_{3-8}$ cycloalkyl, optionally substituted heterocycle, optionally substituted $C_{3-8}$ cycloalkyl, optionally substituted $C_{6-10}$ aryl, optionally substituted $C_{3-8}$ cycloalkenyl, —$NR^{11}R^{12}$ or —$OR^{13}$;

$R^2$ is optionally substituted $C_{1-8}$ alkyl or optionally substituted $C_{6-10}$ aryl;

$R^3$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;

$R^4$ is hydrogen, optionally substituted $C_{1-8}$ alkyl, halogen, —$COOR^{15}$—$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;

$R^5$ is halogen;

$R^6$ is hydrogen, optionally substituted $C_{1-8}$ alkyl, halogen, —COOR$^{15}$, —OR$^{13}$, —NR$^{11}$R$^{12}$, NO$_2$, optionally substituted heterocycle, optionally substituted $C_{3-8}$ cycloalkyl, optionally substituted $C_{6-10}$ aryl or optionally substituted $C_{3-8}$ cycloalkenyl;

$R^7$ is hydrogen, optionally substituted $C_{1-8}$ alkyl, halogen, —COOR$^{15}$, —OR$^{13}$, —NR$^{11}$R$^{12}$, NO$_2$, optionally substituted heterocycle, optionally substituted $C_{3-8}$ cycloalkyl, optionally substituted $C_{6-10}$ aryl or optionally substituted $C_{3-8}$ cycloalkenyl;

$R^8$ is hydrogen, optionally substituted $C_{1-8}$ alkyl or optionally substituted $C_{6-10}$ aryl;

$R^9$ is hydrogen, optionally substituted $C_{1-8}$ alkyl or optionally substituted $C_{6-10}$ aryl;

$R^{10}$ is hydrogen, optionally substituted $C_{1-8}$ alkyl or optionally substituted $C_{6-10}$ aryl;

$R^{11}$ is hydrogen or optionally substituted $C_{1-8}$ alkyl;

$R^{12}$ is hydrogen or optionally substituted $C_{1-8}$ alkyl;

$R^{13}$ is hydrogen or optionally substituted $C_{1-8}$ alkyl;

$R^{15}$ is hydrogen or optionally substituted $C_{1-8}$ alkyl;

with the provisos:

$R^9$ is not optionally substituted benzyl;

and the compound of Formula II is not of structures:

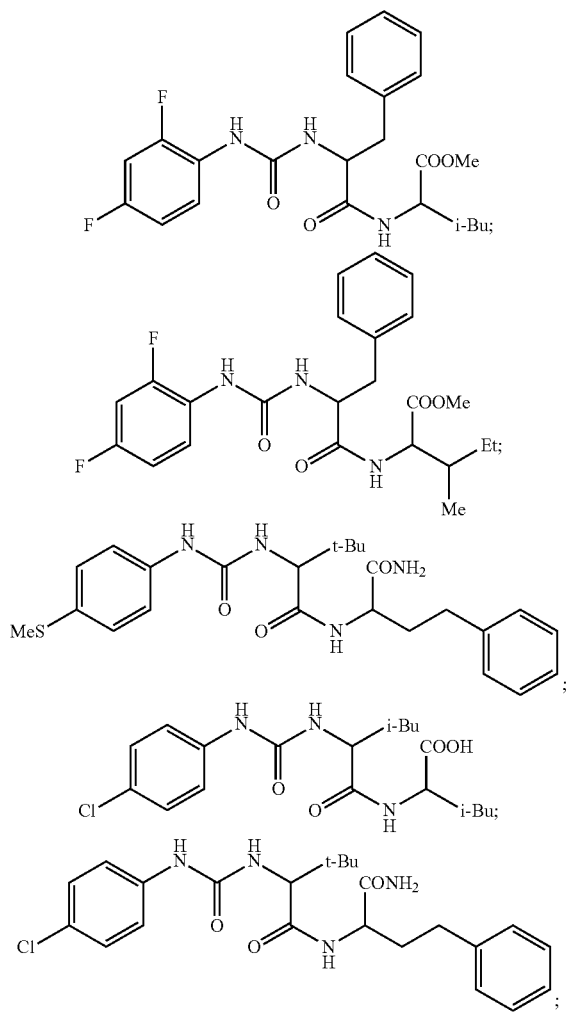

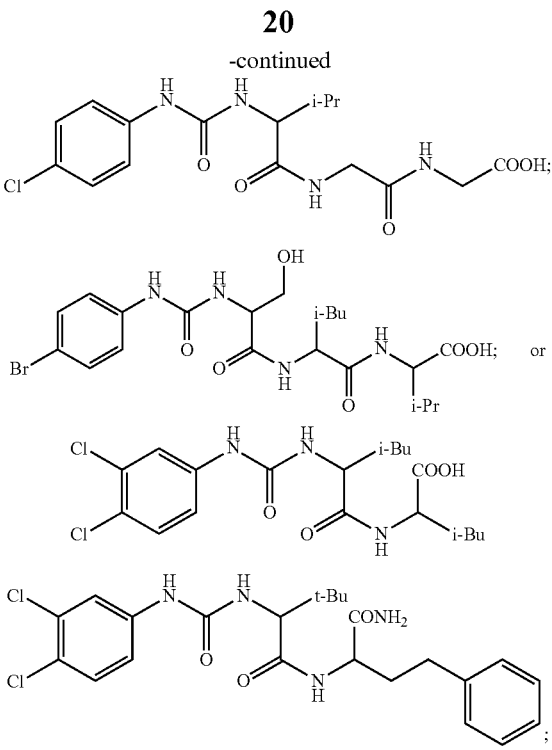

and

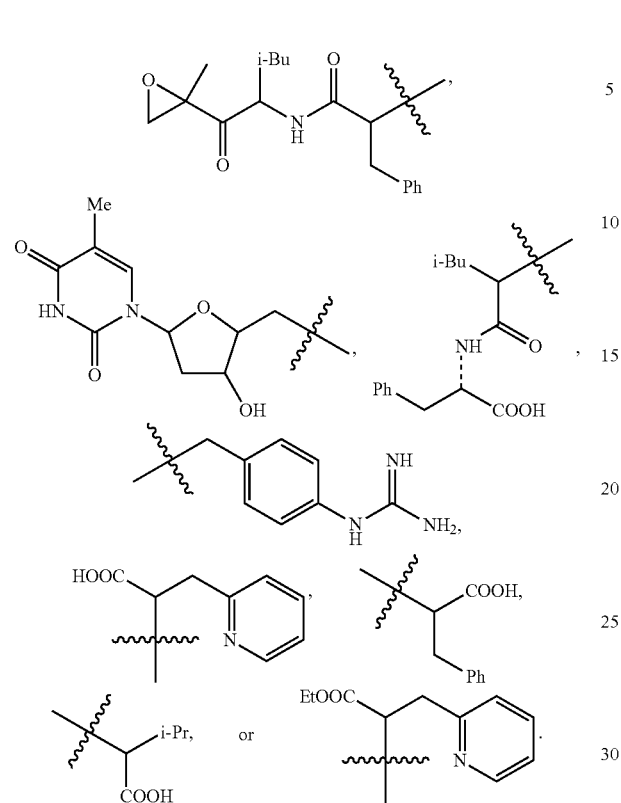

In another aspect, the invention provides a compound represented by Formula II,
wherein
a is 1 and b is 0;
$R^1$ is optionally substituted $C_{1-8}$ alkyl, $-NR^{11}R^{12}$ or $-OR^{13}$;
$R^2$ is optionally substituted $C_{1-8}$ alkyl;
$R^3$ is hydrogen, optionally substituted $C_{1-8}$ alkyl, halogen, $-COOR^{15}$, $-OR^{13}$, $-NR^{11}R^{12}$;
$R^4$ is hydrogen, optionally substituted $C_{1-8}$ alkyl, halogen, $-COOR^{15}$, $-OR^{13}$, $-NR^{11}R^{12}$;
$R^5$ is halogen, $-CF_3$ or $-S(O)_nR^{14}$;
n is 0, 1 or 2;
$R^6$ is hydrogen, optionally substituted $C_{1-8}$ alkyl, halogen, $-COOR^{15}$, $-OR^{13}$, $-NR^{11}R^{12}$;
$R^7$ is hydrogen, optionally substituted $C_{1-8}$ alkyl, halogen, $-COOR^{15}$, $-OR^{13}$, $-NR^{11}R^{12}$, $NO_2$,
$R^8$ is hydrogen or optionally substituted $C_{1-8}$ alkyl;
$R^9$ is hydrogen, optionally substituted $C_{1-8}$ alkyl or optionally substituted $C_{6-10}$ aryl;
$R^{10}$ is hydrogen or optionally substituted $C_{1-8}$;
$R^{11}$ is hydrogen or optionally substituted $C_{1-8}$ alkyl;
$R^{12}$ is hydrogen or optionally substituted $C_{1-8}$ alkyl;
$R^{13}$ is hydrogen or optionally substituted $C_{1-8}$ alkyl;
$R^{14}$ is hydrogen or optionally substituted $C_{1-8}$ alkyl;
$R^{15}$ is hydrogen or optionally substituted $C_{1-8}$ alkyl;
with the provisos:
$R^9$ is not optionally substituted benzyl;
and the compound of Formula II is not of structures:

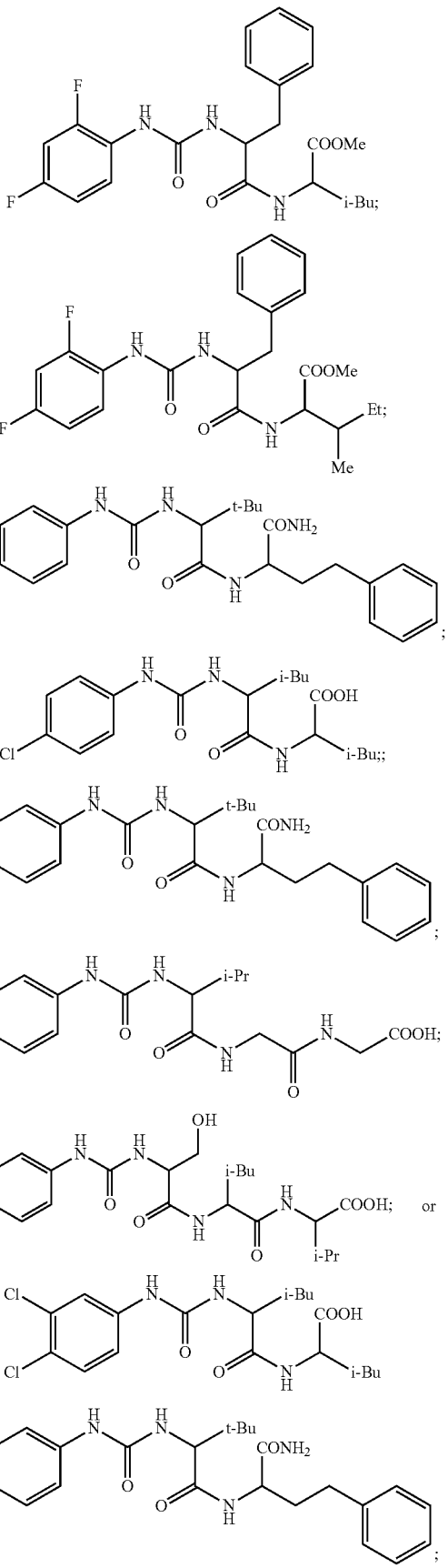

-continued

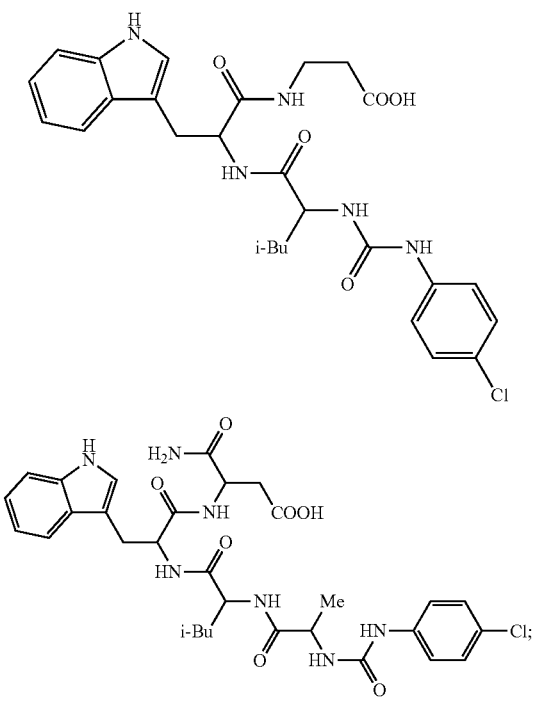

or

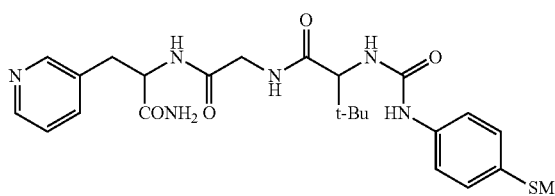

and
$R^{11}$ is not:

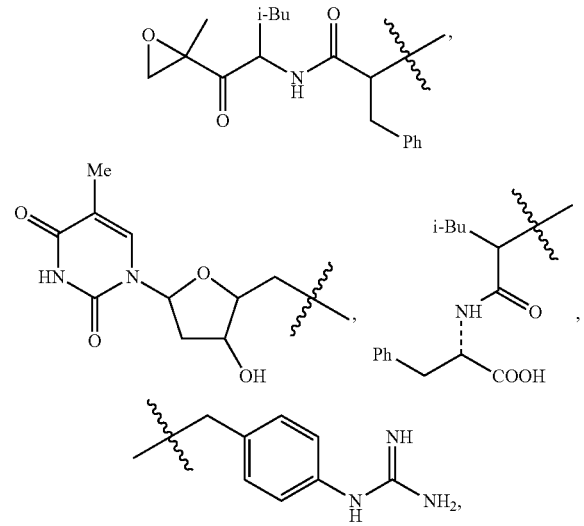

-continued

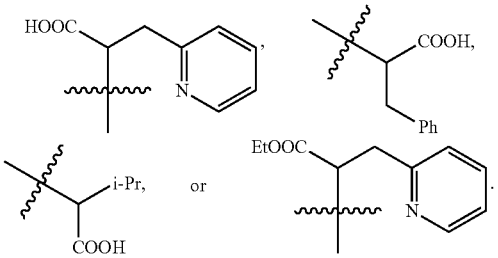

In another aspect, the invention provides a compound represented by Formula II,
wherein
a is 1 and b is 0;
$R^1$ is optionally substituted $C_{1-8}$ alkyl, —$NR^{11}R^{12}$ or —$OR^{13}$;
$R^2$ is optionally substituted $C_{1-8}$ alkyl;
$R^3$ is hydrogen or halogen;
$R^4$ is hydrogen;
$R^5$ is halogen, —$CF_3$ or —$S(O)_nR^{14}$;
n is 0, 1 or 2;
$R^6$ is hydrogen;
$R^7$ is hydrogen;
$R^8$ is hydrogen, optionally substituted $C_{1-8}$ alkyl;
$R^9$ is hydrogen, optionally substituted $C_{1-8}$ alkyl or optionally substituted $C_{6-10}$ aryl;
$R^{10}$ is hydrogen, optionally substituted $C_{1-8}$ alkyl;
$R^{11}$ is hydrogen or optionally substituted $C_{1-8}$ alkyl;
$R^{12}$ is hydrogen or optionally substituted $C_{1-8}$ alkyl;
$R^{13}$ is hydrogen or optionally substituted $C_{1-8}$ alkyl;
$R^{14}$ is hydrogen or optionally substituted $C_{1-8}$ alkyl;
with the provisos:
$R^9$ is not optionally substituted benzyl;
and the compound of Formula II is not of structures:

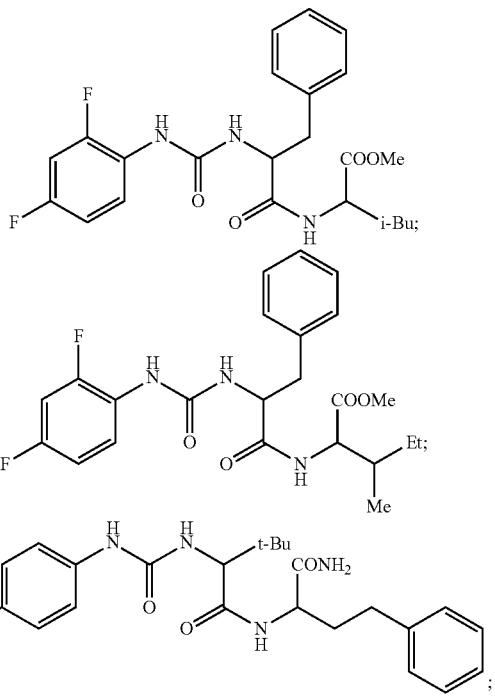

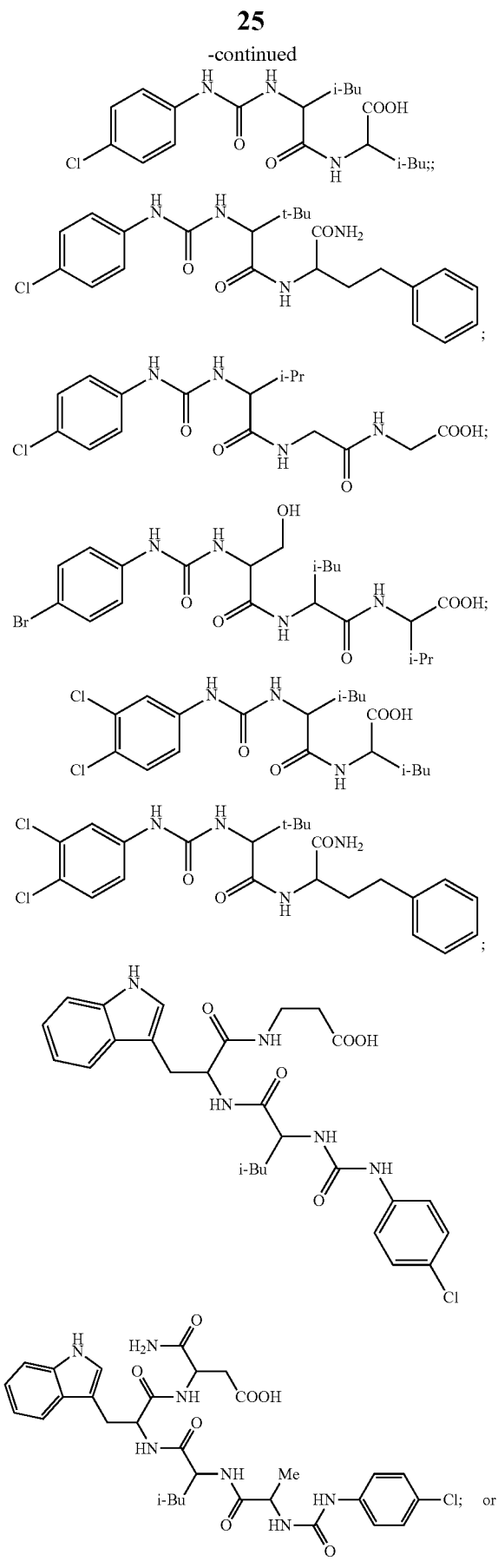

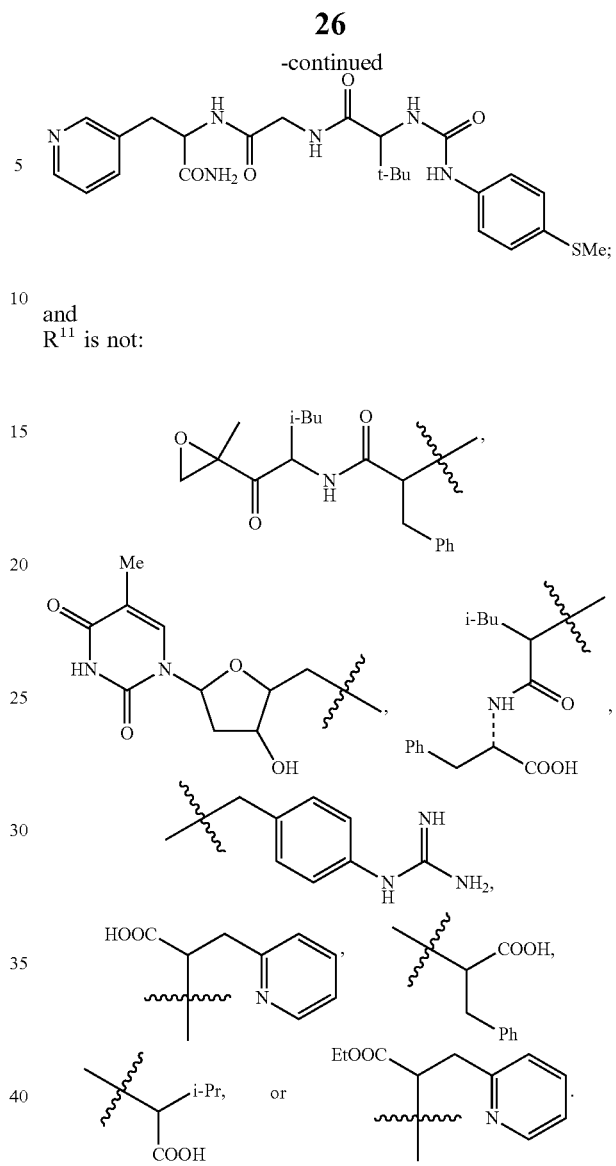

and
R[11] is not:

In another aspect, the invention provides a compound represented by Formula II,
wherein
a is 0 and b is 1;
R[1] is —OR[13];
R[2] is optionally substituted $C_{1-8}$ alkyl or optionally substituted $C_{6-10}$ aryl;
R[3] is hydrogen, optionally substituted $C_{1-8}$ alkyl, halogen, —COOR[15], —OR[13], —NR[11]R[12], $NO_2$, optionally substituted heterocycle, optionally substituted $C_{3-8}$ cycloalkyl, optionally substituted $C_{6-10}$ aryl or optionally substituted $C_{3-8}$ cycloalkenyl;
R[4] is hydrogen, optionally substituted $C_{1-8}$ alkyl, halogen, —COOR[15], —OR[13], —NR[11]R[12], $NO_2$, optionally substituted heterocycle, optionally substituted $C_{3-8}$ cycloalkyl, optionally substituted $C_{6-10}$ aryl or optionally substituted $C_{3-8}$ cycloalkenyl;
R[5] is halogen, —CF$_3$ or —S(O)$_n$R[14];
n is 0, 1 or 2;
R[6] is hydrogen, optionally substituted $C_{1-8}$ alkyl, halogen, —COOR[15], —OR[13], —NR[11]R[12], $NO_2$, optionally substituted heterocycle, optionally substituted $C_{3-8}$ cycloalkyl, optionally substituted $C_{6-10}$ aryl or optionally substituted $C_{3-8}$ cycloalkenyl;

$R^7$ is hydrogen, optionally substituted $C_{1-8}$ alkyl, halogen, —COOR$^{15}$, —OR$^{13}$, —NR$^{11}$R$^{12}$, NO$_2$, optionally substituted heterocycle, optionally substituted $C_{3-8}$ cycloalkyl, optionally substituted $C_{6-10}$ aryl or optionally substituted $C_{3-8}$ cycloalkenyl;

$R^8$ is hydrogen, optionally substituted $C_{1-8}$ alkyl or optionally substituted $C_{6-10}$ aryl;

$R^9$ is hydrogen, optionally substituted $C_{1-8}$ alkyl or optionally substituted $C_{6-10}$ aryl;

$R^{10}$ is hydrogen, optionally substituted $C_{1-8}$ alkyl or optionally substituted $C_{6-10}$ aryl;

$R^{9a}$ is hydrogen, optionally substituted $C_{1-8}$ alkyl or optionally substituted $C_{6-10}$ aryl;

$R^{10a}$ is hydrogen, optionally substituted $C_{1-8}$ alkyl or optionally substituted $C_{6-10}$ aryl;

$R^{11}$ is hydrogen or optionally substituted $C_{1-8}$ alkyl;
$R^{12}$ is hydrogen or optionally substituted $C_{1-8}$ alkyl;
$R^{13}$ is hydrogen or optionally substituted $C_{1-8}$ alkyl;
$R^{14}$ is hydrogen, CF$_3$ or optionally substituted $C_{1-8}$ alkyl;
$R^{15}$ is hydrogen or optionally substituted $C_{1-8}$ alkyl; and
the compound of Formula II is not of structure:

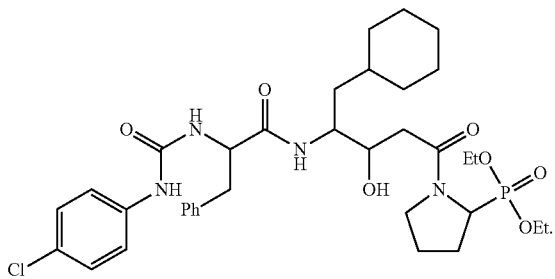 [SMILES: CCOP(=O)(OCC)C1CCCN1C(=O)CC(O)C(CC1CCCCC1)NC(=O)C(Cc1ccccc1)NC(=O)Nc1ccc(Cl)cc1]

In another aspect, the invention provides a compound represented by Formula II,
wherein
a is 0 and b is 1;
$R^1$ is —OR$^{13}$;
$R^2$ is optionally substituted $C_{1-8}$ alkyl or optionally substituted $C_{6-10}$ aryl;
$R^3$ is hydrogen, optionally substituted $C_{1-8}$ alkyl, halogen, —COOR$^{15}$, —OR$^{13}$, —NR$^{11}$R$^{12}$, NO$_2$, optionally substituted heterocycle, optionally substituted $C_{3-8}$ cycloalkyl, optionally substituted $C_{6-10}$ aryl or optionally substituted $C_{3-8}$ cycloalkenyl;
$R^4$ is hydrogen, optionally substituted $C_{1-8}$ alkyl, halogen, —COOR$^{15}$, —OR$^{13}$, —NR$^{11}$R$^{12}$, NO$_2$, optionally substituted heterocycle, optionally substituted $C_{3-8}$ cycloalkyl, optionally substituted $C_{6-10}$ aryl or optionally substituted $C_{3-8}$ cycloalkenyl;
$R^5$ is halogen;
$R^6$ is hydrogen, optionally substituted $C_{1-8}$ alkyl, halogen, —COOR$^{15}$, —OR$^{13}$, —NR$^{11}$R$^{12}$, NO$_2$, optionally substituted heterocycle, optionally substituted $C_{3-8}$ cycloalkyl, optionally substituted $C_{6-10}$ aryl or optionally substituted $C_{3-8}$ cycloalkenyl;
$R^7$ is hydrogen, optionally substituted $C_{1-8}$ alkyl, halogen, —COOR$^{15}$, —OR$^{13}$, —NR$^{11}$R$^{12}$, NO$_2$, optionally substituted heterocycle, optionally substituted $C_{3-8}$ cycloalkyl, optionally substituted $C_{6-10}$ aryl or optionally substituted $C_{3-8}$ cycloalkenyl;
$R^8$ is hydrogen, optionally substituted $C_{1-8}$ alkyl or optionally substituted $C_{6-10}$ aryl;
$R^9$ is hydrogen, optionally substituted $C_{1-8}$ alkyl or optionally substituted $C_{6-10}$ aryl;
$R^{10}$ is hydrogen, optionally substituted $C_{1-8}$ alkyl or optionally substituted $C_{6-10}$ aryl;
$R^{9a}$ is hydrogen, optionally substituted $C_{1-8}$ alkyl or optionally substituted $C_{6-10}$ aryl;
$R^{10a}$ is hydrogen, optionally substituted $C_{1-8}$ alkyl or optionally substituted $C_{6-10}$ aryl;
$R^{11}$ is hydrogen or optionally substituted $C_{1-8}$ alkyl;
$R^{12}$ is hydrogen or optionally substituted $C_{1-8}$ alkyl;
$R^{13}$ is hydrogen or optionally substituted $C_{1-8}$ alkyl;
$R^{15}$ is hydrogen or optionally substituted $C_{1-8}$ alkyl; and
the compound of Formula II is not of structure:

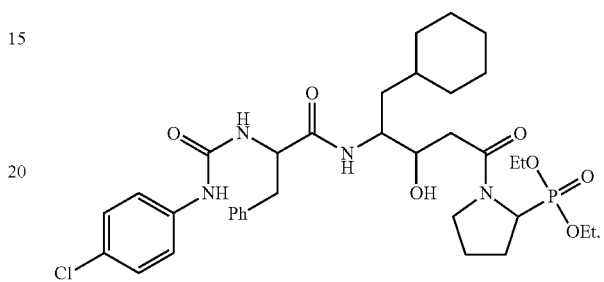

In another aspect, the invention provides a compound represented by Formula II,
wherein:
a is 0 and b is 1;
$R^1$ is —OR$^{13}$;
$R^2$ is optionally substituted $C_{1-8}$ alkyl;
$R^3$ is hydrogen, optionally substituted $C_{1-8}$ alkyl, halogen;
$R^4$ is hydrogen, optionally substituted $C_{1-8}$ alkyl, halogen;
$R^5$ is halogen, —CF$_3$ or —S(O)$_n$R$^{14}$;
n is 0, 1 or 2;
$R^6$ is hydrogen, optionally substituted $C_{1-8}$ alkyl, halogen;
$R^7$ is hydrogen, optionally substituted $C_{1-8}$ alkyl, halogen;
$R^8$ is hydrogen;
$R^9$ is hydrogen;
$R^{10}$ is hydrogen, optionally substituted $C_{1-8}$ alkyl;
$R^{9a}$ is hydrogen, optionally substituted $C_{1-8}$ alkyl;
$R^{10a}$ is hydrogen, optionally substituted $C_{1-8}$ alkyl;
$R^{13}$ is hydrogen or optionally substituted $C_{1-8}$ alkyl; and
$R^{14}$ is hydrogen, CF$_3$ or optionally substituted $C_{1-8}$ alkyl; and
the compound of Formula II is not of structure:

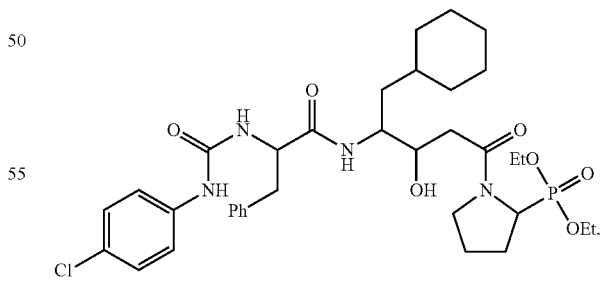

In another aspect, the invention provides a compound represented by Formula II,
wherein:
a is 0 and b is 1;
$R^1$ is —OR$^{13}$;
$R^2$ is optionally substituted $C_{1-8}$ alkyl;
$R^3$ is hydrogen or halogen;

$R^4$ is hydrogen;
$R^5$ is halogen;
$R^6$ is hydrogen;
$R^7$ is hydrogen;
$R^8$ is hydrogen;
$R^9$ is hydrogen;
$R^{10}$ is hydrogen or optionally substituted $C_{1-8}$ alkyl;
$R^{9a}$ is hydrogen or optionally substituted $C_{1-8}$ alkyl;
$R^{10a}$ is hydrogen or optionally substituted $C_{1-8}$ alkyl; and
$R^{13}$ is hydrogen; and
the compound of Formula II is not of structure:

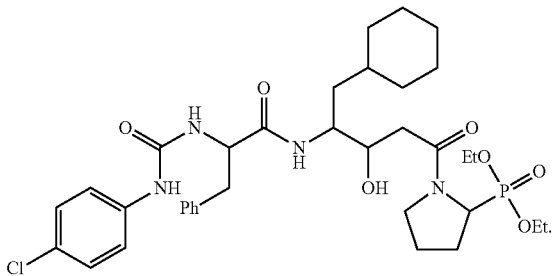 [SMILES: CCOP(=O)(OCC)C1CCCN1C(=O)CC(O)C(CC1CCCCC1)NC(=O)C(Cc1ccccc1)NC(=O)Nc1ccc(Cl)cc1]

In another aspect, the invention provides a compound represented by Formula II,
wherein:
a is 0 and b is 1;
$R^1$ is —$OR^{13}$;
$R^2$ is optionally substituted $C_{1-8}$ alkyl;
$R^3$ is hydrogen or halogen;
$R^4$ is hydrogen;
$R^5$ is halogen;
$R^6$ is hydrogen;
$R^7$ is hydrogen;
$R^8$ is hydrogen;
$R^9$ is hydrogen;
$R^{10}$ is hydrogen or optionally substituted $C_{1-8}$ alkyl;
$R^{9a}$ is optionally substituted $C_{1-8}$ alkyl;
$R^{10a}$ is optionally substituted $C_{1-8}$ alkyl; and
$R^{13}$ is hydrogen.

In another aspect, the invention provides a compound represented by Formula II,
wherein
a is 1 and b is 1;
$R^1$ is optionally substituted $C_{1-8}$ alkyl, optionally substituted $C_{3-8}$ cycloalkyl, optionally substituted heterocycle, optionally substituted $C_{3-8}$ cycloalkyl, optionally substituted $C_{6-10}$ aryl, optionally substituted $C_{3-8}$ cycloalkenyl, —$NR^{11}R^{12}$ or —$OR^{13}$;
$R^2$ is optionally substituted $C_{1-8}$ alkyl or optionally substituted $C_{6-10}$ aryl;
$R^3$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^4$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^5$ is halogen, —$CF_3$ or —$S(O)_nR^{14}$;
n is 0, 1 or 2;
$R^6$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^7$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^8$ is hydrogen, optionally substituted $C_{1-8}$ alkyl or optionally substituted $C_{6-10}$ aryl;
$R^9$ is hydrogen, optionally substituted $C_{1-8}$ alkyl or optionally substituted $C_{6-10}$ aryl;
$R^{10}$ is hydrogen, optionally substituted $C_{1-8}$ alkyl or optionally substituted $C_{6-10}$ aryl;
$R^{9a}$ is hydrogen, optionally substituted $C_{1-8}$ alkyl or optionally substituted $C_{6-10}$ aryl;
$R^{10a}$ is hydrogen, optionally substituted $C_{1-8}$ alkyl or optionally substituted $C_{6-10}$ aryl;
$R^{11}$ is hydrogen or optionally substituted $C_{1-8}$ alkyl;
$R^{12}$ is hydrogen or optionally substituted $C_{1-8}$ alkyl;
$R^{13}$ is hydrogen or optionally substituted $C_{1-8}$ alkyl;
$R^{14}$ is hydrogen or optionally substituted $C_{1-8}$ alkyl; and
$R^{15}$ is hydrogen or optionally substituted $C_{1-8}$ alkyl; and
with the proviso:
that $R^{11}$ is not:

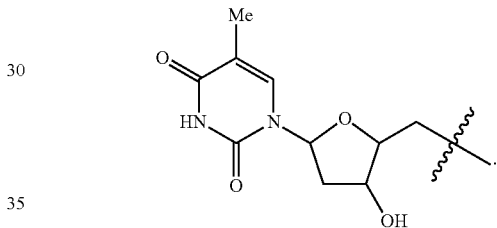

In another aspect, the invention provides a compound represented by Formula II,
wherein
a is 1 and b is 1;
$R^1$ is optionally substituted $C_{1-8}$ alkyl, optionally substituted $C_{3-8}$ cycloalkyl, optionally substituted heterocycle, optionally substituted $C_{3-8}$ cycloalkyl, optionally substituted $C_{6-10}$ aryl, optionally substituted $C_{3-8}$ cycloalkenyl, —$NR^{11}R^{12}$ or —$OR^{13}$;
$R^2$ is optionally substituted $C_{1-8}$ alkyl or optionally substituted $C_{6-10}$ aryl;
$R^3$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^4$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^5$ is halogen;
$R^6$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^7$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;
$R^8$ is hydrogen, optionally substituted $C_{1-8}$ alkyl or optionally substituted $C_{6-10}$ aryl;
$R^9$ is hydrogen, optionally substituted $C_{1-8}$ alkyl or optionally substituted $C_{6-10}$ aryl;
$R^{10}$ is hydrogen, optionally substituted $C_{1-8}$ alkyl or optionally substituted $C_{6-10}$ aryl;
$R^{9a}$ is hydrogen, optionally substituted $C_{1-8}$ alkyl or optionally substituted $C_{6-10}$ aryl;
$R^{10a}$ is hydrogen, optionally substituted $C_{1-8}$ alkyl or optionally substituted $C_{6-10}$ aryl;
$R^{11}$ is hydrogen or optionally substituted $C_{1-8}$ alkyl;
$R^{12}$ is hydrogen or optionally substituted $C_{1-8}$ alkyl;
$R^{13}$ is hydrogen or optionally substituted $C_{1-8}$ alkyl;
$R^{15}$ is hydrogen or optionally substituted $C_{1-8}$ alkyl; and
with the proviso:
that $R^{11}$ is not:

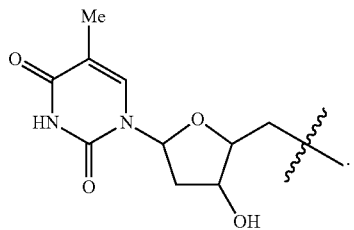 [SMILES: *CC1OC(n2cc(C)c(=O)[nH]c2=O)CC1O]

In another aspect, the invention provides a compound represented by Formula II,
wherein
a is 1 and b is 1;
$R^1$ is optionally substituted $C_{1-8}$ alkyl, —$NR^{11}R^{12}$ or —$OR^{13}$;
$R^2$ is optionally substituted $C_{1-8}$ alkyl or optionally substituted $C_{6-10}$ aryl;
$R^3$ is hydrogen, optionally substituted $C_{1-8}$ alkyl, halogen;
$R^4$ is hydrogen, optionally substituted $C_{1-8}$ alkyl, halogen;
$R^5$ is halogen, —$CF_3$ or —$S(O)_NR^{14}$;
n is 0, 1 or 2;
$R^6$ is hydrogen, optionally substituted $C_{1-8}$ alkyl, halogen;
$R^7$ is hydrogen, optionally substituted $C_{1-8}$ alkyl, halogen;
$R^8$ is hydrogen;
$R^9$ is hydrogen, optionally substituted $C_{1-8}$ alkyl;
$R^{10}$ is hydrogen, optionally substituted $C_{1-8}$ alkyl;
$R^{9a}$ is hydrogen, optionally substituted $C_{1-8}$ alkyl;
$R^{10A}$ is hydrogen, optionally substituted $C_{1-8}$ alkyl;
$R^{11}$ is hydrogen or optionally substituted $C_{1-8}$ alkyl;
$R^{12}$ is hydrogen or optionally substituted $C_{1-8}$ alkyl;
$R^{13}$ is hydrogen or optionally substituted $C_{1-8}$ alkyl;
$R^{14}$ is hydrogen or optionally substituted $C_{1-8}$ alkyl; and
$R^{15}$ is hydrogen or optionally substituted $C_{1-8}$ alkyl;
with the proviso:
that $R^{11}$ is not:

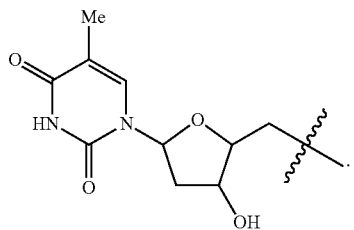 [SMILES: *CC1OC(n2cc(C)c(=O)[nH]c2=O)CC1O]

In another aspect, the invention provides a compound represented by Formula II,
wherein
a is 1 and b is 1;
$R^1$ is —$OR^{13}$;
$R^2$ is optionally substituted $C_{1-8}$ alkyl or optionally substituted $C_{6-10}$ aryl;
$R^3$ is hydrogen;
$R^4$ is hydrogen;
$R^5$ is halogen;
$R^6$ is hydrogen;
$R^7$ is hydrogen;
$R^8$ is hydrogen;
$R^9$ is hydrogen;
$R^{10}$ is hydrogen;
$R^{9a}$ is hydrogen;
$R^{10a}$ is hydrogen; and
$R^{13}$ is hydrogen or optionally substituted $C_{1-8}$ alkyl; and
with the proviso:
that $R^{11}$ is not:

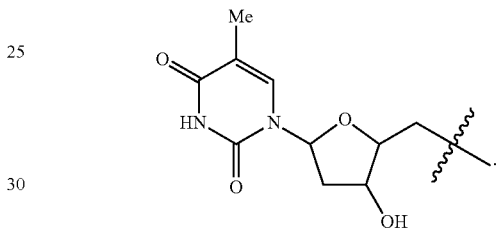

The term "alkyl", as used herein, refers to saturated, monovalent or divalent hydrocarbon moieties having linear or branched moieties or combinations thereof and containing 1 to 8 carbon atoms. One methylene (—$CH_2$—) group, of the alkyl group can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkyl groups can have one or more chiral centers. Alkyl groups can be independently substituted by halogen atoms, hydroxyl groups, cycloalkyl groups, amino groups, heterocyclic groups, aryl groups, carboxylic acid groups, phosphonic acid groups, sulphonic acid groups, phosphoric acid groups, nitro groups, amide groups, sulfonamide groups.

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted by halogen atoms, sulfonyl $C_{1-8}$ alkyl groups, sulfoxide $C_{1-8}$ alkyl groups, sulfonamide groups, nitro groups, cyano groups, —$OC_{1-8}$ alkyl groups, —$SC_{1-8}$ alkyl groups, —$C_{1-8}$ alkyl groups, —$C_{2-6}$ alkenyl groups, —$C_{2-6}$ alkynyl groups, ketone groups, alkylamino groups, amino groups, aryl groups, $C_{3-8}$ cycloalkyl groups or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted by halogen atoms, sulfonyl groups, sulfoxide groups, nitro groups, cyano groups, —$OC_{1-6}$ alkyl groups, —$SC_{1-6}$ alkyl groups, —$C_{1-6}$ alkyl groups, —$C_{2-6}$ alkenyl groups, —$C_{2-6}$ alkynyl groups, ketone groups, alkylamino groups, amino groups, aryl groups, $C_{3-8}$ cycloalkyl groups or hydroxyl groups.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. One methylene (—CH$_2$—) group, of the alkenyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. $C_{2-6}$ alkenyl can be in the E or Z configuration. Alkenyl groups can be substituted by alkyl groups, as defined above or by halogen atoms.

The term "alkynyl", as used herein, refers to a monovalent or divalent hydrocarbon radical having 2 to 6 carbon atoms, derived from a saturated alkyl, having at least one triple bond. One methylene (—CH$_2$—) group, of the alkynyl can be replaced by oxygen, sulfur, sulfoxide, nitrogen, carbonyl, carboxyl, sulfonyl, sulfate, sulfonate, amide, sulfonamide, by a divalent $C_{3-8}$ cycloalkyl, by a divalent heterocycle, or by a divalent aryl group. Alkynyl groups can be substituted by alkyl groups, as defined above, or by halogen atoms.

The term "heterocycle" as used herein, refers to a 3 to 10 membered ring, which can be aromatic or non-aromatic, saturated or unsaturated, containing at least one heteroatom selected form oxygen, nitrogen, sulfur, or combinations of at least two thereof, interrupting the carbocyclic ring structure. The heterocyclic ring can be interrupted by a C=O; the S and N heteroatoms can be oxidized. Heterocycles can be monocyclic or polycyclic. Heterocyclic ring moieties can be substituted by halogen atoms, sulfonyl groups, sulfoxide groups, nitro groups, cyano groups, —OC$_{1-6}$ alkyl groups, —SC$_{1-6}$ alkyl groups, —C$_{1-8}$ alkyl groups, —C$_{2-6}$ alkenyl groups, —C$_{2-6}$ alkynyl groups, ketone groups, alkylamino groups, amino groups, aryl groups, $C_{3-8}$ cycloalkyl groups or hydroxyl groups.

The term "aryl" as used herein, refers to an organic moiety derived from an aromatic hydrocarbon consisting of a ring containing 6 to 10 carbon atoms, by removal of one hydrogen atom. Aryl can be substituted by halogen atoms, sulfonyl C$_{1-6}$ alkyl groups, sulfoxide C$_{1-6}$ alkyl groups, sulfonamide groups, carboxylic acid groups, C$_{1-6}$ alkyl carboxylates (ester) groups, amide groups, nitro groups, cyano groups, —OC$_{1-6}$ alkyl groups, —SC$_{1-6}$ alkyl groups, —C$_{1-6}$ alkyl groups, —C$_{2-6}$ alkenyl groups, —C$_{2-6}$ alkynyl groups, ketone groups, aldehydes, alkylamino groups, amino groups, aryl groups, $C_{3-8}$ cycloalkyl groups or hydroxyl groups. Aryls can be monocyclic or polycyclic.

The term "hydroxyl" as used herein, represents a group of formula "—OH".

The term "carbonyl" as used herein, represents a group of formula "—C(O)—".

The term "ketone" as used herein, represents an organic compound having a carbonyl group linked to a carbon atom such as —(CO)R$^x$ wherein R$^x$ can be alkyl, aryl, cycloalkyl, cycloalkenyl, heterocycle as defined above.

The term "amine" as used herein, represents a group of formula "—NR$^x$R$^y$", wherein R$^x$ and R$^y$ can be the same or independently H, alkyl, aryl, cycloalkyl, cycloalkenyl, heterocycle as defined above.

The term "carboxyl" as used herein, represents a group of formula "—C(O)O—".

The term "sulfonyl" as used herein, represents a group of formula "—SO$_2$—".

The term "sulfate" as used herein, represents a group of formula "—O—S(O)$_2$—O—".

The term "sulfonate" as used herein, represents a group of the formula "—S(O)$_2$—O—".

The term "carboxylic acid" as used herein, represents a group of formula "—C(O)OH".

The term "nitro" as used herein, represents a group of formula "—NO$_2$".

The term "cyano" as used herein, represents a group of formula "—CN".

The term "amide" as used herein, represents a group of formula "—C(O)NR$^x$R$^y$," wherein R$^x$ and R$^y$ can be the same or independently H, alkyl, aryl, cycloalkyl, cycloalkenyl, heterocycle as defined above.

The term "sulfonamide" as used herein, represents a group of formula "—S(O)$_2$NR$^x$R$^y$" wherein R$^x$ and R$^y$ can be the same or independently H, alkyl, aryl, cycloalkyl, cycloalkenyl, heterocycle as defined above.

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—OP(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

The invention discloses compounds
{2-{[(4-bromophenyl)carbamoyl]amino}-3-(1H-indol-3-yl)propanoyl]amino}acetic acid;
tert-butyl {2-{[(4-bromophenyl)carbamoyl]amino}-3-(1H-indol-3-yl)propanoyl]amino}acetate;
[(4-amino-2-{[(4-bromophenyl)carbamoyl]amino}-4-oxobutanoyl)amino]acetic acid;
tert-butyl [(4-amino-2-{[(4-bromophenyl)carbamoyl]amino}-4-oxobutanoyl)amino]acetate;
2-{[(2R)-2-{[(4-bromophenyl)carbamoyl]amino}-4-methylpentanoyl]amino}-2-methylpropanoic acid;
tert-butyl 2-{[(2R)-2-{[(4-bromophenyl)carbamoyl]amino}-4-methylpentanoyl]amino}-2-methylpropanoate;
{2-{[(4-bromophenyl)carbamoyl]amino}-3-(1H-imidazol-4-yl)propanoyl]amino}acetic acid;
tert-butyl {2-{[(4-bromophenyl)carbamoyl]amino}-3-(1H-imidazol-4-yl)propanoyl]amino}acetate;
{[(2S)-2-{[(4-bromophenyl)carbamoyl]amino}-4-(methylsulfonyl)butanoyl]amino}acetic acid;
tert-butyl {[(2S)-2-{[(4-bromophenyl)carbamoyl]amino}-4-(methylsulfonyl)butanoyl]amino}acetate;
{[(2S)-2-{[(4-bromophenyl)carbamoyl]amino}-4-(methylsulfanyl)butanoyl]amino}acetic acid;
tert-butyl {[(2S)-2-{[(4-bromophenyl)carbamoyl]amino}-4-(methylsulfanyl)butanoyl]amino}acetate;
2-methyl-2-{[(2S)-4-methyl-2-({[4-(trifluoromethyl)phenyl]carbamoyl}amino)pentanoyl]amino}propanoic acid;
tert-butyl 2-methyl-2-{[(2S)-4-methyl-2-({[4-(trifluoromethyl)phenyl]carbamoyl}amino)pentanoyl]amino}propanoate;
{[(2S)-4-methyl-2-({[4-(methylsulfonyl)phenyl]carbamoyl}amino)pentanoyl]amino}acetic acid;
tert-butyl {[(2S)-4-methyl-2-({[4-(methylsulfonyl)phenyl]carbamoyl}amino)pentanoyl]amino}acetate;

{[(2S)-4-methyl-2-({[4-(methylsulfinyl)phenyl] carbamoyl}amino)pentanoyl]amino}acetic acid;

tert-butyl {[(2S)-4-methyl-2-({[4-(methylsulfinyl)phenyl] carbamoyl}amino)pentanoyl]amino}acetate;

2-{[(2S)-2-{[(4-bromophenyl)carbamoyl]amino}-4-methylpentanoyl]amino}-2-methylpropanoic acid;

tert-butyl 2-{[(2S)-2-{[(4-bromophenyl)carbamoyl]amino}-4-methylpentanoyl]amino}-2-methylpropanoate;

({(2S)-4-methyl-2-[({4-[(trifluoromethyl)sulfanyl] phenyl}carbamoyl)amino]pentanoyl}amino)acetic acid;

tert-butyl ({(2S)-4-methyl-2-[({4-[(trifluoromethyl)sulfanyl]phenyl}carbamoyl)amino]pentanoyl}amino)acetate;

{[(2S)-4-methyl-2-({[4-(methylsulfanyl)phenyl] carbamoyl}amino)pentanoyl]amino}acetic acid;

tert-butyl {[(2S)-4-methyl-2-({[4-(methylsulfanyl)phenyl] carbamoyl}amino)pentanoyl]amino}acetate;

{[(2R)-2-{[(4-bromophenyl)carbamoyl]amino}-4-methylpentanoyl]amino}acetic acid;

tert-butyl {[(2R)-2-{[(4-bromophenyl)carbamoyl]amino}-4-methylpentanoyl]amino}acetate;

{[(2R,3R)-2-{[(4-bromophenyl)carbamoyl]amino}-3-methylpentanoyl]amino}acetic acid tert-butyl {[(2R,3R)-2-{[(4-bromophenyl)carbamoyl]amino}-3-methylpentanoyl] amino}acetate;

{[(2S)-4-methyl-2-({[4-(trifluoromethyl)phenyl] carbamoyl}amino)pentanoyl]amino}acetic acid;

tert-butyl {[(2S)-4-methyl-2-({[4-(trifluoromethyl)phenyl] carbamoyl}amino)pentanoyl]amino}acetate;

{[(2R)-2-{[(4-bromo-2-fluorophenyl)carbamoyl]amino}-4-methylpentanoyl]amino}acetic acid;

(2S)-2-{[(4-bromophenyl)carbamoyl]amino}-N-[2-(dimethylamino)-2-oxoethyl]-4-methylpentanamide;

[(2-{[(4-bromophenyl)carbamoyl]amino}-2-methylpropanoyl)amino]acetic acid;

tert-butyl [(2-{[(4-bromophenyl)carbamoyl]amino}-2-methylpropanoyl)amino]acetate;

[(2-{[(4-bromophenyl)carbamoyl]amino}-2-ethylbutanoyl) amino]acetic acid;

tert-butyl [(2-{[(4-bromophenyl)carbamoyl]amino}-2-ethylbutanoyl)amino]acetate;

[(2-{[(4-bromophenyl)carbamoyl]amino}-2,4-dimethylpentanoyl)amino]acetic acid;

tert-butyl [(2-{[(4-bromophenyl)carbamoyl]amino}-2,4-dimethylpentanoyl)amino]acetate;

(2S)—N-[(1S)-2-amino-2-oxo-1-phenylethyl]-2-{[(4-bromophenyl)carbamoyl]amino}-4-methylpentanamide;

(2S)-{[(2S)-2-{[(4-bromophenyl)carbamoyl]amino}-4-methylpentanoyl]amino}(phenyl)ethanoic acid;

tert-butyl (2S)-{[(2S)-2-{[(4-bromophenyl)carbamoyl] amino}-4-methylpentanoyl]amino}(phenyl)ethanoate;

(2S)—N-[(2S)-1-amino-1-oxopentan-2-yl]-2-{[(4-bromophenyl)carbamoyl]amino}-4-methylpentanamide;

(2S)-2-{[(2S)-2-{[(4-bromophenyl)carbamoyl]amino}-4-methylpentanoyl]amino}pentanoic acid;

tert-butyl (2S)-2-{[(2S)-2-{[(4-bromophenyl)carbamoyl] amino}-4-methylpentanoyl]amino}pentanoate;

(2S)-2-{[(4-bromophenyl)carbamoyl]amino}-N-[(2R)-1-hydroxypropan-2-yl]-4-methylpentanamide;

(2S)-2-{[(4-bromophenyl)carbamoyl]amino}-N-(2,3-dihydroxypropyl)-4-methylpentanamide;

(2S)-2-{[(4-bromophenyl)carbamoyl]amino}-N-(1,3-dihydroxypropan-2-yl)-4-methylpentanamide;

(2S)-2-{[(4-bromophenyl)carbamoyl]amino}-N-(2-hydroxy-2-methylpropyl)-4-methylpentanamide;

(2S)—N-[(2S)-1-amino-3-methyl-1-oxobutan-2-yl]-2-{[(4-bromophenyl)carbamoyl]amino}-4-methylpentanamide;

(2S)-2-{[(2S)-2-{[(4-bromophenyl)carbamoyl]amino}-4-methylpentanoyl]amino}-3-methylbutanoic acid;

tert-butyl (2S)-2-{[(2S)-2-{[(4-bromophenyl)carbamoyl] amino}-4-methylpentanoyl]amino}-3-methylbutanoate;

(2S)—N-[(2S)-1-amino-1-oxopropan-2-yl]-2-{[(4-bromophenyl)carbamoyl]amino}-4-methylpentanamide;

(2S)-2-{[(2S)-2-{[(4-bromophenyl)carbamoyl]amino}-4-methylpentanoyl]amino}propanoic acid;

tert-butyl (2S)-2-{[(2S)-2-{[(4-bromophenyl)carbamoyl] amino}-4-methylpentanoyl]amino}propanoate;

(2S)—N-[(2S)-1-amino-1-oxopropan-2-yl]-2-{[(4-bromo-2-fluorophenyl)carbamoyl]amino}-4-methylpentanamide;

(2S)-2-{[(2S)-2-{[(4-bromo-2-fluorophenyl)carbamoyl] amino}-4-methylpentanoyl]amino}propanoic acid;

tert-butyl (2S)-2-{[(2S)-2-{[(4-bromo-2-fluorophenyl)carbamoyl]amino}-4-methylpentanoyl]amino}propanoate;

(2S)-2-{[(4-bromo-2-fluorophenyl)carbamoyl]amino}-N-(2-hydroxyethyl)-4-methylpentanamide;

(2S)-2-{[(4-bromo-2-fluorophenyl)carbamoyl]amino}-4-methyl-N-(2-oxopropyl)pentanamide;

(2S)—N-(2-amino-2-oxoethyl)-2-{[(4-bromo-2-fluorophenyl)carbamoyl]amino}-4-methylpentanamide;

{[(2S)-2-{[(4-bromo-2-fluorophenyl)carbamoyl]amino}-4-methylpentanoyl]amino}acetic acid;

tert-butyl {[(2S)-2-{[(4-bromo-2-fluorophenyl)carbamoyl] amino}-4-methylpentanoyl]amino}acetate;

(2S)—N-(2-amino-2-oxoethyl)-2-{[(4-bromo-2-fluorophenyl)carbamoyl]amino}pentanamide;

(2S)—N-(2-amino-2-oxoethyl)-2-{[(4-bromophenyl)carbamoyl]amino}pentanamide;

(2S)-2-{[(4-bromophenyl)carbamoyl]amino}-4-methyl-N-(2-oxopropyl)pentanamide;

(2S)—N-(2-amino-2-oxoethyl)-2-{[(4-bromophenyl)carbamoyl]amino}-4-methylpentanamide;

{[(2S)-2-{[(4-bromophenyl)carbamoyl]amino}-4-methylpentanoyl]amino}acetic acid;

(2S)-2-{[(4-bromophenyl)carbamoyl]amino}-N-(2-hydroxyethyl)-4-methylpentanamide;

tert-butyl {[(2S)-2-{[(4-bromophenyl)carbamoyl]amino}-4-methylpentanoyl]amino}acetate;

{[(2S)-2-{[(4-bromo-2-fluorophenyl)carbamoyl] amino}pentanoyl]amino}acetic acid;

tert-butyl {[(2S)-2-{[(4-bromo-2-fluorophenyl)carbamoyl] amino}pentanoyl]amino}acetate;

(2S)-2-{[(4-bromo-2-fluorophenyl)carbamoyl]amino}-N-(2-oxopropyl)pentanamide;

(2S)-2-{[(4-bromophenyl)carbamoyl]amino}-N-(2-oxopropyl)pentanamide;

propan-2-yl {[(2S)-2-{[(4-bromophenyl)carbamoyl] amino}pentanoyl]amino}acetate;

ethyl {[(2S)-2-{[(4-bromophenyl)carbamoyl] amino}pentanoyl]amino}acetate;

methyl {[(2S)-2-{[(4-bromophenyl)carbamoyl] amino}pentanoyl]amino}acetate;

(2S)-2-{[(4-bromo-2-fluorophenyl)carbamoyl]amino}-N-(2-hydroxyethyl)pentanamide;

(2S)-2-{[(4-bromophenyl)carbamoyl]amino}-N-(2-hydroxyethyl)pentanamide;

(2S)-2-{[(4-bromo-2-fluorophenyl)carbamoyl]amino}-N-(2-hydroxyethyl)-3-phenylpropanamide;

{[(2S)-2-{[(4-bromophenyl)carbamoyl]amino}pentanoyl] amino}acetic acid;

tert-butyl {[(2S)-2-{[(4-bromophenyl)carbamoyl] amino}pentanoyl]amino}acetate;

(2S)-2-{[(4-bromo-2-fluorophenyl)carbamoyl]amino}-N-(2-oxopropyl)-3-phenylpropanamide;

(2S)-2-{[(4-bromophenyl)carbamoyl]amino}-N-(2-oxopropyl)-3-phenylpropanamide;
(2S,3S)-2-{[(4-bromo-2-fluorophenyl)carbamoyl]amino}-N-(2-hydroxyethyl)-3-methylpentanamide;
(2S,3S)-2-{[(4-bromophenyl)carbamoyl]amino}-N-(2-hydroxyethyl)-3-methylpentanamide;
(2S,3S)-2-{[(4-bromo-2-fluorophenyl)carbamoyl]amino}-3-methyl-N-(2-oxopropyl)pentanamide;
(2S,3S)-2-{[(4-bromophenyl)carbamoyl]amino}-3-methyl-N-(2-oxopropyl)pentanamide;
(2S,3S)—N-(2-amino-2-oxoethyl)-2-{[(4-bromo-2-fluorophenyl)carbamoyl]amino}-3-methylpentanamide;
(2S,3S)—N-(2-amino-2-oxoethyl)-2-{[(4-bromophenyl)carbamoyl]amino}-3-methylpentanamide;
{[(2S,3S)-2-{[(4-bromophenyl)carbamoyl]amino}-3-methylpentanoyl]amino}acetic acid;
tert-butyl {[(2S,3S)-2-{[(4-bromophenyl)carbamoyl]amino}-3-methylpentanoyl]amino}acetate;
{[(2S,3S)-2-{[(4-bromo-2-fluorophenyl)carbamoyl]amino}-3-methylpentanoyl]amino}acetic acid;
tert-butyl {[(2S,3S)-2-{[(4-bromo-2-fluorophenyl)carbamoyl]amino}-3-methylpentanoyl]amino}acetate;
(2S)-2-{[(4-bromophenyl)carbamoyl]amino}-N-(2-hydroxyethyl)-3-phenylpropanamide;
3-{[(2S)-2-{[(4-bromophenyl)carbamoyl]amino}-3-phenylpropanoyl]amino}propanoic acid;
tert-butyl 3-{[(2S)-2-{[(4-bromophenyl)carbamoyl]amino}-3-phenylpropanoyl]amino}propanoate;
{[(2S)-2-{[(4-bromophenyl)carbamoyl]amino}-3-phenylpropanoyl]amino}acetic acid;
tert-butyl {[(2S)-2-{[(4-bromophenyl)carbamoyl]amino}-3-phenylpropanoyl]amino}acetate.

In another aspect the invention discloses compounds:
{[2-{[(4-bromophenyl)carbamoyl]amino}-3-(1H-imidazol-4-yl)propanoyl]amino}acetic acid;
tert-butyl {[2-{[(4-bromophenyl)carbamoyl]amino}-3-(1H-imidazol-4-yl)propanoyl]amino}acetate;
{[(2S)-2-{[(4-bromophenyl)carbamoyl]amino}-4-(methylsulfonyl)butanoyl]amino}acetic acid;
tert-butyl {[(2S)-2-{[(4-bromophenyl)carbamoyl]amino}-4-(methylsulfonyl)butanoyl]amino}acetate;
{[(2S)-2-{[(4-bromophenyl)carbamoyl]amino}-4-(methylsulfanyl)butanoyl]amino}acetic acid;
tert-butyl {[(2S)-2-{[(4-bromophenyl)carbamoyl]amino}-4-(methylsulfanyl)butanoyl]amino}acetate;
2-methyl-2-{[(2S)-4-methyl-2-({[4-(trifluoromethyl)phenyl]carbamoyl}amino)pentanoyl]amino}propanoic acid;
tert-butyl 2-methyl-2-{[(2S)-4-methyl-2-({[4-(trifluoromethyl)phenyl]carbamoyl}amino)pentanoyl]amino}propanoate;
{[(2S)-4-methyl-2-({[4-(methylsulfonyl)phenyl]carbamoyl}amino)pentanoyl]amino}acetic acid;
tert-butyl {[(2S)-4-methyl-2-({[4-(methylsulfonyl)phenyl]carbamoyl}amino)pentanoyl]amino}acetate;
{[(2S)-4-methyl-2-({[4-(methylsulfinyl)phenyl]carbamoyl}amino)pentanoyl]amino}acetic acid;
tert-butyl {[(2S)-4-methyl-2-({[4-(methylsulfinyl)phenyl]carbamoyl}amino)pentanoyl]amino}acetate;
2-{[(2S)-2-{[(4-bromophenyl)carbamoyl]amino}-4-methylpentanoyl]amino}-2-methylpropanoic acid;
tert-butyl 2-{[(2S)-2-{[(4-bromophenyl)carbamoyl]amino}-4-methylpentanoyl]amino}-2-methylpropanoate;
({(2S)-4-methyl-2-[({4-[(trifluoromethyl)sulfanyl]phenyl}carbamoyl)amino]pentanoyl}amino)acetic acid;
tert-butyl ({(2S)-4-methyl-2-[({4-[(trifluoromethyl)sulfanyl]phenyl}carbamoyl)amino]pentanoyl}amino)acetate;
{[(2S)-4-methyl-2-({[4-(methylsulfanyl)phenyl]carbamoyl}amino)pentanoyl]amino}acetic acid;
tert-butyl {[(2S)-4-methyl-2-({[4-(methylsulfanyl)phenyl]carbamoyl}amino)pentanoyl]amino}acetate;
{[(2R)-2-{[(4-bromophenyl)carbamoyl]amino}-4-methylpentanoyl]amino}acetic acid;
tert-butyl {[(2R)-2-{[(4-bromophenyl)carbamoyl]amino}-4-methylpentanoyl]amino}acetate;
{[(2R,3R)-2-{[(4-bromophenyl)carbamoyl]amino}-3-methylpentanoyl]amino}acetic acid;
tert-butyl {[(2R,3R)-2-{[(4-bromophenyl)carbamoyl]amino}-3-methylpentanoyl]amino}acetate;
{[(2S)-4-methyl-2-({[4-(trifluoromethyl)phenyl]carbamoyl}amino)pentanoyl]amino}acetic acid;
tert-butyl {[(2S)-4-methyl-2-({[4-(trifluoromethyl)phenyl]carbamoyl}amino)pentanoyl]amino}acetate;
(2S)-2-{[(4-bromophenyl)carbamoyl]amino}-N-[2-(dimethylamino)-2-oxoethyl]-4-methylpentanamide;
[(2-{[(4-bromophenyl)carbamoyl]amino}-2-methylpropanoyl)amino]acetic acid;
tert-butyl [(2-{[(4-bromophenyl)carbamoyl]amino}-2-methylpropanoyl)amino]acetate;
[(2-{[(4-bromophenyl)carbamoyl]amino}-2-ethylbutanoyl)amino]acetic acid;
tert-butyl [(2-{[(4-bromophenyl)carbamoyl]amino}-2-ethylbutanoyl)amino]acetate;
[(2-{[(4-bromophenyl)carbamoyl]amino}-2,4-dimethylpentanoyl)amino]acetic acid;
tert-butyl [(2-{[(4-bromophenyl)carbamoyl]amino}-2,4-dimethylpentanoyl)amino]acetate;
(2S)—N-[(1S)-2-amino-2-oxo-1-phenylethyl]-2-{[(4-bromophenyl)carbamoyl]amino}-4-methylpentanamide;
(2S)-{[(2S)-2-{[(4-bromophenyl)carbamoyl]amino}-4-methylpentanoyl]amino}(phenyl)ethanoic acid;
tert-butyl (2S)-{[(2S)-2-{[(4-bromophenyl)carbamoyl]amino}-4-methylpentanoyl]amino}(phenyl)ethanoate;
(2S)—N-[(2S)-1-amino-1-oxopentan-2-yl]-2-{[(4-bromophenyl)carbamoyl]amino}-4-methylpentanamide;
(2S)-2-{[(2S)-2-{[(4-bromophenyl)carbamoyl]amino}-4-methylpentanoyl]amino}pentanoic acid;
tert-butyl (2S)-2-{[(2S)-2-{[(4-bromophenyl)carbamoyl]amino}-4-methylpentanoyl]amino}pentanoate;
(2S)-2-{[(4-bromophenyl)carbamoyl]amino}-N-[(2R)-1-hydroxypropan-2-yl]-4-methylpentanamide;
(2S)-2-{[(4-bromophenyl)carbamoyl]amino}-N-(2,3-dihydroxypropyl)-4-methylpentanamide;
(2S)-2-{[(4-bromophenyl)carbamoyl]amino}-N-(1,3-dihydroxypropan-2-yl)-4-methylpentanamide;
(2S)-2-{[(4-bromophenyl)carbamoyl]amino}-N-(2-hydroxy-2-methylpropyl)-4-methylpentanamide;
(2S)—N-[(2S)-1-amino-3-methyl-1-oxobutan-2-yl]-2-{[(4-bromophenyl)carbamoyl]amino}-4-methylpentanamide;
(2S)-2-{[(2S)-2-{[(4-bromophenyl)carbamoyl]amino}-4-methylpentanoyl]amino}-3-methylbutanoic acid;
tert-butyl (2S)-2-{[(2S)-2-{[(4-bromophenyl)carbamoyl]amino}-4-methylpentanoyl]amino}-3-methylbutanoate;
(2S)—N-[(2S)-1-amino-1-oxopropan-2-yl]-2-{[(4-bromophenyl)carbamoyl]amino}-4-methylpentanamide;
(2S)-2-{[(2S)-2-{[(4-bromophenyl)carbamoyl]amino}-4-methylpentanoyl]amino}propanoic acid;
tert-butyl (2S)-2-{[(2S)-2-{[(4-bromophenyl)carbamoyl]amino}-4-methylpentanoyl]amino}propanoate;
(2S)—N-[(2S)-1-amino-1-oxopropan-2-yl]-2-{[(4-bromo-2-fluorophenyl)carbamoyl]amino}-4-methylpentanamide;
(2S)-2-{[(2S)-2-{[(4-bromo-2-fluorophenyl)carbamoyl]amino}-4-methylpentanoyl]amino}propanoic acid;

tert-butyl (2S)-2-{[(2S)-2-{[(4-bromo-2-fluorophenyl)carbamoyl]amino}-4-methylpentanoyl]amino}propanoate;

(2S)-2-{[(4-bromo-2-fluorophenyl)carbamoyl]amino}-N-(2-hydroxyethyl)-4-methylpentanamide;

(2S)-2-{[(4-bromo-2-fluorophenyl)carbamoyl]amino}-4-methyl-N-(2-oxopropyl)pentanamide;

(2S)—N-(2-amino-2-oxoethyl)-2-{[(4-bromo-2-fluorophenyl)carbamoyl]amino}-4-methylpentanamide;

{[(2S)-2-{[(4-bromo-2-fluorophenyl)carbamoyl]amino}-4-methylpentanoyl]amino}acetic acid;

tert-butyl {[(2S)-2-{[(4-bromo-2-fluorophenyl)carbamoyl]amino}-4-methylpentanoyl]amino}acetate;

tert-butyl 2-{[(2R)-2-{[(4-bromophenyl)carbamoyl]amino}-4-methylpentanoyl]amino}-2-methylpropanoate;

2-{[(2R)-2-{[(4-bromophenyl)carbamoyl]amino}-4-methylpentanoyl]amino}-2-methylpropanoic acid;

tert-butyl [(4-amino-2-{[(4-bromophenyl)carbamoyl]amino}-4-oxobutanoyl)amino]acetate;

[(4-amino-2-{[(4-bromophenyl)carbamoyl]amino}-4-oxobutanoyl)amino]acetic acid;

tert-butyl {[2-{[(4-bromophenyl)carbamoyl]amino}-3-(1H-indol-3-yl)propanoyl]amino}acetate;

{[2-{[(4-bromophenyl)carbamoyl]amino}-3-(1H-indol-3-yl)propanoyl]amino}acetic acid.

Some compounds of Formula I and of Formula II and some of their intermediates have at least one asymmetric center in their structure. This asymmetric center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I and of Formula II are able to form.

The acid addition salt form of a compound of Formula I and of Formula II that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahl & Camille G. Wermuth (Eds), Verlag Helvetica Chimica Acta-Zürich, 2002, 329-345).

The base addition salt form of a compound of Formula I and of Formula II that occurs in its acid form can be obtained by treating the acid with an appropriate base such as an inorganic base, for example, sodium hydroxide, magnesium hydroxide, potassium hydroxide, Calcium hydroxide, ammonia and the like; or an organic base such as for example, L-Arginine, ethanolamine, betaine, benzathine, morpholine and the like. (Handbook of Pharmaceutical Salts, P. Heinrich Stahl & Camille G. Wermuth (Eds), Verlag Helvetica Chimica Acta-Zürich, 2002, 329-345).

Compounds of Formula I and of Formula II and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the N-formyl peptide receptor like-1 receptor.

In another embodiment, there are provided pharmaceutical compositions including at least one compound of the invention in a pharmaceutically acceptable carrier.

In a further embodiment of the invention, there are provided methods for treating disorders associated with modulation of the N-formyl peptide receptor like-1 receptor. Such methods can be performed, for example, by administering to a subject in need thereof a pharmaceutical composition containing a therapeutically effective amount of at least one compound of the invention.

Therapeutic utilities of the N-formyl peptide receptor like-1 receptor modulators are ocular inflammatory diseases including, but not limited to, wet and dry age-related macular degeneration (ARMD), uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, uveitis, herpetic keratitis, corneal angiogenesis, lymphangiogenesis, uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, post surgical corneal wound healing, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, rosacea, atopic dermatitis, acne, psoriasis, seborrheic dermatitis, actinic keratoses, viral warts, photoaging, rheumatoid arthritis and related inflammatory disorders, alopecia, glaucoma, branch vein occlusion, Best's vitelliform macular degeneration, retinitis pigmentosa, proliferative vitreoretinopathy (PVR), and any other degenerative disease of either the photoreceptors or the RPE (Perretti, Mauro et al. Pharmacology & Therapeutics 127 (2010) 175-188.)

These compounds are useful for the treatment of mammals, including humans, with a range of conditions and diseases that are alleviated by the N-formyl peptide receptor like-1 receptor modulation: including, but not limited to the treatment of wet and dry age-related macular degeneration (ARMD), diabetic retinopathy (proliferative), retinopathy of prematurity (ROP), diabetic macular edema, uveitis, retinal vein occlusion, cystoids macular edema, glaucoma, branch vein occlusion, Best's vitelliform macular degeneration, retinitis pigmentosa, proliferative vitreoretinopathy (PVR), and any other degenerative disease of either the photoreceptors or the RPE.

In still another embodiment of the invention, there are provided methods for treating disorders associated with modulation of the FPRL-1 receptor. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I and of Formula II or a pharmaceutically acceptable salt thereof, for the manufacture of a medicament for the treatment of ocular inflammatory diseases including, but not limited to, wet and dry age-related macular degeneration (ARMD), uveitis, dry eye, Keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, uveitis, herpetic keratitis, corneal angiogenesis, lymphangiogenesis, uveitis, retinitis, and choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, post surgical corneal wound healing, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, asthma, allergic disorders, inflammation, systemic lupus erythematosus, psoriasis, CNS disorders such as Alzheimer's disease, arthritis, sepsis, inflammatory bowel disease, cachexia, angina pectoris, post-surgical corneal inflammation, blepharitis, MGD, dermal wound healing, burns, rosacea, atopic dermatitis, acne, psoriasis, seborrheic dermatitis, actinic keratoses, viral warts, photoaging, rheumatoid arthritis and related inflammatory disorders, alopecia, glaucoma, branch vein occlusion, Best's vitelliform macular degeneration, retinitis pigmentosa, proliferative vitreoretinopathy (PVR), and any other degenerative disease of either the photoreceptors or the RPE.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of the N-formyl peptide receptor like-1 (FPRL-1) receptor. Thus, in further embodiments of the invention, there are provided methods for treating a disorder associated with modulation of the N-formyl peptide receptor like-1 (FPRL-1) receptor. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. Synthetic Scheme 1 set forth below, illustrates how the compounds according to the invention can be made.

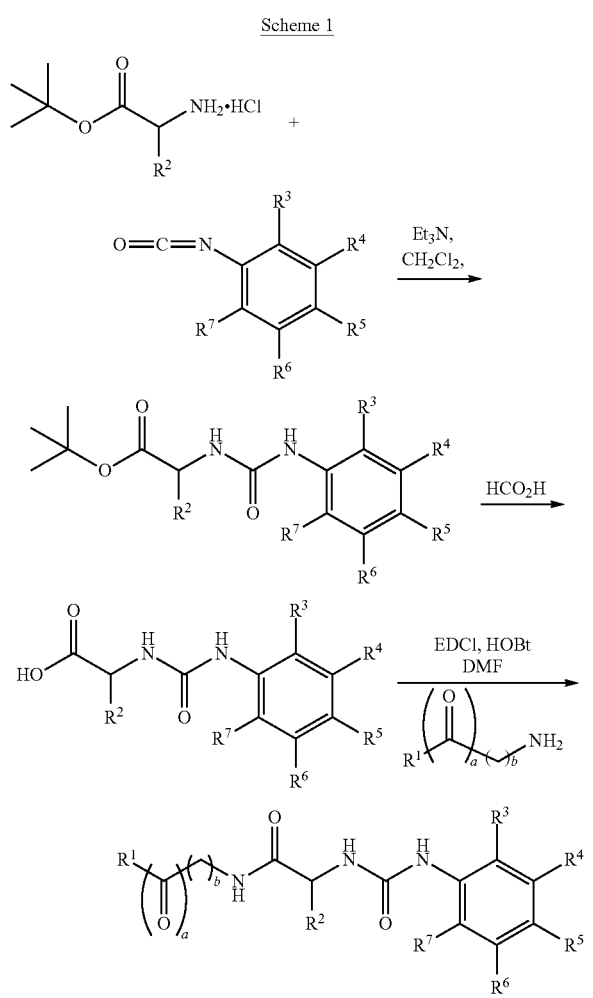

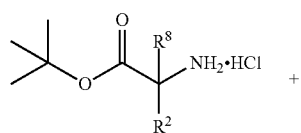

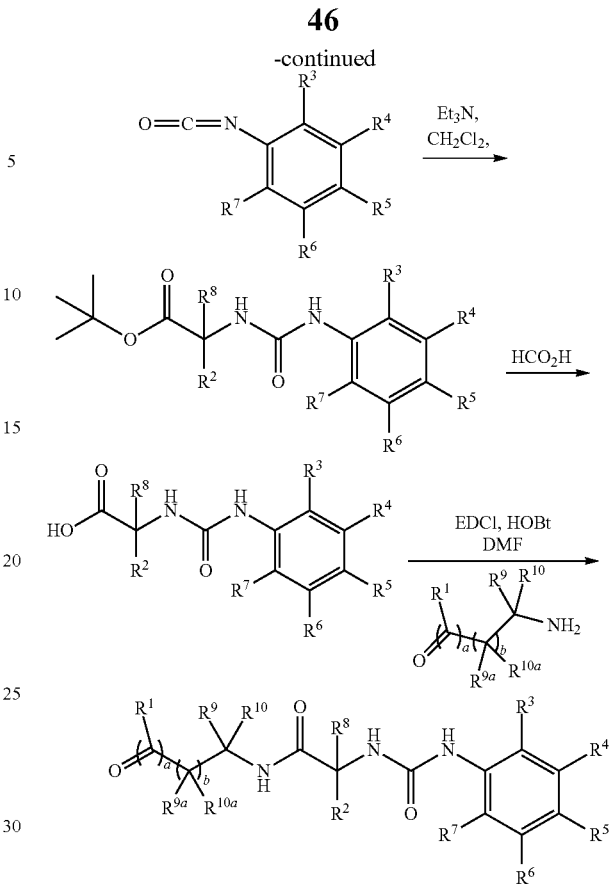

Compounds of Formula I were prepared as depicted in Scheme 1. Compounds of Formula II were prepared as depicted in Scheme 2. In general, a t-butyl ester derivative of an amino acid is reacted with a substituted phenylisocyanate to produce a phenylurea derivative. The t-butyl ester protecting group is then removed under acidic conditions to give the amino acid urea. The carboxylic acid group is then converted to an amide by treating the compound with activating reagents, such as 1-ethyl-3-(3-dimethylaminopropyl)carbodiimide (EDCI) and Hydroxybenzotriazole (HOBt) in the presence of an amine, or by other methods known to those skilled in the art. At this stage, those skilled in the art will appreciate that many additional compounds that fall under the scope of the invention may be prepared by performing various common chemical reactions. Details of certain specific chemical transformations are provided in the examples.

Those skilled in the art will be able to routinely modify and/or adapt the following scheme to synthesize any compounds of the invention covered by Formula I or Formula II.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms.

Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of hydrogen $^{1H}$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diastereoisomeric isomers, chromatographic separation may be employed. Compound names were generated with ACD version 12.5. In general, characterization of the compounds is performed according to the following methods, NMR spectra are recorded on 300 or 600 MHz Varian and acquired at room temperature. Chemical shifts are given in ppm referenced either to internal TMS or to the solvent signal.

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by medium pressure liquid chromatography, unless noted otherwise.

The following abbreviations are used in the examples:
Et$_3$N triethylamine
CH$_2$Cl$_2$ dichloromethane
CDCl$_3$ deuterated chloroform
MeOH methanol
CD$_3$OD deuterated methanol
Na$_2$SO$_4$ sodium sulfate
DMF N,N dimethylformamide
EDCI 1-ethyl-3-(3-dimethylaminopropyl)carbodiimide
HOBt Hydroxybenzotriazole
THF tetrahydrofuran
ClCO$_2$Et ethylchloroformate
NH$_3$ ammonia The following synthetic schemes illustrate how compounds according to the invention can be made. Those skilled in the art will be routinely able to modify and/or adapt the following schemes to synthesize any compound of the invention covered by Formula II.

Example 1

Intermediate 1 tert-Butyl (2S)-2-{[(4-Bromophenyl)carbamoyl]amino}-3-phenylpropanoate

To a solution of L-phenyl-alanine tert-butyl ester hydrochloride (100 mg, 0.41 mmol) and 6 mL of methylene chloride at 25° C. was added 4-bromo-phenyl isocyanate (81 mg, 0.41 mmol) and triethylamine (62 mg, 0.62 mmol). The resulting mixture was stirred at 25° C. for 30 minutes. The mixture was concentrated and the residue was purified by medium pressure liquid chromatography on silica gel using ethyl acetate:hexane (20:80) to yield Intermediate 1, as a white solid.

$^1$H NMR (CDCl$_3$, 300 MHz) δ: 7.20-7.35 (m, 5H), 7.13-7.20 (m, 2H), 7.01-7.10 (m, 2H), 6.79 (br. s., NH), 5.52 (br. s., NH), 4.70 (t, J=6.2 Hz, 1H), 2.91 (ddd, J=19.0 Hz, J=6.0 Hz, 2H), 1.47 (m, 9H).

Intermediates 2, 3 and 4 were prepared from the corresponding amino acid in a similar manner to the procedure described in Example 1 for Intermediate 1, starting with the appropriate amino acid. The results are described below in Table 1.

TABLE 1

| Interm. No. | IUPAC name Structure | $^1$H NMR δ (ppm) |
|---|---|---|
| 2 | tert-Butyl (2S,3S)-2-{[(4-bromo phenyl)carbamoyl]amino}-3-methylpentanoate 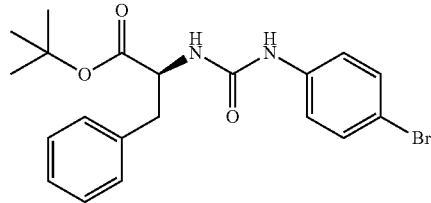 [SMILES: CC(C)(C)OC(=O)[C@H](Cc1ccccc1)NC(=O)Nc1ccc(Br)cc1] | $^1$H NMR (CDCl$_3$, 300 MHz) δ: 7.29-7.39 (m, 2H), 7.10-7.22 (m, 2H), 6.83 (br. s., 1H), 4.44 (d, J = 4.4 Hz, 1H), 1.81-1.99 (m, 1H), 1.36-1.46 (m, 1H), 1.08-1.31 (m, 1H), 0.86-1.02 (m, 6H). |

TABLE 1-continued

| Interm. No. | IUPAC name Structure | $^1$H NMR δ (ppm) |
|---|---|---|
| 3 | tert-Butyl (2S)-2-{[(4-bromophenyl)carbamoyl]amino}-pentanoate | $^1$H NMR (CDCl$_3$, 300 MHz) δ: 7.26-7.36 (m, 2H), 7.09-7.18 (m, 2H), 6.95 (br. s., NH), 4.40-4.50 (m, 1H), 1.73-1.89 (m, 1H), 1.52-1.72 (m, 1H), 1.25-1.46 (m, 2H), 0.95 (t, 2H). |
| 4 | tert-butyl (2S)-2-{[(4-bromo phenyl)carbamoyl]amino}-4-methylpentanoate | $^1$H NMR (CDCl$_3$, 300 MHz) δ: 7.20-7.33 (m, 2H), 7.04-7.15 (m, 2H), 4.44 (dd, J = 9.1, 5.3 Hz, 1H), 1.74 (dd, J = 12.9, 6.4 Hz, 1H), 1.54-1.68 (m, 1H), 1.50 (s, 9H), 1.40-1.47 (m, 1H), 0.97 (d, J = 3.5 Hz, 3H), 0.95 (d, 3H). |

Example 2

Intermediate 5

(2S)-2-{[(4-Bromophenyl)carbamoyl]amino}-3-phenylpropanoic Acid

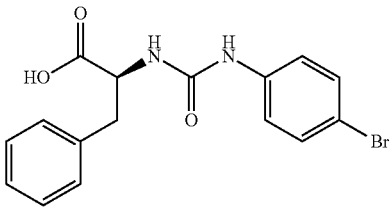 [SMILES: O=C(Nc1ccc(Br)cc1)N[C@@H](Cc1ccccc1)C(=O)O]

A solution of Intermediate 1 (60 mg, 0.15 mmol) and 0.5 mL of formic acid was stirred at 25° C. for 3 hours. The resulting mixture was quenched with water (1 mL) then extracted with ethyl acetate. The organic layer was washed with water, brine, dried over Na$_2$SO$_4$, filtered, and the filtrate was concentrated under reduced pressure. The residue was rinsed 4 times with methylene chloride:hexane (1:1) to yield Intermediate 5 as a white solid.

$^1$H NMR (acetone-d$_6$, 300 MHz) δ: 8.29 (s, NH), 7.40-7.50 (m, 2H), 7.32-7.40 (m, 2H), 7.18-7.31 (m, 5H), 5.98 (d, J=7.9 Hz, NH), 4.67 (m, 1H), 3.02 (ddd, J=19.0 Hz, J=6.0 Hz, 2H).

Intermediates 6, 7 and 8 and Compounds 1 through 6 were prepared from the corresponding urea derivative in a similar manner to the procedure described in Example 2 for Intermediate 5. The results are described below in Table 2.

TABLE 2

| Interm. No. | IUPAC name Structure | $^1$H NMR δ (ppm) |
|---|---|---|
| 6 | (2S,3S)-2-{[(4-bromophenyl)carbamoyl]amino}-3-methylpentanoic acid | $^1$H NMR (acetone-d$_6$, 300 MHz) δ: 8.24 (br. s., 1H), 7.44-7.53 (m, 2H), 7.32-7.42 (m, 2H), 6.08 (d, J = 8.8 Hz, 1H), 4.44 (dd, J = 8.6, 4.8 Hz, 1H), 1.86-2.00 (m, J = 9.1, 6.9, 4.6, 4.6 Hz, 1H), 1.43-1.61 (m, 1H), 1.15-1.33 (m, 1H), 0.88-1.04 (m, 6H). |

| | TABLE 2-continued | |
|---|---|---|
| 7 | (2S)-2-{[(4-bromophenyl)carbamoyl]amino}-pentanoic acid | ¹H NMR (acetone-d₆, 300 MHz) δ: 8.20 (s, NH), 7.43-7.52 (m, 2H), 7.33-7.41 (m, 2H), 6.08 (d, J = 9.1 Hz, NH), 4.38-4.50 (m, 1H), 1.77-1.92 (m, 1H), 1.61-1.76 (m, 1H), 1.36-1.53 (m, 2H), 0.89-1.00 (m, 3H). |
| 8 | (2S)-2-{[(4-bromophenyl)carbamoyl]amino}-4-methylpentanoic acid | ¹H NMR (acetone-d₆, 300 MHz) δ: 8.17 (s, NH), 7.43-7.51 (m, 2H), 7.35-7.41 (m, 2H), 6.04 (d, J = 9.1 Hz, NH), 4.42-4.53 (m, 1H), 1.73-1.88 (m, 1H), 1.53-1.73 (m, 2H), 0.97 (d, J = 2.1 Hz, 3H), 0.95 (d, 3H). |

| Comp. No. | IUPAC name Structure | ¹H NMR δ (ppm) |
|---|---|---|
| 1 | {[(2S)-2-{[(4-bromophenyl)carbamoyl]amino}-3-phenylpropanoyl]amino}acetic acid | ¹H NMR (acetone-d₆, 300 MHz) δ: 8.26 (s, NH), 7.71 (br. s., NH), 7.32-7.46 (m, 4H), 7.13-7.31 (m, 5H), 6.03 (d, J = 8.5 Hz, NH), 4.71 (td, J = 7.7, 5.4 Hz, 1H), 3.98 (d, J = 5.9 Hz, 2H), 3.14-3.26 (m, 1H), 3.01 (dd, 1H). |
| 2 | 3-{[(2S)-2-{[(4-bromophenyl)carbamoyl]amino}-3-phenylpropanoyl]amino}propanoic acid | ¹H NMR (acetone-d₆, 300 MHz) δ: 8.27 (s, NH), 7.44 (s, NH), 7.33-7.43 (m, 4H), 7.15-7.30 (m, 5H), 6.03 (d, J = 7.9 Hz, NH), 4.53-4.65 (m, 1H), 3.34-3.51 (m, 2H), 2.93-3.15 (m, 2H), 2.47 (td, 2H). |
| 3 | {[(2S,3S)-2-{[(4-bromo-2-fluorophenyl)carbamoyl]amino}-3-methylpentanoyl]amino}acetic acid | ¹H NMR (acetone-d₆, 300 MHz) δ: 8.28 (t, J = 8.9 Hz, 1H), 8.16 (br. s., NH), 7.67 (br. s., NH), 7.34 (dd, J = 11.0, 2.2 Hz, 1H), 7.23-7.30 (m, 1H), 6.57 (d, J = 9.4 Hz, NH), 4.37 (dd, J = 8.6, 5.7 Hz, 1H), 3.89-4.08 (m, 2H), 1.86-1.98 (m, 1H), 1.53-1.67 (m, 1H), 1.10-1.27 (m, 1H), 0.98 (d, J = 6.7 Hz, 3H), 0.85-0.94 (m, 3H). |
| 4 | {[(2S,3S)-2-{[(4-bromophenyl)carbamoyl]amino}-3-methylpentanoyl]amino}acetic acid | ¹H NMR (acetone-d₆, 300 MHz) δ: 8.27 (s, NH), 7.66 (br. s., NH), 7.42-7.51 (m, 2H), 7.32-7.41 (m, 2H), 6.08 (d, J = 8.2 Hz, NH), 4.34 (dd, J = 8.6, 5.7 Hz, 1H), 3.88-4.09 (m, 2H), 1.81-1.96 (m, 1H), 1.49-1.67 (m, 1H), 1.06-1.27 (m, 1H), 0.97 (d, J = 6.7 Hz, 3H), 0.86-0.93 (m, 3H). |

TABLE 2-continued

| 5 | {[(2S)-2-{[(4-bromophenyl)carbamoyl]amino}pentanoyl]amino}acetic acid 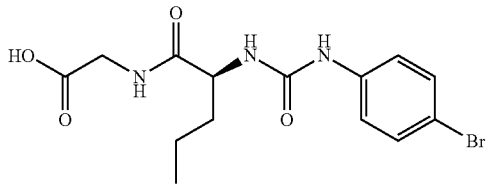 [SMILES: CCC[C@H](NC(=O)Nc1ccc(Br)cc1)C(=O)NCC(=O)O] | $^1$H NMR (acetone-$d_6$, 300 MHz) δ: 8.25 (s, NH), 7.67 (br. s., NH), 7.41-7.51 (m, 2H), 7.34-7.41 (m, 2H), 6.13 (d, J = 7.9 Hz, NH), 4.42 (td, J = 7.7, 5.4 Hz, 1H), 3.89-4.08 (m, 2H), 1.73-1.89 (m, 1H), 1.54-1.69 (m, 1H), 1.34-1.51 (m, 2H), 0.91 (t, J = 7.3 Hz, 3H). |
|---|---|---|
| 6 | {[(2S)-2-{[(4-bromophenyl)carbamoyl]amino}-4-methylpentanoyl]amino}acetic acid 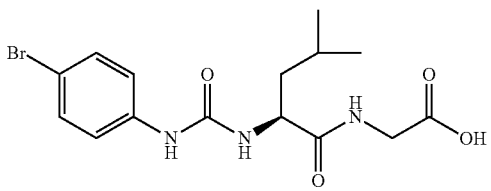 [SMILES: CC(C)C[C@H](NC(=O)Nc1ccc(Br)cc1)C(=O)NCC(=O)O] | $^1$H NMR (acetone-$d_6$, 300 MHz) δ: 8.19 (s, NH), 7.70 (br. s., NH), 7.42-7.51 (m, 2H), 7.33-7.41 (m, 2H), 6.07 (d, J = 7.6 Hz, NH), 4.46 (ddd, J = 9.6, 8.3, 5.0 Hz, 1H), 3.87-4.07 (m, 2H), 1.72-1.86 (m, 1H), 1.61-1.72 (m, 1H), 1.46-1.59 (m, 1H), 0.95 (s, 3H), 0.93 (s, 3H). |

Example 3

Compound 7 tert-Butyl {[(2S)-2-{[(4-bromophenyl)carbamoyl]amino}-3-phenylpropanoyl]amino}acetate

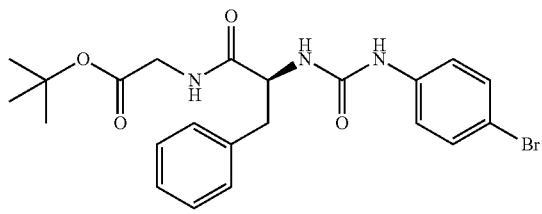 [SMILES: CC(C)(C)OC(=O)CNC(=O)[C@H](Cc1ccccc1)NC(=O)Nc1ccc(Br)cc1]

To a solution of Intermediate 5 (80 mg, 0.22 mmol) and 2 mL of anhydrous DMF at 25° C. was added EDCI (64 mg, 0.33 mmol), HOBt (45 mg, 0.33 mmol), glycine tert-butyl ester (44 mg, 0.33 mmol) and N-methylmorpholine (44 mg, 0.44 mmol). The resulting mixture was stirred at 25° C. for 12 hours. The mixture was quenched with water (1 mL), and the product was extracted with ethyl acetate (20 mL). The layers were separated, and the organic layer was washed with water, brine, dried over $Na_2SO_4$, filtered, and the filtrate was concentrated under reduced pressure. The resulting product was purified by medium pressure liquid chromatography on silica gel using ethyl acetate:hexane (40:60) to yield Compound 7 as a white solid.

$^1$H NMR (CDCl$_3$, 300 MHz) δ: 7.18-7.35 (m, 7H), 7.03 (d, J=8.5 Hz, 2H), 6.85 (br. s., 1H), 4.69 (t, J=7.5 Hz, 1H), 3.74-3.96 (m, 2H), 2.98-3.19 (m, 2H), 1.42 (s, 9H).

Compounds 8 through 27 and Intermediate 9 were prepared from the corresponding urea derivative in a similar manner to the procedure described in Example 3 for Compound 7. The results are described below in Table 3.

TABLE 3

| Comp. No. | IUPAC name / Structure | $^1$H NMR δ (ppm) |
|---|---|---|
| 8 | tert-butyl 3-{[(2S)-2-{[(4-bromophenyl)carbamoyl]amino}-3-phenylpropanoyl]amino}propanoate | $^1$H NMR (CDCl$_3$, 300 MHz) δ: 7.18-7.35 (m, 7H), 7.08-7.17 (m, 2H), 4.54-4.64 (m, 1H), 3.28-3.52 (m, 2H), 2.94-3.17 (m, 2H), 2.18-2.40 (m, 2H), 1.41 (s, 9H). |

TABLE 3-continued

| # | Name | 1H NMR |
|---|------|--------|
| 9 | (2S)-2-{[(4-bromophenyl)carbamoyl]amino}-N-(2-hydroxyethyl)-3-phenylpropanamide | ¹H NMR (CD₃OD, 300 MHz) δ: 7.30-7.37 (m, 2H), 7.17-7.30 (m, 7H), 4.50 (dd, J = 7.8, 6.3 Hz, 1H), 3.44-3.59 (m, 2H), 3.23-3.30 (m, 2H), 3.05-3.15 (m, 1H), 2.90-3.01 (m, 1H). |
| 10 | tert-butyl {[(2S,3S)-2-{[(4-bromo-2-fluorophenyl)carbamoyl]amino}-3-methylpentanoyl]amino}acetate | ¹H NMR (CDCl₃, 300 MHz) δ: 7.92-7.99 (t, J = 8.9 Hz, 1H), 7.40 (br. s., NH), 7.07-7.16 (m, 2H), 6.67 (s, NH), 6.54 (br. s., NH), 4.21-4.27 (m, 1H), 4.05-4.15 (m, 1H), 3.83-3.92 (m, 1H), 1.79-1.88 (m, 1H), 1.57-1.64 (m, 1H), 1.47 (s, 9H), 1.19-1.24 (m, 1H), 1.00 (d, J = 6.7 Hz, 3H), 0.92 (t, 3H). |
| 11 | tert-butyl {[(2S,3S)-2-{[(4-bromophenyl)carbamoyl]amino}-3-methylpentanoyl]amino}acetate | ¹H NMR (CD₃OD, 300 MHz) δ: 8.55 (s, NH), 8.36 (br. s., NH), 7.33-7.40 (m, 2H), 7.26-7.33 (m, 2H), 6.28 (d, J = 8.5 Hz, NH), 4.20 (dd, J = 8.6, 6.3 Hz, 1H), 3.72-3.97 (m, 2H), 1.80-1.94 (m, 1H), 1.56-1.70 (m, 1H), 1.45 (s, 9H), 1.13-1.31 (m, 1H), 1.01 (d, J = 6.7 Hz, 3H), 0.92-0.98 (m, 3H). |
| 12 | (2S,3S)-2-{[(4-bromophenyl)carbamoyl]amino}-3-methyl-N-(2-oxopropyl)pentanamide | 1H NMR (CD₃OD, 300 MHz) δ: 7.34-7.41 (m, 2H), 7.26-7.34 (m, 2H), 4.22 (d, J = 6.2 Hz, 1H), 4.05 (d, J = 8.2 Hz, 2H), 2.14 (s, 3H), 1.80-1.94 (m, 1H), 1.53-1.68 (m, 1H), 1.14-1.26 (m, 1H), 0.81-1.07 (m, 6H). |
| 13 | (2S,3S)-2-{[(4-bromo-2-fluorophenyl)carbamoyl]amino}-3-methyl-N-(2-oxopropyl)pentanamide | ¹H NMR (CD₃OD, 300 MHz) δ: 7.99 (t, J = 8.8 Hz, 1H), 7.31 (dd, J = 10.7, 2.2 Hz, 1H), 7.16-7.27 (m, 1H), 4.22 (d, J = 5.9 Hz, 1H), 3.94-4.14 (m, 2H), 2.14 (s, 3H), 1.84-1.96 (m, 1H), 1.52-1.67 (m, 1H), 1.14-1.32 (m, 1H), 1.01 (d, J = 7.0 Hz, 3H), 0.92-0.98 (m, 3H). |
| 14 | (2S,3S)-2-{[(4-bromophenyl)carbamoyl]amino}-N-(2-hydroxyethyl)-3-methylpentanamide | ¹H NMR (CD₃OD, 300 MHz) δ: 7.33-7.42 (m, 2H), 7.26-7.33 (m, 2H), 4.12 (d, J = 6.4 Hz, 1H), 3.55-3.65 (m, 2H), 3.32-3.37 (m, 1H), 1.76-1.91 (m, 1H), 1.48-1.63 (m, 1H), 1.09-1.31 (m, 2H), 0.90-0.99 (m, 6H). |

TABLE 3-continued

| 15 | (2S,3S)-2-{[(4-bromo-2-fluorophenyl)carbamoyl]amino}-N-(2-hydroxyethyl)-3-methylpentanamide | $^1$H NMR (CD$_3$OD, 300 MHz) δ: 7.99 (t, J = 8.6 Hz, 1H), 7.31 (dd, J = 10.8, 2.3 Hz, 1H), 7.18-7.27 (m, 1H), 4.13 (d, J = 6.4 Hz, 1H), 3.56-3.65 (m, 2H), 3.31-3.37 (m, 1H), 1.77-1.89 (m, 1H), 1.50-1.61 (m, 1H), 1.10-1.26 (m, 1H), 0.88-1.01 (m, 6H). |
|---|---|---|
| 16 | (2S)-2-{[(4-bromophenyl) carbamoyl]amino}-N-(2-oxopropyl)-3-phenylpropanamide | $^1$H NMR (acetone-d$_6$, 300 MHz) δ: 8.23 (s, NH), 7.59 (br. s., NH), 7.32-7.47 (m, 4H), 7.15-7.29 (m, 5H), 6.01 (d, J = 8.2 Hz, NH), 4.70 (td, J = 7.7, 5.7 Hz, 1H), 4.05 (d, J = 5.3 Hz, 2H), 3.12-3.24 (m, 1H), 2.95-3.06 (m, 1H), 2.10 (s, 3H). |
| 17 | (2S)-2-{[(4-bromo-2-fluorophenyl)carbamoyl]amino}-N-(2-oxopropyl)-3-phenylpropanamide | $^1$H NMR (acetone-d$_6$, 300 MHz) δ: 8.22 (t, J = 8.9 Hz, 1H), 8.12 (br. s., NH), 7.61 (br. s., NH), 7.32 (dd, J = 11.0, 2.2 Hz, 1H), 7.15-7.29 (m, 6H), 6.51 (d, J = 7.3 Hz, NH), 4.72 (td, J = 7.9, 5.6 Hz, 1H), 4.05 (dd, J = 5.6, 1.2 Hz, 2H), 3.14-3.24 (m, 1H), 2.95-3.05 (m, 1H), 2.10 (s, 3H). |
| 18 | tert-butyl {[(2S)-2-{[(4-bromophenyl)carbamoyl]amino}-pentanoyl]amino}acetate | $^{1H}$ NMR (acetone-d$_6$, 300 MHz) δ: 8.20 (s, NH), 7.60 (br. s., NH), 7.42-7.51 (m, 2H), 7.32-7.41 (m, 2H), 6.07 (d, J = 7.6 Hz, NH), 4.41 (td, J = 7.9, 5.3 Hz, 1H), 3.75-3.99 (m, 2H), 1.73-1.89 (m, 1H), 1.53-1.70 (m, 1H), 1.43 (s, 9H), 1.37-1.48 (m, 2H), 0.92 (t, J = 7.3 Hz, 3H). |
| 19 | (2S)-2-{[(4-bromo-2-fluorophenyl)carbamoyl]amino}-N-(2-hydroxyethyl)-3-phenylpropanamide | $^1$H NMR (CD$_3$OD, 300 MHz) δ: 7.91 (t, J = 8.6 Hz, 1H), 7.17-7.34 (m, 7H), 4.50 (dd, J = 8.2, 6.2 Hz, 1H), 3.44-3.59 (m, 2H), 3.23-3.27 (m, 2H), 3.05-3.17 (m, 1H), 2.87-2.99 (m, 1H). |
| 20 | (2S)-2-{[(4-bromophenyl)carbamoyl]amino}-N-(2-hydroxyethyl)pentanamid | $^1$H NMR (CD$_3$OD, 300 MHz) δ: 7.33-7.41 (m, 2H), 7.25-7.33 (m, 2H), 4.23 (dd, J = 8.2, 5.6 Hz, 1H), 3.56-3.63 (m, 2H), 1.69-1.84 (m, 1H), 1.54-1.68 (m, 1H), 1.29-1.51 (m, 2H), 0.91-1.02 (m, 3H). |

TABLE 3-continued

| | | |
|---|---|---|
| 21 | (2S)-2-{[(4-bromo-2-fluorophenyl)carbamoyl]amino}-N-(2-hydroxyethyl) pentanamide 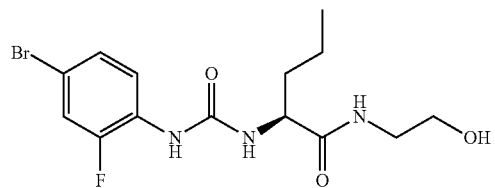 [SMILES: CCC[C@H](NC(=O)Nc1ccc(Br)cc1F)C(=O)NCCO] | $^1$H NMR (CD$_3$OD, 300 MHz) δ: 7.97 (t, J = 8.6 Hz, 1H), 7.31 (dd, J = 10.7, 2.2 Hz, 1H), 7.19-7.27 (m, 1H), 4.23 (dd, J = 8.1, 5.4 Hz, 1H), 3.56-3.66 (m, 2H), 1.68-1.83 (m, 1H), 1.54-1.68 (m, 1H), 1.34-1.51 (m, 2H), 0.91-1.03 (m, 3H). |
| 22 | methyl {[(2S)-2-{[(4-bromophenyl)carbamoyl]amino}-pentanoyl]amino}acetate 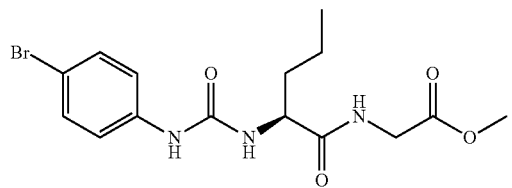 [SMILES: CCC[C@H](NC(=O)Nc1ccc(Br)cc1)C(=O)NCC(=O)OC] | $^1$H NMR (acetone-d$_6$, 300 MHz) δ: 8.19 (s, NH), 7.71 (br. s., NH), 7.42-7.52 (m, 2H), 7.31-7.42 (m, 2H), 6.07 (d, J = 8.2 Hz, NH), 4.34-4.47 (m, 1H), 3.86-4.10 (m, 2H), 3.66 (s, 3H), 1.73-1.87 (m, 1H), 1.55-1.71 (m, 1H), 1.35-1.51 (m, 2H), 0.92 (t, 3H). |
| 23 | ethyl {[(2S)-2-{[(4-bromophenyl)carbamoyl]amino}-pentanoyl]amino}acetate 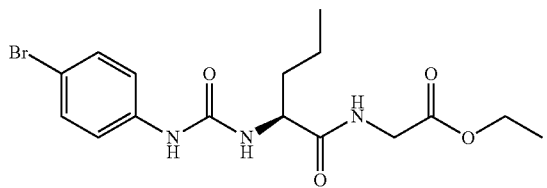 [SMILES: CCC[C@H](NC(=O)Nc1ccc(Br)cc1)C(=O)NCC(=O)OCC] | $^1$H NMR (acetone-d$_6$, 300 MHz) δ: 8.19 (s, NH), 7.69 (br. s., NH), 7.42-7.50 (m, 2H), 7.32-7.40 (m, 2H), 6.07 (d, J = 8.2 Hz, NH), 4.42 (td, J = 7.9, 5.6 Hz, 1H), 4.13 (q, J = 7.2 Hz, 2H), 3.85-4.06 (m, 2H), 1.73-1.88 (m, 1H), 1.55-1.69 (m, 1H), 1.34-1.51 (m, 2H), 1.20 (t, J = 7.3, 3H), 0.92 (t, J = 7.3, 3H). |
| 24 | isopropyl {[(2S)-2-{[(4-bromophenyl)carbamoyl]amino}-pentanoyl]amino}acetate 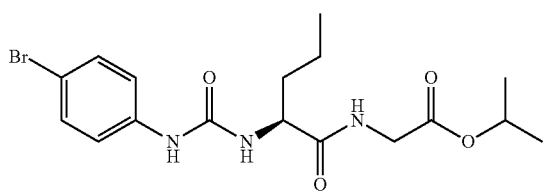 [SMILES: CCC[C@H](NC(=O)Nc1ccc(Br)cc1)C(=O)NCC(=O)OC(C)C] | $^1$H NMR (acetone-d$_6$, 300 MHz) δ: 8.20 (s, NH), 7.67 (br. s., NH), 7.43-7.51 (m, 2H), 7.33-7.42 (m, 2H), 6.07 (d, J = 9.7 Hz, NH), 4.97 (dt, J = 12.5, 6.2 Hz, 1H), 4.41 (td, J = 7.8, 5.4 Hz, 1H), 3.82-4.04 (m, 2H), 1.73-1.89 (m, 1H), 1.55-1.70 (m, 1H), 1.34-1.50 (m, 2H), 1.22 (s, 3H), 1.20 (s, 3H), 0.92 (t, J = 7.3, 3H). |
| 25 | tert-butyl {[(2S)-2-{[(4-bromophenyl)carbamoyl]amino}-4-methylpentanoyl]amino}acetate 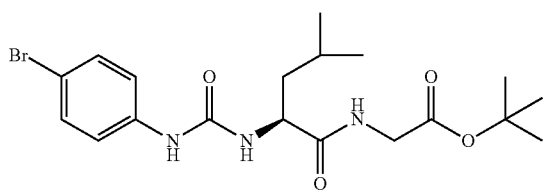 [SMILES: CC(C)C[C@H](NC(=O)Nc1ccc(Br)cc1)C(=O)NCC(=O)OC(C)(C)C] | $^1$H NMR (acetone-d$_6$, 300 MHz) δ: 8.16 (s, NH), 7.62 (br. s., NH), 7.42-7.49 (m, 2H), 7.33-7.40 (m, 2H), 6.03 (d, J = 8.8 Hz, NH), 4.40-4.51 (m, 1H), 3.76-3.95 (m, 2H), 1.72-1.84 (m, 1H), 1.60-1.73 (m, 1H), 1.45-1.58 (m, 1H), 0.95 (s, 3H), 0.93 (s, 3H). |
| 26 | (2S)-2-{[(4-bromophenyl)carbamoyl]amino}-N-(2-hydroxyethyl)-4-methylpentanamide 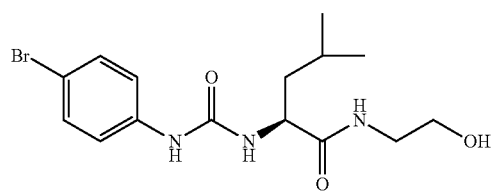 [SMILES: CC(C)C[C@H](NC(=O)Nc1ccc(Br)cc1)C(=O)NCCO] | $^1$H NMR (CD$_3$OD, 300 MHz) δ: 7.34-7.41 (m, 2H), 7.26-7.33 (m, 2H), 4.24-4.33 (m, 1H), 3.55-3.64 (m, 2H), 3.32-3.35 (m, 2H), 1.64-1.79 (m, 1H), 1.48-1.62 (m, 2H), 0.98 (d, J = 4.1 Hz, 3H), 0.96 (d, J = 3.8 Hz, 3H). |

TABLE 3-continued

| 27 | (2S)-2-{[(4-bromophenyl)carbamoyl]amino}-4-methyl-N-(2-oxopropyl)pentanamide | $^1$H NMR (acetone-$d_6$, 300 MHz) δ: 8.17 (s, NH), 7.61 (br. s., NH), 7.42-7.50 (m, 2H), 7.32-7.42 (m, 2H), 6.06 (d, J = 8.5 Hz, NH), 4.45 (ddd, J = 9.7, 8.1, 5.0 Hz, 1H), 4.04 (d, J = 5.6 Hz, 2H), 2.12 (s, 3H), 1.72-1.84 (m, 1H), 1.60-1.72 (m, 1H), 1.45-1.58 (m, 1H), 0.95 (s, 3H), 0.93 (s, 3H). |
|---|---|---|

| Interm. No. | IUPAC name Structure | $^1$H NMR δ(ppm) |
|---|---|---|
| 9 | (2S)-2-{[(4-bromophenyl)carbamoyl]amino}-N-hydroxypentanamide | $^1$H NMR (acetone-d6, 300 MHz) δ: 10.27 (br. s., OH), 8.18 (br. s., NH), 8.03 (s, NH), 7.42-7.50 (m, 2H), 7.32-7.41 (m, 2H), 6.11 (d, J = 9.1 Hz, NH), 4.23-4.34 (m, 1H), 1.52-1.80 (m, 2H), 1.27-1.49 (m, 2H), 0.87-0.95 (t, J = 7.3 Hz, 3H). |

Example 4

Compound 28

(2S,3S)—N-(2-amino-2-oxoethyl)-2-{[(4-bromophenyl) carbamoyl]amino}-3-methylpentanamide

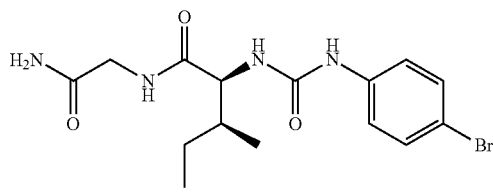 [SMILES: CC[C@H](C)[C@H](NC(=O)Nc1ccc(Br)cc1)C(=O)NCC(N)=O]

To a solution of Compound 11 (50 mg, 0.13 mmol) and 5 mL of anhydrous tetrahydrofuran under argon at −78° C. was added triethylamine (24 mg, 0.17 mmol) and ethyl chloroformate (17 mg, 0.16 mmol). The mixture was stirred at −78° C. for 30 minutes, and then ammonia gas was bubbled into reaction flask for 1 minute. The resulting mixture was stirred at 25° C. for 2 hours. The reaction was quenched with water (1 mL), and the residue was extracted with ethyl acetate (20 mL). The layers were separated, and the organic layer was washed with water, brine, dried over $Na_2SO_4$, filtered, and the filtrate was concentrated under reduced pressure. The resulting product was purified by medium pressure chromatography on silica gel using an eluent of methanol:dichloromethane (10:90) to yield to yield Compound 28 as a white solid.

$^1$H NMR (CD$_3$OD, 300 MHz) δ: 7.33-7.40 (m, 2H), 7.26-7.33 (m, 2H), 4.05 (d, J=6.7 Hz, 1H), 3.85 (q, J=17.0 Hz, 2H), 1.78-1.91 (m, 1H), 1.54-1.69 (m, 1H), 1.16-1.33 (m, 1H), 0.99 (d, J=6.7 Hz, 3H), 0.92-0.98 (m, 3H).

Compounds 29 through 85 as well as Intermediates 10 through 35 were prepared from the corresponding acid derivative in a similar manner to the procedure described in Example 4 for Compound 28.

TABLE 4

| Comp. No. | IUPAC name Structure | $^1$H NMR δ (ppm) |
|---|---|---|
| 29 | (2S,3S)-N-(2-amino-2-oxoethyl)-2-{[(4-bromo-2-fluorophenyl) carbamoyl]amino}-3-methylpentanamide | $^1$H NMR (CD$_3$OD, 300 MHz) δ: 8.00 (t, J = 8.6 Hz, 1H), 7.32 (dd, J = 10.7, 2.2 Hz, 1H), 7.18-7.26 (m, 1H), 4.05 (d, J = 6.4 Hz, 1H), 3.74-3.95 (m, 2H), 1.80-1.91 (m, 1H), 1.51-1.69 (m, 1H), 1.18-1.32 (m, 1H), 1.00 (d, J = 7.0 Hz, 3H), 0.92-0.98 (m, 3H). |

TABLE 4-continued

| | | |
|---|---|---|
| 30 | (2S)-N-(2-amino-2-oxoethyl)-2-{[(4-bromophenyl) carbamoyl]amino}-pentanamide 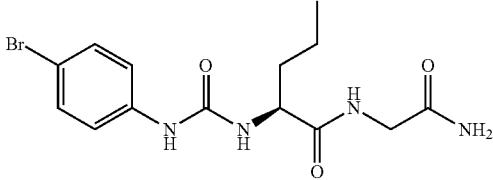 [SMILES: CCC[C@H](NC(=O)Nc1ccc(Br)cc1)C(=O)NCC(N)=O] | ¹H NMR (acetone-d₆, 300 MHz) δ: 8.27 (s, NH), 7.70 (br. s., NH), 7.41-7.48 (m, 2H), 7.33-7.41 (m, 2H), 7.02 (s, NH), 6.30 (s, NH), 6.22 (d, J = 5.3 Hz, NH), 4.22-4.32 (m, 1H), 3.72-3.91 (m, 2H), 1.73-1.88 (m, 1H), 1.56-1.71 (m, 1H), 1.37-1.53 (m, 2H), 0.88-0.97 (m, 3H). |
| 31 | (2S)-N-(2-amino-2-oxoethyl)-2-{[(4-bromo-2-fluorophenyl] carbamoyl}amino)pentanamide 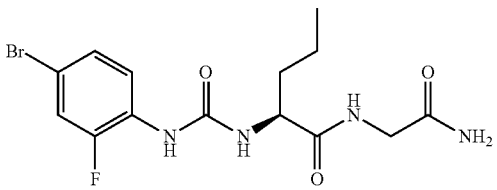 [SMILES: CCC[C@H](NC(=O)Nc1ccc(Br)cc1F)C(=O)NCC(N)=O] | ¹H NMR (acetone-d₆, 300 MHz) δ: 8.23 (t, J = 8.8 Hz, 1H), 8.13 (br. s., NH), 7.72 (s, NH), 7.35 (dd, J = 10.8, 2.3 Hz, 1H), 7.26 (dt, J = 8.9, 1.9 Hz, 1H), 7.00 (s, NH), 6.66 (d, J = 6.7 Hz, NH), 6.34 (s, NH), 4.29 (dd, J = 12.2, 8.1 Hz, 1H), 3.82 (dd, J = 5.9, 1.8 Hz, 2H), 1.75-1.90 (m, 1H), 1.58-1.73 (m, 1H), 1.37-1.53 (m, 2H), 0.89-0.98 (m, 3H). |
| 32 | (2S)-N-(2-amino-2-oxoethyl)-2-{[(4-bromophenyl) carbamoyl]amino}-4-methylpentanamide 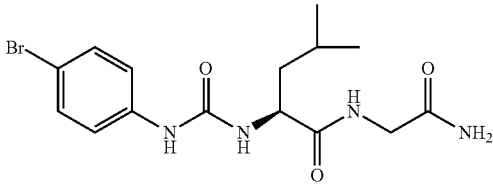 [SMILES: CC(C)C[C@H](NC(=O)Nc1ccc(Br)cc1)C(=O)NCC(N)=O] | ¹H NMR (acetone-d₆, 300 MHz) δ: 8.20 (s, NH), 7.77 (br. s., NH), 7.40-7.47 (m, 2H), 7.32-7.39 (m, 2H), 7.04 (br. s., NH), 6.38 (br. s., NH), 6.18 (d, J = 7.3 Hz, NH), 4.31 (ddd, J = 9.4, 7.0, 5.3 Hz, 1H), 3.71-3.93 (m, 2H), 1.69-1.85 (m, 1H), 1.49-1.69 (m, 2H), 0.96 (d, J = 3.2 Hz, 3H), 0.93 (d, J = 3.2 Hz, 3H). |
| 33 | tert-butyl{[(2S)-2-{[(4-bromo-2-fluorophenyl) carbamoyl] amino}-4-methylpentanoyl]amino}acetate 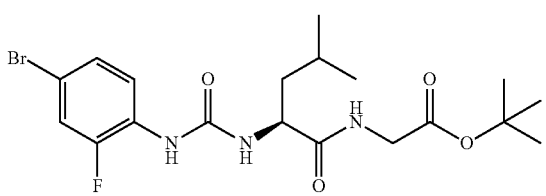 [SMILES: CC(C)C[C@H](NC(=O)Nc1ccc(Br)cc1F)C(=O)NCC(=O)OC(C)(C)C] | ¹H NMR (CDCl₃, 300 MHz) δ: 7.89 (t, J = 8.8 Hz, 1H), 7.55 (br. s., NH), 7.07 (dd, J = 10.7, 2.2 Hz, 1H), 6.95-7.04 (m, 1H), 6.84 (br. s., NH), 4.43 (br. s., NH), 4.00-4.16 (m, 1H), 3.81-3.92 (m, 1H), 1.69-1.88 (m, 1H), 1.56-1.70 (m, 2H), 1.47 (s, 9H), 0.97 (d, J = 4.7 Hz, 3H), 0.95 (d, 3H). |
| 34 | {[(2S)-2-{[(4-bromo-2-fluorophenyl)carbamoyl]amino}-4-methylpentanoyl]amino}acetic acid 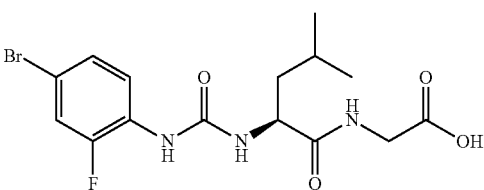 [SMILES: CC(C)C[C@H](NC(=O)Nc1ccc(Br)cc1F)C(=O)NCC(=O)O] | ¹H NMR (acetone-d₆, 300 MHz) δ: 8.27 (t, J = 8.8 Hz, 1H), 8.07 (br. s., NH), 7.71 (br. s., NH), 7.34 (dd, J = 10.8, 2.1 Hz, 1H), 7.27 (dt, J = 8.8, 1.8 Hz, 1H), 6.54 (d, J = 8.8 Hz, NH), 4.42-4.53 (m, 1H), 3.93-4.01 (m, 2H), 1.72-1.86 (m, 1H), 1.63-1.74 (m, 1H), 1.46-1.60 (m, 1H), 0.96 (s, 3H), 0.93 (s, 3H). |
| 35 | (2S)-2-{[(4-bromo-2-fluorophenyl)carbamoyl]amino}-4-methyl-N-(2-oxopropyl)pentanamide 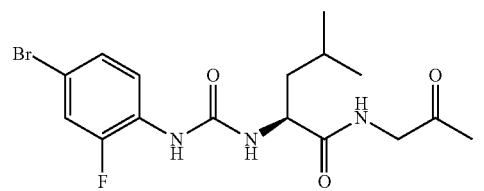 [SMILES: CC(=O)CNC(=O)[C@H](CC(C)C)NC(=O)Nc1ccc(Br)cc1F] | ¹H NMR (acetone-d₆, 300 MHz) δ: 8.30 (t, J = 8.8 Hz, 1H), 8.06 (br. s., NH), 7.62 (br. s., NH), 7.31-7.38 (m, 2H), 7.24-7.30 (m, 2H), 6.52 (d, J = 8.2 Hz, NH), 4.39-4.53 (m, 1H), 4.04 (d, J = 5.6 Hz, 2H), 2.10-2.15 (m, 3H), 1.70-1.86 (m, 1H), 1.61-1.71 (m, 1H), 1.47-1.62 (m, 1H), 0.96 (s, 3H), 0.93 (s, 3H). |

TABLE 4-continued

| 36 | (2S)-2-{[(4-bromo-2-fluorophenyl)carbamoyl]amino}-N-(2-hydroxyethyl)-4-methylpentanamide 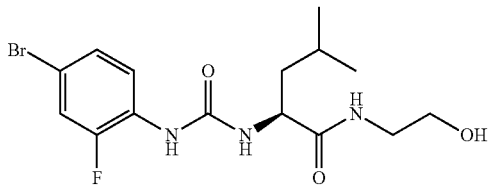 [SMILES: CC(C)C[C@H](NC(=O)Nc1ccc(Br)cc1F)C(=O)NCCO] | $^1$H NMR (CD$_3$OD, 300 MHz) δ: 7.97 (t, J = 8.8 Hz, 1H), 7.31 (dd, J = 10.8, 2.3 Hz, 1H), 7.18-7.27 (m, 1H), 4.28 (dd, J = 9.2, 5.4 Hz, 1H), 3.56-3.64 (m, 2H), 3.32-3.37 (m, 2H), 1.64-1.80 (m, 1H), 1.50-1.62 (m, 2H), 0.98 (d, J = 4.4 Hz, 3H), 0.96 (d, 3H). |
|---|---|---|
| 37 | (2S)-N-(2-amino-2-oxoethyl)-2-{[(4-bromo-2-fluorophenyl)carbamoyl]amino}-4-methylpentanamide 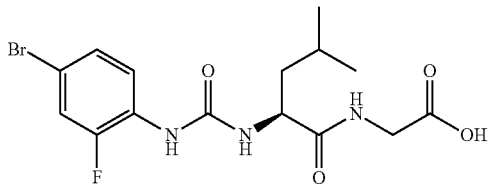 [SMILES: CC(C)C[C@H](NC(=O)Nc1ccc(Br)cc1F)C(=O)NCC(=O)O] | $^1$H NMR (acetone-d$_6$, 300 MHz) δ: 8.22 (t, J = 8.8 Hz, 1H), 8.09 (br. s., NH), 7.77 (br. s., NH), 7.34 (dd, J = 11.0, 2.2 Hz, 1H), 7.25 (dt, J = 8.9, 1.7 Hz, 1H), 6.99 (br. s., NH), 6.62 (d, J = 7.0 Hz, NH), 6.37 (br. s., NH), 4.33 (ddd, J = 9.6, 7.0, 5.1 Hz, 1H), 3.72-3.92 (m, 2H), 1.68-1.86 (m, 1H), 1.49-1.70 (m, 2H), 0.96 (d, J = 3.5 Hz, 3H), 0.94 (d, 3H). |
| 38 | tert-butyl (2S)-2-{[(2S)-2-{[(4-bromo-2-fluorophenyl)carbamoyl]amino}-4-methylpentanoyl]amino}propanoate 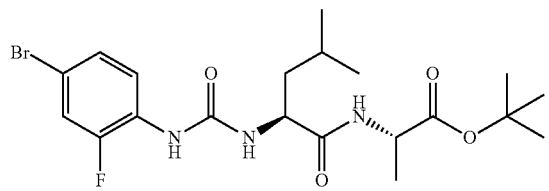 | $^1$H NMR (CDCl$_3$, 300 MHz) δ: 7.90 (t, J = 8.8 Hz, 1H), 7.45 (br. s., NH), 7.02-7.15 (m, 2H), 6.92 (s, NH), 6.61 (br. s., NH), 4.37-4.54 (m, 2H), 1.79 (dt, J = 13.2, 6.9 Hz, 1H), 1.56-1.69 (m, 2H), 1.46 (s, 9H), 1.40 (d, J = 7.3 Hz, 3H), 0.97 (s, 3H), 0.95 (s, 3H). |
| 39 | (2S)-2-{[(2S)-2-{[(4-bromo-2-fluorophenyl) carbamoyl]amino}-4-methylpentanoyl]amino}propanoic acid 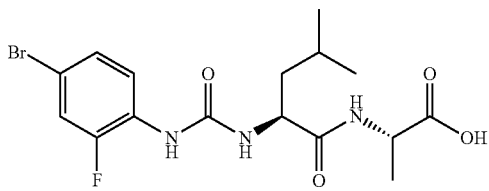 [SMILES: CC(C)C[C@H](NC(=O)Nc1ccc(Br)cc1F)C(=O)N[C@@H](C)C(=O)O] | $^1$H NMR (acetone-d$_6$, 300 MHz) δ: 8.26 (t, J = 8.9 Hz, 1H), 8.08 (br. s., NH), 7.67 (d, J = 7.0 Hz, NH), 7.33 (dd, J = 10.8, 2.3 Hz, 1H), 7.27 (dt, J = 8.8, 1.8 Hz, 1H), 6.52 (d, J = 9.1 Hz, NH), 4.40-4.54 (m, 2H), 1.72-1.87 (m, 1H), 1.59-1.72 (m, 1H), 1.45-1.57 (m, 1H), 1.39 (d, J = 7.3 Hz, 3H), 0.95 (s, 3H), 0.93 (s, 3H). |
| 40 | (2S)-N-[(1S)-2-amino-1-methyl-2-oxoethyl]-2-{[(4-bromo-2-fluorophenyl) carbamoyl]amino}-4-methylpentanamide 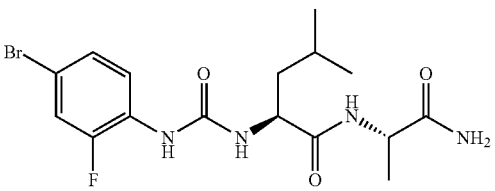 [SMILES: CC(C)C[C@H](NC(=O)Nc1ccc(Br)cc1F)C(=O)N[C@@H](C)C(N)=O] | $^1$H NMR (acetone-d$_6$, 300 MHz) δ: 8.25 (t, J = 8.8 Hz, 1H), 8.09 (br. s., NH), 7.57 (d, J = 5.6 Hz, NH), 7.35 (dd, J = 11.0, 2.2 Hz, 1H), 7.22-7.31 (m, 1H), 6.92 (br. s., NH), 6.54 (d, J = 7.3 Hz, NH), 6.29 (br. s., NH), 4.30-4.44 (m, 2H), 1.73-1.90 (m, 1H), 1.47-1.72 (m, 2H), 1.30 (d, J = 7.0 Hz, 3H), 0.95 (d, J = 1.5 Hz, 3H), 0.93 (d, 3H). |
| 41 | tert-butyl (2S)-2-{[(2S)-2-({[(4-bromophenyl) carbamoyl}amino)-4-methylpentanoyl]amino}propanoate 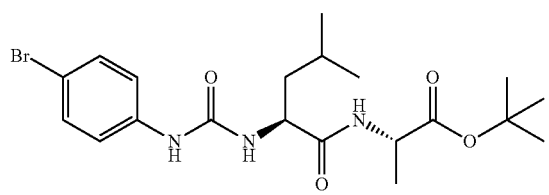 [SMILES: CC(C)C[C@H](NC(=O)Nc1ccc(Br)cc1)C(=O)N[C@@H](C)C(=O)OC(C)(C)C] | $^1$H NMR (CDCl$_3$, 300 MHz) δ: 7.62 (br. s., NH), 7.21-7.29 (m, 2H), 7.08-7.16 (m, 2H), 6.90 (br. s., NH), 4.39-4.50 (m, 1H), 4.35 (t, J = 7.0 Hz, 1H), 1.73-1.86 (m, 1H), 1.54-1.67 (m, 2H), 1.45 (s, 9H), 1.38 (d, 3H), 0.97 (d, J = 2.9 Hz, 3H), 0.95 (d, J = 2.9 Hz, 3H). |

TABLE 4-continued

| | | |
|---|---|---|
| 42 | tert-butyl (2S)-2-{[(2S)-2-{[(4-bromophenyl) carbamoyl]amino 4-methylpentanoyl]amino}-3-methylbutanoate | $^1$H NMR (CDCl$_3$, 300 MHz) δ: 7.45 (br. s., NH), 7.21-7.30 (m, 2H), 7.10-7.18 (m, 2H), 4.45 (t, J = 7.2 Hz, 1H), 4.32 (dd, J = 8.5, 5.0 Hz, 1H), 2.07-2.20 (m, 1H), 1.77 (dt, J = 13.3, 6.8 Hz, 1H), 1.56-1.67 (m, 2H), 1.47 (s, 9H), 0.98 (d, J = 2.3 Hz, 3H), 0.96 (d, 3H), 0.93 (s, 3H), 0.91 (s, 3H). |
| 43 | (2S)-2-{[(2S)-2-{[(4-bromophenyl)carbamoyl]amino}-4-methylpentanoyl]amino}propanoic acid | $^1$H NMR (acetone-d$_6$, 300 MHz) δ: 8.22 (s, NH), 7.66 (d, J = 6.4 Hz, NH), 7.43-7.50 (m, 2H), 7.34-7.41 (m, 2H), 6.05 (d, J = 7.9 Hz, NH), 4.39-4.52 (m, 2H), 2.81 (br. s., 4H), 1.71-1.86 (m, 1H), 1.57-1.71 (m, 1H), 1.43-1.57 (m, 1H), 1.39 (d, J = 7.3 Hz, 3H), 0.94 (s, 3H), 0.92 (s, 3H). |
| 44 | (2S)-2-{[(2S)-2-{[(4-bromophenyl)carbamoyl]amino}-4-methylpentanoyl]amino}-3-methylbutanoic acid | $^1$H NMR (acetone-d$_6$, 300 MHz) δ: 7.45 (br. s., NH), 7.21-7.30 (m, 2H), 7.10-7.18 (m, 2H), 4.45 (t, J = 7.2 Hz, 1H), 4.32 (dd, J = 8.5, 5.0 Hz, 1H), 2.07-2.20 (m, 1H), 1.77 (dt, J = 13.3, 6.8 Hz, 1H), 1.56-1.67 (m, 2H), 1.47 (s, 9H), 0.98 (d, J = 2.3 Hz, 3H), 0.96 (d, 3H), 0.93 (s, 3H), 0.91 (s, 3H). |
| 45 | (2S)-N-[(1S)-2-amino-1-methyl-2-oxoethyl]-2-{[(4-bromophenyl) carbamoyl]amino}-4-methylpentanamide | $^1$H NMR (acetone-d$_6$, 300 MHz) δ: 8.21 (s, NH), 7.56 (s, NH), 7.42-7.49 (m, 2H), 7.33-7.40 (m, 2H), 6.06-6.12 (s, NH), 4.28-4.44 (m, 2H), 1.70-1.89 (m, 1H), 1.59-1.70 (m, 1H), 1.47-1.59 (m, 1H), 1.30 (d, J = 7.3 Hz, 3H), 0.95 (s, 3H), 0.92 (s, 3H). |
| 46 | (2S)-N-[(1S)-1-(amino-3methyl-1-oxobutan-2-yl]-2-{[(4-bromophenyl) carbamoyl]amino}-4-methylpentanamide | $^1$H NMR (CD$_3$OD, 300 MHz) δ: 7.34-7.40 (m, 2H), 7.26-7.33 (m, 2H), 4.34 (dd, J = 9.5, 5.4 Hz, 1H), 4.21 (d, J = 7.0 Hz, 1H), 2.02-2.16 (m, 1H), 1.67-1.79 (m, 1H), 1.51-1.65 (m, 1H), 0.94-1.00 (m, 9H). |
| 47 | (2S)-2-{[(4-bromophenyl)carbamoyl]amino}-N-(2-hydroxy-2-methylpropyl)-4-methylpentanamide | $^1$H NMR (CD$_3$OD, 300 MHz) δ: 7.93 (s, NH), 7.33-7.40 (m, 2H), 7.26-7.33 (m, 2H), 6.28 (br. s., NH), 4.25-4.36 (m, 1H), 3.15-3.27 (m, 2H), 1.67-1.81 (m, 1H), 1.50-1.67 (m, 2H), 1.17 (s, 6H), 0.99 (d, J = 4.7 Hz, 3H), 0.97 (d, 3H). |

TABLE 4-continued

| | | |
|---|---|---|
| 48 | (2S)-2-{[(4-bromophenyl)carbamoyl]amino}-N-[2-hydroxy-1-(hydroxymethyl)ethyl]-4-methylpentanamide | $^1$H NMR (CD$_3$OD, 300 MHz) δ: 7.33-7.41 (m, 2H), 7.26-7.33 (m, 2H), 4.30 (dd, J = 9.4, 5.6 Hz, 1H), 3.86-3.96 (m, 1H), 3.62 (t, J = 5.6 Hz, 4H), 1.67-1.81 (m, 1H), 1.52-1.67 (m, 2H), 0.98 (d, J = 3.8 Hz, 3H), 0.96 (d, 3H). |
| 47 | (2S)-2-{[(4-bromophenyl)carbamoyl]amino}-N-(2,3-dihydroxypropyl)-4-methylpentanamide | $^1$H NMR (CD$_3$OD, 300 MHz) δ: 7.33-7.41 (m, 2H), 7.27-7.34 (m, 2H), 4.28 (dd, J = 8.9, 5.1 Hz, 1H), 3.64-3.76 (m, 1H), 3.46-3.52 (m, 2H), 3.33-3.42 (m, 1H), 3.15-3.27 (m, 1H), 1.67-1.80 (m, 1H), 1.48-1.67 (m, 2H), 0.98 (d, J = 4.7 Hz, 3H), 0.96 (d, 3H). |
| 48 | (2S)-2-{[(4-bromophenyl)carbamoyl]amino}-N-[(1R)-2-hydroxy-1-methylethyl]-4-methylpentanamide | $^1$H NMR (CD$_3$OD, 300 MHz) δ: 7.33-7.40 (m, 2H), 7.26-7.32 (m, 2H), 4.26 (dd, J = 8.2, 6.7 Hz, 1H), 3.88-3.99 (m, 1H), 3.49 (dd, J = 5.4, 1.3 Hz, 2H), 1.72 (dt, J = 13.3, 6.8 Hz, 1H), 1.50-1.60 (m, 2H), 1.14 (d, J = 6.7 Hz, 3H), 0.98 (d, J = 3.8 Hz, 3H), 0.96 (d, 3H). |
| 49 | tert-butyl (2S)-2-{[(2S)-2-{[4-bromophenyl)carbamoyl]amino}-4-methyl pentanoyl]amino}propanoate | $^1$H NMR (CD$_3$OD, 300 MHz) δ: 7.33-7.39 (m, 2H), 7.27-7.32 (m, 2H), 4.36 (dd, J = 9.5, 5.4 Hz, 1H), 4.26 (dd, J = 8.6, 5.4 Hz, 1H), 1.49-1.84 (m, 6H), 1.45 (s, 9H), 1.36-1.43 (m, 1H), 0.99 (d, J = 4.4 Hz, 3H), 0.97 (d, J = 4.1 Hz, 3H), 0.90-0.96 (m, 3H). |
| 50 | tert-butyl (2S)-{[(2S)-2-{[(4-bromophenyl)carbamoyl]amino}-4-methylpentanoyl]amino}(phenyl)ethanoate | $^1$H NMR (CD$_3$OD, 300 MHz) δ: 7.32-7.43 (m, 6H), 7.25-7.31 (m, 2H), 4.41 (dd, J = 9.4, 5.3 Hz, 1H), 1.72-1.81 (m, 1H), 1.49-1.70 (m, 2H), 1.40 (s, 9H), 1.17-1.19 (m, 0H), 0.99 (t, J = 6.7 Hz, 6H). |

TABLE 4-continued

| | | |
|---|---|---|
| 51 | (2S)-2-{[(2S)-2-{[(4-bromophenyl)carbamoyl]amino}-4-methylpentanoyl]amino}pentanoic acid | $^1$H NMR (CD$_3$OD, 300 MHz) δ: 7.33-7.40 (m, 2H), 7.25-7.33 (m, 2H), 4.32-4.44 (m, 2H), 1.35-1.90 (m, 7H), 0.99 (d, J = 3.8 Hz, 3H), 0.97 (d, J = 3.8 Hz, 3H), 0.91-0.96 (m, 3H). |
| 52 | (2S)-{[(2S)-2-{[(4-bromophenyl)carbamoyl]amino}-4-methylpentanoyl]amino}(phenyl)ethanoic acid | $^1$H NMR (CD$_3$OD, 300 MHz) δ: 7.40-7.47 (m, 2H), 7.23-7.39 (m, 7H), 4.41 (dd, J = 9.4, 5.3 Hz, 1H), 1.70-1.84 (m, 1H), 1.48-1.69 (m, 2H), 0.98 (t, 6H). |
| 53 | (2S)-N-[(2S)-1-amino-1-oxopentan-2-yl]-2-{[(4-bromophenyl)carbamoyl]amino}-4-methylpentanamide | $^1$H NMR (CD$_3$OD, 300 MHz) δ: 7.33-7.41 (m, 2H), 7.26-7.33 (m, 2H), 4.30 (ddd, J = 16.0, 9.4, 5.1 Hz, 1H), 1.50-1.86 (m, 5H), 1.33-1.48 (m, 2H), 0.95-1.01 (m, 6H), 0.89-0.96 (m, 3H). |
| 54 | (2S)-N-[(1S)-2-amino-2-oxo-1-phenylethyl]-2-{[(4-bromophenyl)carbamoyl]amino}-4-methylpentanamide | $^1$H NMR (CD$_3$OD, 300 MHz) δ: 7.41-7.48 (m, 2H), 7.24-7.42 (m, 7H), 4.36 (dd, J = 9.7, 5.0 Hz, 1H), 1.52-1.82 (m, 3H), 0.92-1.02 (m, 6H). |
| 55 | tert-butyl {[2-{[(4-bromophenyl)carbamoyl]amino}-2,4-dimethylpentanoyl]amino}acetate | $^1$H NMR (CDCl$_3$, 300 MHz) δ: 7.30-7.39 (m, 2H), 7.15-7.23 (m, 2H), 6.82 (br. s., 1H), 2.15-2.32 (m, 1H), 1.68-1.79 (m, 2H), 1.63 (s, 3H), 1.48 (s, 9H), 0.93 (d, J = 6.4 Hz, 3H), 0.89 (d, J = 6.2 Hz, 3H). |

TABLE 4-continued

| | | |
|---|---|---|
| 56 | {2-{[(4-bromophenyl)carbamoyl]amino}-2,4-dimethylpentanoyl]amino}acetic acid | $^1$H NMR (CD$_3$OD, 300 MHz) δ: 7.31 (d, J = 14.4 Hz, 2H), 3.92 (d, J = 1.2 Hz, 2H), 2.03-2.15 (m, 1H), 1.70-1.86 (m, 2H), 1.58 (s, 3H), 0.95 (d, J = 6.4 Hz, 3H), 0.91 (d, J = 6.4 Hz, 3H). |
| 57 | tert-butyl {[2-{[(4-bromophenyl)carbamoyl]amino}-2-ethylbutanoyl]amino}acetate | $^1$H NMR (CD$_3$OD, 300 MHz) δ: 7.247.39 (m, 2H), 7.24 (m, 2H), 6.50 (s, NH), 3.85 (s, 2H), 2.21-2.40 (m, 2H), 1.82 (dq, J = 14.2, 7.3 Hz, 2H), 1.45 (s, 9H), 0.85 (t, J = 7.3 Hz, 6H). |
| 58 | {[2-{[(4-bromophenyl)carbamoyl]amino}-2-ethylbutanoyl[amino}acetic acid | $^1$H NMR (CD$_3$OD, 600 MHz) δ: 7.35 (d, J = 8.8 Hz, 2H), 7.26-7.30 (m, 2H), 3.92 (s, 2H), 2.23-2.34 (m, 2H), 1.78-1.89 (m, 2H), 0.85 (t, J = 7.5 Hz, 6H). |
| 59 | tert-butyl {[2-{[(4-bromophenyl)carbamoyl]amino}-2-methylpropanoyl]amino}acetate | $^1$H NMR (CDCl$_3$, 300 MHz) δ: 7.23 (m, 2H), 7.39 (m, 2H), 3.81 (s, 2H), 1.52 (s, 6H), 1.45 (s, 9H). |
| 60 | {[2-{[(4-bromophenyl)carbamoyl]amino}-2-methylpropanoyl]amino}acetic acid | $^1$H NMR (CDCl$_3$, 300 MHz) δ: 7.23-7.40 (m, 4H), 3.81 (s, 2H), 1.51 (s, 6H). |
| 61 | (2S)-2-{[(4-bromophenyl)carbamoyl]amino}-N-[2-(dimethylamino)-2-oxoethyl]-4-methylpentanamide | $^1$H NMR (CD$_3$OD, 300 MHz) δ: 7.34-7.39 (m, 2H), 7.28-7.33 (m, 2H), 4.36 (dd, J = 10.0, 4.7 Hz, 1H), 3.97-4.13 (m, 2H), 3.03 (s, 3H), 2.94 (s, 3H), 1.51-1.83 (m, 3H), 0.94-1.03 (m, 6H). |
| 62 | tert-butyl {[(2S)-4-methyl-2-({[4-(trifluoromethyl)phenyl]carbamoyl}amino)pentanoyl]amino}acetate | $^1$H NMR (CD$_3$OD, 300 MHz) δ: 7.49-7.56 (m, 4H), 4.36 (dd, J = 9.7, 5.3 Hz, 1H), 3.70-3.95 (m, 2H), 1.69-1.86 (m, 1H), 1.51-1.68 (m, 2H), 1.43-1.46 (m, 9H), 0.99 (dd, J = 6.4, 4.1 Hz, 6H). |

TABLE 4-continued

| | | |
|---|---|---|
| 63 | {[(2S)-4-methyl-2-({[4-(trifluoromethyl)phenyl]carbamoyl}amino)pentanoyl]amino}acetic acid | ¹H NMR (CD₃OD, 300 MHz) δ: 7.50-7.56 (m, 4H), 6.37 (d, J = 7.6 Hz, NH), 4.38 (dd, J = 9.7, 5.0 Hz, 1H), 3.79-4.04 (m, 2H), 1.69-1.87 (m, 1H), 1.50-1.70 (m, 2H), 0.99 (dd, J = 6.4, 3.8 Hz, 6H). |
| 64 | tert-butyl {[(2R,3R)-2-{[(4-bromophenyl)carbamoyl]amino}-3-methylpentanoyl]amino}acetate | ¹H NMR (CD₃OD, 300 MHz) δ: 7.33-7.39 (m, 2H), 7.26-7.32 (m, 2H), 6.29 (s, NH), 4.17-4.24 (m, 0H), 3.73-3.95 (m, 2H), 1.87 (dtd, J = 9.8, 6.5, 3.2 Hz, 0H), 1.61 (ddt, J = 17.0, 7.4, 3.6 Hz, 0H), 1.43-1.47 (m, 9H), 1.11-1.27 (m, 0H), 0.90-1.03 (m, 6H). |
| 65 | {[(2R,3R)-2-{[(4-bromophenyl)carbamoyl]amino}-3-methylpentanoyl]amino}acetic acid | ¹H NMR (CD₃OD, 300 MHz) δ: 7.33-7.39 (m, 2H), 7.27-7.32 (m, 2H), 6.29 (s, NH), 4.19-4.26 (m, 1H), 3.81-4.00 (m, 2H), 1.84-1.94 (m, 1H), 1.60 (ddd, J = 13.2, 7.6, 3.5 Hz, 1H), 1.13-1.30 (m, 2H), 1.13-1.30 (m, 2H), 0.96 (d, J = 17.6 Hz, 3H). |
| 66 | tert-butyl {[(2R)-2-{[(4-bromophenyl)carbamoyl]amino}-4-methylpentanoyl]amino}acetate | ¹H NMR (CD₃OD, 600 MHz) δ: 7.35-7.38 (m, 2H), 7.28-7.31 (m, 2H), 4.34 (dd, J = 10.0, 5.0 Hz, 1H), 3.75-3.91 (m, 2H), 1.73-1.80 (m, 1H), 1.63-1.68 (m, 1H), 1.53-1.59 (m, 1H), 1.44-1.47 (m, 9H), 0.99 (d, J = 6.7 Hz, 3H), 0.97 (d, J = 6.7 Hz, 3H). |
| 67 | {[(2R)-2-{[(4-bromophenyl)carbamoyl]amino}-4-methylpentanoyl]amino}acetic acid | ¹H NMR (CD₃OD, 600 MHz) δ: 7.34-7.39 (m, 2H), 7.26-7.32 (m, 2H), 4.32-4.38 (m, 1H), 3.84-4.00 (m, 2H), 1.72-1.81 (m, 1H), 1.63-1.70 (m, 1H), 1.52-1.60 (m, 1H), 0.99 (d, J = 6.7 Hz, 3H), 0.97 (d, J = 6.7 Hz, 3H). |
| 68 | tert-butyl {[(2S)-4-methyl-2-({[4-(methylsulfanyl)phenyl]carbamoyl}amino)pentanoyl]amino}acetate | ¹H NMR (CD₃OD, 300 MHz) δ: 7.27-7.34 (m, 2H), 7.17-7.24 (m, 2H), 6.24 (d, J = 7.9 Hz, NH), 4.30-4.40 (m, 1H), 3.72-3.95 (m, 2H), 2.40-2.43 (m, 3H), 1.69-1.84 (m, 1H), 1.50-1.68 (m, 2H), 1.44-1.47 (m, 9H), 0.99 (dd, J = 6.4, 4.7 Hz, 6H). |

TABLE 4-continued

| | | |
|---|---|---|
| 69 | 2-methyl-2-{[(2S)-4-methyl-2-({[4-(trifluoromethyl)phenyl]carbamoyl}amino)pentanoyl]amino}propanoic acid | ¹H NMR (CD₃OD, 300 MHz) δ: 8.27 (s, NH), 7.52 (d, J = 19.9 Hz, 4H), 6.29 (d, J = 8.5 Hz, NH), 4.27-4.43 (m, 1H), 1.70-1.85 (m, 1H), 1.45-1.67 (m, 8H), 0.98 (dd, J = 6.4, 2.9 Hz, 6H). |
| 70 | {[(2S)-4-methyl-2-({[4-(methylsulfanyl)phenyl]carbamoyl}amino)pentanoyl]amino}acetic acid | ¹H NMR (CD₃OD, 300 MHz) δ: 7.26-7.34 (m, 2H), 7.17-7.24 (m, 2H), 4.30-4.41 (m, 1H), 3.80-4.03 (m, 2H), 2.39-2.43 (m, 3H), 1.49-1.84 (m, 3H), 0.98 (dd, J = 6.4, 4.1 Hz, 6H). |
| 71 | tert-butyl ({(2S)-4-methyl-2-[({4-[(trifluoromethyl)sulfanyl]phenyl}carbamoyl)amino]pentanoyl}amino)acetate | ¹H NMR (CD₃OD, 300 MHz) δ: 7.52-7.57 (m, 2H), 7.47-7.52 (m, 2H), 4.32-4.40 (m, 1H), 3.72-3.95 (m, 2H), 1.69-1.84 (m, 1H), 1.50-1.68 (m, 2H), 1.42-1.47 (m, 9H), 0.99 (dd, J = 6.3, 4.2 Hz, 6H). |
| 72 | ({(2S)-4-methyl-2-[({4-[(trifluoromethyl)sulfanyl]phenyl}carbamoyl)amino]pentanoyl}amino)acetic acid | ¹H NMR (CD₃OD, 300 MHz) δ: 7.47-7.57 (m, 4H), 4.37 (dd, J = 9.5, 5.1 Hz, 1H), 3.83-4.02 (m, 2H), 1.70-1.83 (m, 1H), 1.51-1.68 (m, 2H), 0.99 (d, J = 3.8 Hz, 3H), 0.97 (d, J = 3.8 Hz, 3H). |
| 73 | tert-butyl 2-{[(2S)-2-{[(4-bromophenyl)carbamoyl]amino}-4-methylpentanoyl]amino}-2-methylpropanoate | ¹H NMR (CD₃OD, 300 MHz) δ: 7.33-7.38 (m, 2H), 7.26-7.32 (m, 2H), 4.31 (dd, J = 9.1, 5.6 Hz, 1H), 1.67-1.80 (m, 1H), 1.45-1.63 (m, 2H), 1.39-1.44 (m, 15H), 0.97 (dd, J = 6.6, 3.1 Hz, 6H). |
| 74 | 2-{[(2S)-2-{[(4-bromophenyl)carbamoyl]amino}-4-methylpentanoyl]amino}-2-methylpropanoic acid | ¹H NMR (CD₃OD, 300 MHz) δ: 8.46 (s, NH), 8.26 (s, NH), 7.33-7.38 (m, 2H), 7.25-7.31 (m, 2H), 4.32 (dd, J = 9.2, 5.4 Hz, 1H), 1.68-1.80 (m, 1H), 1.51-1.65 (m, 2H), 1.49 (s, 3H), 1.48 (s, 3H), 0.98 (d, J = 3.5 Hz, 3H), 0.96 (d, J = 3.5 Hz, 3H). |

TABLE 4-continued

| # | Name | ¹H NMR |
|---|---|---|
| 75 | tert-butyl {[(2S)-4-methyl-2-({[4-(methylsulfinyl)phenyl]carbamoyl}amino)pentanoyl]amino}acetate | ¹H NMR (CD₃OD, 300 MHz) δ: 7.61 (s, 4H), 4.37 (dd, J = 9.8, 5.1 Hz, 1H), 3.72-3.96 (m, 2H), 2.77 (s, 3H), 1.69-1.85 (m, 1H), 1.51-1.69 (m, 2H), 1.45 (s, 9H), 0.94-1.05 (m, 6H). |
| 76 | tert-butyl {[(2S)-4-methyl-2-({[4-(methylsulfonyl)phenyl]carbamoyl}amino)pentanoyl]amino}acetate | ¹H NMR (CD₃OD, 300 MHz) δ: 7.77-7.86 (m, 2H), 7.57-7.67 (m, 2H), 4.37 (dd, J = 9.7, 5.0 Hz, 1H), 3.71-3.96 (m, 2H), 3.07 (s, 3H), 1.69-1.83 (m, 1H), 1.51-1.70 (m, 2H), 1.40-1.49 (m, 9H), 0.94-1.03 (m, 6H). |
| 77 | {[(2S)-4-methyl-2-({[4-(methylsulfinyl)phenyl]carbamoyl}amino)pentanoyl]amino}acetic acid | ¹H NMR (CD₃OD, 300 MHz) δ: 7.57-7.66 (m, 4H), 4.38 (dd, J = 9.7, 5.0 Hz, 1H), 3.81-4.03 (m, 2H), 2.77 (s, 3H), 1.69-1.85 (m, 1H), 1.48-1.68 (m, 2H), 0.92-1.03 (m, 6H). |
| 78 | {[(2S)-4-methyl-2-({[4-(methylsulfonyl)phenyl]carbamoyl}amino)pentanoyl]amino}acetic acid | ¹H NMR (CD₃OD, 300 MHz) δ: 7.76-7.87 (m, 2H), 7.57-7.68 (m, 2H), 6.43 (d, J = 8.5 Hz, NH), 4.32-4.45 (m, 1H), 3.81-4.04 (m, 2H), 3.07 (s, 3H), 1.71-1.83 (m, 1H), 1.49-1.70 (m, 2H), 0.98 (dd, J = 6.4, 3.5 Hz, 6H). |
| 79 | tert-butyl 2-methyl-2-{[(2S)-4-methyl-2-({[4-(trifluoromethyl)phenyl]carbamoyl}amino)pentanoyl]amino}propanoate | ¹H NMR (CD₃OD, 300 MHz) δ: 7.46-7.58 (m, 2H), 4.33 (dd, J = 9.2, 5.7 Hz, 1H), 1.69-1.86 (m, 1H), 1.46-1.66 (m, 2H), 1.36-1.46 (m, 15H), 0.94-1.04 (m, 6H). |
| 80 | tert-butyl {[(2S)-2-{[(4-bromophenyl)carbamoyl]amino}-4-(methylsulfanyl)butanoyl]amino}acetate | ¹H NMR (CD₃OD, 300 MHz) δ: 7.24-7.41 (m, 4H), 4.44 (dd, J = 7.8, 5.4 Hz, 1H), 3.70-3.99 (m, 2H), 2.54-2.68 (m, 2H), 2.12-2.18 (m, 1H), 2.11 (s, 3H), 1.85-2.02 (m, 1H), 1.41-1.50 (m, 9H).<br>[α]D = −21.8 (c = 1.00, MeOH) |

TABLE 4-continued

| | | | |
|---|---|---|---|
| 81 | tert-butyl {[(2S)-2-{[(4-bromophenyl)carbamoyl]amino}-4-(methylsulfonyl)butanoyl]amino}acetate | | $^1$H NMR (CD$_3$OD, 300 MHz) δ: 7.26-7.43 (m, 4H), 4.43-4.57 (m, 1H), 3.70-4.03 (m, 2H), 3.24 (s, 2H), 2.99 (s, 4H), 2.28-2.42 (m, 1H), 2.11-2.26 (m, 1H), 1.47 (s, 9H). |
| 82 | {[(2S)-2-{[(4-bromophenyl)carbamoyl]amino}-4-(methylsulfanyl)butanoyl]amino}acetic acid | | $^1$H NMR (CD$_3$OD, 300 MHz) δ: 7.25-7.44 (m, 4H), 6.55 (d, J = 7.3 Hz, NH), 4.53 (m, 1H), 3.79-4.10 (m, 2H), 3.26 (m, 2H), 2.98 (s, 3H), 2.26-2.42 (m, 1H), 2.20 (m, 1H). |
| 83 | {[(2S)-2-{[(4-bromophenyl)carbamoyl]amino}-4-(methylsulfonyl)butanoyl]amino}acetic acid | | $^1$H NMR (CD$_3$OD, 300 MHz) δ: 7.26-7.42 (m, 4H), 6.55 (d, J = 7.3 Hz, NH), 4.47-4.58 (m, 1H), 3.80-4.11 (m, 2H), 3.25 (m, 2H), 2.98 (s, 3H), 2.28-2.43 (m, 1H), 2.11-2.27 (m, 1H). |
| 84 | tert-butyl {[2-{[4-bromophenyl)carbamoyl]amino}-3-(1H-imidazol-4-yl)propanoyl]amino}acetate | | $^1$H NMR (CD$_3$OD, 300 MHz) δ: 7.61 (s, 1H), 7.21-7.41 (m, 4H), 6.94 (s, 1H), 4.51-4.64 (m, 1H), 3.75-3.96 (m, 2H), 3.07-3.22 (m, 1H), 2.93-3.06 (m, 1H), 1.49 (s, 9H). |
| 85 | {[2-{[(4-bromophenyl)carbamoyl]amino}-3-(1H-imidazol-4-yl)propanoyl]amino}acetic acid | | $^1$H NMR (DMSO-D$_6$, 300 MHz) δ: 8.93 (NH, 1H), 8.42 (br. s., NH), 7.67 (s, 1H), 7.34 (d, J = 4.1 Hz, 4H), 6.88 (s, 1H), 6.28 (d, J = 7.3 Hz, NH), 4.44 (m., 1H), 3.55-3.90 (m, 2H), 2.93 (m., 2H). |

TABLE 4-continued

| | | |
|---|---|---|
| 86 | tert-butyl 2-{[(2R)-2-{[(4-bromophenyl)carbamoyl]amino}-4-methylpentanoyl]amino}-2-methylpropanoate | ¹H NMR (CD₃OD, 300 MHz) δ: 7.33-7.38 (m, 2H), 7.26-7.32 (m, 2H), 4.31 (dd, J = 9.1, 5.6 Hz, 1H), 1.67-1.80 (m, 1H), 1.45-1.63 (m, 2H), 1.39-1.44 (m, 15H), 0.97 (dd, J = 6.6, 3.1 Hz, 6H). |
| 87 | 2-{[(2R)-2-{[(4-bromophenyl)carbamoyl]amino}-4-methylpentanoyl]amino}-2-methylpropanoic acid | ¹H NMR (CD₃OD, 300 MHz) δ: 8.46 (s, NH), 8.23 (s, 2NH), 7.33-7.39 (m, 2H), 7.26-7.31 (m, 2H), 6.19 (d, J = 8.2 Hz, NH), 4.31 (m 1H), 1.73 (m, 1H), 1.51-1.65 (m, 2H), 1.49 (s, 3H), 1.48 (s, 3H), 0.98 (d, J = 3.8 Hz, 6H), 0.96 (d, J = 3.5 Hz, 6H). |
| 88 | tert-butyl {[4-amino-2-{[(4-bromophenyl) carbamoyl]amino}-4-oxobutanoyl]amino}acetate | ¹H NMR (CD₃OD, 300 MHz) δ: 7.27-7.42 (m, 4H), 4.69 (t, J = 6.0 Hz, 1H), 3.75-3.94 (m, 2H), 2.70-2.78 (m, 2H), 1.45 (s, 9H). |
| 89 | 4-amino-2-{[(4-bromophenyl)carbamoyl]amino}-4-oxobutanoic acid | ¹H NMR (CD₃OD, 300 MHz) δ: 7.26-7.44 (m, 4H), 4.62 (t, J = 5.3 Hz, 1H), 2.70-2.94 (m, 2H). |
| 90 | tert-butyl {[2-{[(4-bromophenyl)carbamoyl]amino}-3-(1H-indol-3-yl) propanoyl]amino}acetate | ¹H NMR (CD₃OD, 300 MHz) δ: 7.56-7.61 (m, 1H), 7.30-7.36 (m, 3H), 7.23-7.26 (m, 2H), 7.16 (s, NH), 7.08 (td, J = 7.6, 1.2 Hz, 1H), 6.95-7.02 (m, 1H), 6.13 (d, J = 7.3 Hz, NH), 4.60-4.68 (m, 1H), 3.80 (s, 2H), 3.32-3.38 (m, 1H), 3.11-3.23 (m, 1H), 1.43-1.47 (m, 9H). |

TABLE 4-continued

| | | |
|---|---|---|
| 91 | tert-butyl {[4-amino-2-{[(4-bromophenyl) carbamoyl]amino}-4-oxobutanoyl]amino}acetate<br>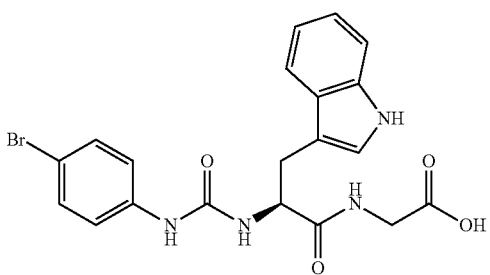 [SMILES: O=C(O)CNC(=O)[C@H](Cc1c[nH]c2ccccc12)NC(=O)Nc1ccc(Br)cc1] | ¹H NMR (CD₃OD, 300 MHz) δ: 7.27-7.42 (m, 4H), 4.69 (t, J = 6.0 Hz, 1H), 3.75-3.94 (m, 2H), 2.70-2.78 (m, 2H), 1.45 (s, 9H). |

| Interm. No. | IUPAC name Structure | ¹H NMR δ (ppm) |
|---|---|---|
| 10 | (2S,3S)-2-{[(4-bromophenyl)carbamoyl]amino}-3-methylpentanamide<br>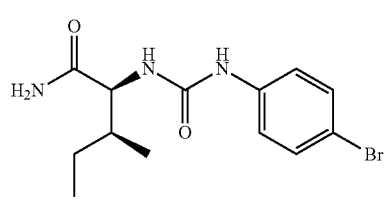 [SMILES: CC[C@H](C)[C@H](NC(=O)Nc1ccc(Br)cc1)C(N)=O] | ¹H NMR (CD₃OD, 300 MHz) δ: 7.33-7.41 (m, 2H), 7.26-7.33 (m, 2H), 4.18 (d, J = 6.2 Hz, 1H), 1.74-1.91 (m, 1H), 1.50-1.66 (m, 1H), 1.11-1.33 (m, 1H), 0.99 (d, J = 7.0 Hz, 3H), 0.91-0.97 (m, 3H). |
| 11 | (2S,3S)-2-{[(4-bromo-2-fluorophenyl) carbamoyl]amino}-3-methylpentanamide<br>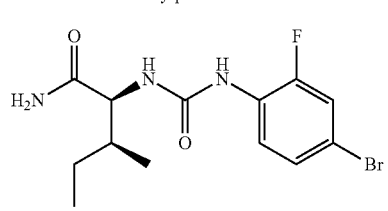 | ¹H NMR (CD₃OD, 300 MHz) δ: 7.99 (t, J = 8.8 Hz, 1H), 7.31 (dd, J = 10.7, 2.2 Hz, 1H), 7.19-7.27 (m, 1H), 4.18 (d, J = 6.2 Hz, 1H), 1.78-1.95 (m, 1H), 1.49-1.65 (m, 1H), 1.10-1.27 (m, 1H), 1.00 (d, J = 6.7 Hz, 3H), 0.91-0.98 (m, 3H). |
| 12 | (2S)-2-{[(4-bromo-2-fluorophenyl) carbamoyl]amino}-pentanamide<br>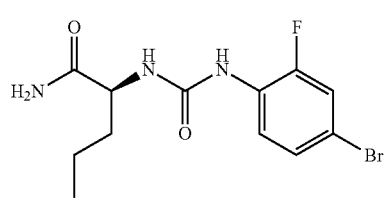 [SMILES: CCC[C@H](NC(=O)Nc1ccc(Br)cc1F)C(N)=O] | ¹H NMR (acetone-d6, 300 MHz) δ: 8.28 (t, J = 8.8 Hz, 1H), 8.12 (br. s., NH), 7.33 (dd, J = 11.0, 2.2 Hz, 1H), 7.26 (dt, J = 8.9, 1.9 Hz, 1H), 7.07 (br. s., NH), 6.55 (d, J = 7.0 Hz, NH), 6.40 (br. s., NH), 4.38 (td, J = 7.8, 5.3 Hz, 1H), 1.73-1.89 (m, 1H), 1.54-1.70 (m, 1H), 1.24-1.49 (m, 2H), 0.92 (t, J = 7.3 Hz, 3H). |
| 13 | (2S)-2-{[(4-bromophenyl)carbamoyl]amino}-4-methylpentanamide<br>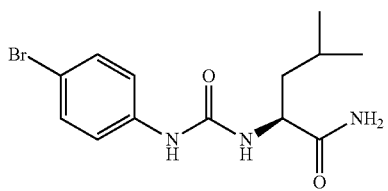 [SMILES: CC(C)C[C@H](NC(=O)Nc1ccc(Br)cc1)C(N)=O] | ¹H NMR (acetone-d6, 300 MHz) δ: 8.17 (s, NH), 7.41-7.50 (m, 2H), 7.33-7.40 (m, 2H), 6.03 (d, J = 8.2 Hz, NH), 4.39 (ddd, J = 9.4, 8.2, 5.0 Hz, 1H), 3.58 (q, J = 5.6 Hz, 2H), 3.26-3.37 (m, 2H), 1.66-1.81 (m, 1H), 1.44-1.67 (m, 2H), 0.94 (d, J = 1.5 Hz, 3H), 0.92 (d, J = 1.4 Hz, 3H). |

TABLE 4-continued

| | | |
|---|---|---|
| 14 | (2S)-2-({[(4-bromo-2-fluorophenyl) carbamoyl]amino}-4-methylpentanoate 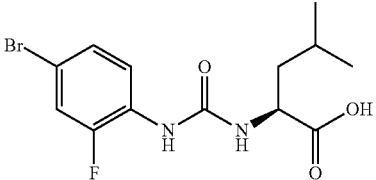 [SMILES: CC(C)C[C@H](NC(=O)Nc1ccc(Br)cc1F)C(=O)O] | $^{1}$H NMR (acetone-d6, 300 MHz) δ: 8.27 (t, J = 8.9 Hz, 1H), 8.06 (br. s., NH), 7.34 (dd, J = 10.8, 2.3 Hz, 1H), 7.25-7.31 (m, 1H), 6.53 (d, J = 7.0 Hz, NH), 4.43-4.55 (m, 1H), 1.73-1.87 (m, 1H), 1.53-1.71 (m, 2H), 0.98 (d, J = 1.5 Hz, 3H), 0.96 (d, J = 1.5 Hz, 3H). |
| 15 | (2S)-2-{[(4-bromo-2-fluorophenyl) carbamoyl]amino}-4-methylpentanamide 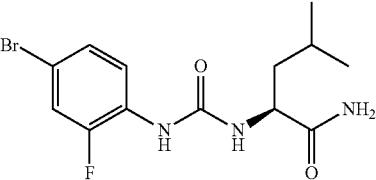 [SMILES: CC(C)C[C@H](NC(=O)Nc1ccc(Br)cc1F)C(N)=O] | $^{1}$H NMR (acetone-d6, 300 MHz) δ: 8.28 (t, J = 8.9 Hz, 1H), 8.07 (br. s., NH), 7.33 (dd, J = 10.8, 2.3 Hz, 1H), 7.23-7.30 (m, 1H), 7.10 (br. s., NH), 6.50 (d, J = 8.2 Hz, NH), 6.38 (br. s., NH), 4.42 (ddd, J = 9.6, 8.3, 5.0 Hz, 1H), 1.70-1.87 (m, 1H), 1.59-1.70 (m, 1H), 1.44-1.59 (m, 1H), 0.95 (d, J = 1.5 Hz, 3H), 0.93 (d, 3H). |
| 16 | tert-butyl (2S)-2-{[(4-bromo-2-fluorophenyl) carbamoyl]amino}-4-methylpentanoate 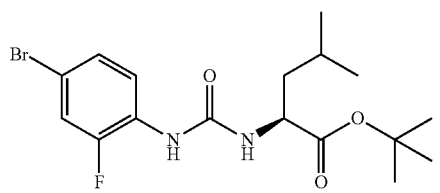 | $^{1}$H NMR (CDCl$_{3}$, 300 MHz) δ: 7.89 (t, J = 8.8 Hz, 1H), 7.14 (dd, J = 10.4, 2.2 Hz, 1H), 7.06 (d, J = 9.1 Hz, 1H), 6.80 (d, J = 2.6 Hz, NH), 5.79 (br. s., NH), 4.45 (dd, J = 8.8, 5.0 Hz, 1H), 1.69-1.85 (m, 1H), 1.57-1.69 (m, 1H), 1.52 (s, 9H), 1.41-1.48 (m, 1H), 0.97 (d, J = 3.5 Hz, 3H), 0.95 (d, 3H). |
| 17 | 2-{[(4-bromophenyl)carbamoyl]amino}-2,4-dimethylpentanoic acid 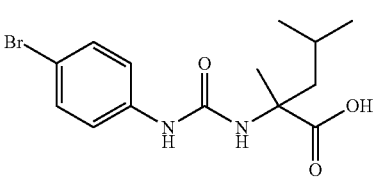 [SMILES: CC(C)CC(C)(NC(=O)Nc1ccc(Br)cc1)C(=O)O] | $^{1}$H NMR (CD$_{3}$OD, 300 MHz) δ: 7.31-7.39 (m, 2H), 7.22-7.30 (m, 2H), 1.80-1.92 (m, 2H), 1.71-1.82 (m, 1H), 1.56-1.67 (m, 2H), 1.44 (s, 3H), 0.98 (d, J = 1.2 Hz, 3H), 0.95 (d, J = 1.2 Hz, 3H). |
| 18 | tert-butyl {2-{[(4-bromophenyl)carbamoyl]amino}-2-methylpropanoate 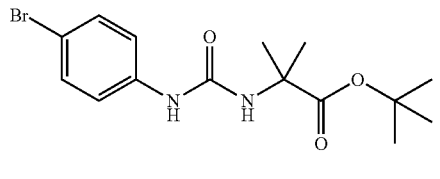 [SMILES: CC(C)(C)OC(=O)C(C)(C)NC(=O)Nc1ccc(Br)cc1] | $^{1}$H NMR (CD$_{3}$OD, 300 MHz) δ: 9.29 (br. s., NH), 8.58-8.75 (m, 4H), 7.33 (br. s., NH), 2.65-2.75 (m, 9H). |
| 19 | 2-{[(4-bromophenyl)carbamoyl]amino}-2-methylpropanoic acid 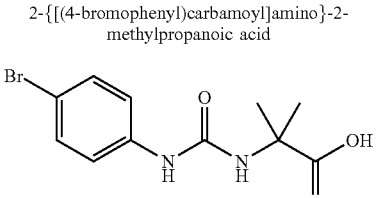 | 1H NMR (CD3OD, 300 MHz) δ: 7.32-7.37 (m, 2H), 7.24-7.29 (m, 2H), 1.52 (s, 6H). |

TABLE 4-continued

| | | |
|---|---|---|
| 20 | 2-{[(4-bromophenyl)carbamoyl]amino}-2-ethylbutanoic acid 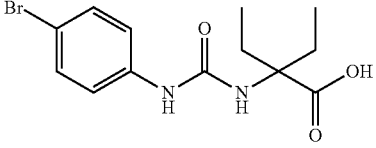 [SMILES: CCC(CC)(NC(=O)Nc1ccc(Br)cc1)C(=O)O] | $^1$H NMR (acetone-d6, 300 MHz) δ: 8.76 (br. s., 1H), 7.44-7.52 (m, 2H), 7.31-7.40 (m, 2H), 6.30 (br. s., 1H), 2.29-2.48 (m, 2H), 1.75-1.92 (m, 2H), 0.76-0.86 (m, 6H). |
| 21 | tert-butyl (2S)-4-methyl-2-({[4-(trifluoromethyl)phenyl]carbamoyl}amino)pentanoate 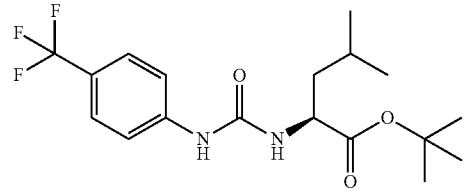 [SMILES: CC(C)C[C@H](NC(=O)Nc1ccc(C(F)(F)F)cc1)C(=O)OC(C)(C)C] | $^1$H NMR (CD$_3$OD, 300 MHz) δ: 7.50 (s, 4H), 4.27 (dd, J = 9.1, 5.6 Hz, 1H), 1.68-1.86 (m, 1H), 1.52-1.66 (m, 2H), 1.45-1.50 (s, 9H), 0.95 (t, J = 6.9 Hz, 6H). |
| 22 | (2S)-4-methyl-2-({[4-(trifluoromethyl)phenyl]carbamoyl}amino)pentanoic acid 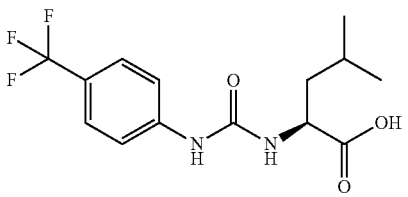 [SMILES: CC(C)C[C@H](NC(=O)Nc1ccc(C(F)(F)F)cc1)C(=O)O] | $^1$H NMR (CD$_3$OD, 300 MHz) δ: 7.49-7.57 (m, 4H), 4.38 (dd, J = 9.4, 5.0 Hz, 1H), 1.69-1.87 (m, 1H), 1.51-1.69 (m, 2H), 0.92-1.01 (m, 6H). |
| 23 | tert-butyl (2S)-2-({(4-chlorophenyl)carbamoyl}amino)4-methylpentanoate 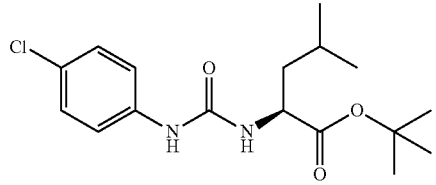 [SMILES: CC(C)C[C@H](NC(=O)Nc1ccc(Cl)cc1)C(=O)OC(C)(C)C] | $^1$H NMR (CD$_3$OD, 300 MHz) δ: 7.30-7.39 (m, 2H), 7.17-7.28 (m, 1H), 4.25 (dd, J = 8.9, 5.7 Hz, 1H), 1.74 (dd, J = 13.6, 7.5 Hz, 1H), 1.51-1.67 (m, 2H), 1.47 (s, 9H), 0.97 (t, J = 6.9 Hz, 6H). |
| 24 | (2S)-2-({(4-chlorophenyl)carbamoyl}amino)4-methylpentanoic acid 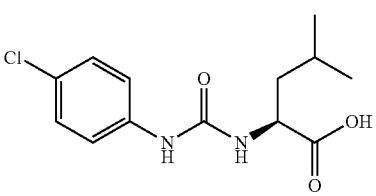 [SMILES: CC(C)C[C@H](NC(=O)Nc1ccc(Cl)cc1)C(=O)O] | $^1$H NMR (CD$_3$OD, 300 MHz) δ: 7.29-7.38 (m, 2H), 7.17-7.27 (m, 2H), 4.36 (dd, J = 9.4, 5.0 Hz, 1H), 1.73 (dd, J = 18.3, 5.7 Hz, 1H), 1.51-1.68 (m, 2H), 0.98 (dd, J = 6.4, 3.5 Hz, 6H). |
| 25 | tert-butyl (2S)-2-({(4-iodophenyl)carbamoyl}amino)4-methylpentanoate 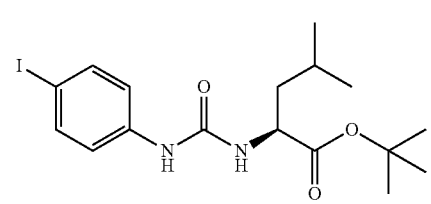 [SMILES: CC(C)C[C@H](NC(=O)Nc1ccc(I)cc1)C(=O)OC(C)(C)C] | $^1$H NMR (CD$_3$OD, 300 MHz) δ: 7.50-7.59 (m, 2H), 7.12-7.23 (m, 2H), 4.25 (m, 1H), 1.73 (m, 1H), 1.49-1.63 (m, 2H), 1.47 (s, 9H), 0.91-1.03 (m, 6H). |

TABLE 4-continued

| | | |
|---|---|---|
| 26 | (2S)-2-({(4-iodophenyl)carbamoyl}amino)4-methylpentanoic acid | ¹H NMR (CD₃OD, 300 MHz) δ: 7.50-7.58 (m, 2H), 7.13-7.21 (m, 2H), 4.35 (dd, J = 9.4, 5.0 Hz, 1H), 1.50-1.86 (m, 2H), 1.01 (m, 6H). |
| 27 | (2R,3R)-2-({(4-bromophenyl)carbamoyl}amino)3-methylpentanoic acid | ¹H NMR (CD₃OD, 300 MHz) δ: 7.35-7.39 (m, 2H), 7.28-7.32 (m, 2H), 4.32 (d, J = 4.7 Hz, 1H), 1.92 (dq, J = 6.8, 4.6 Hz, 1H), 1.46-1.60 (m, 1H), 1.16-1.33 (m, 1H), 0.93-1.02 (m, 6H). |
| 28 | tert-butyl (2R)-2-({(4-bromophenyl) carbamoyl}amino)4-methylpentanoate | ¹H NMR (CDCl₃, 300 MHz) δ: 7.33 (d, J = 8.5 Hz, 2H), 7.17 (s, 2H), 4.43 (dd, J = 9.1, 5.3 Hz, 1H), 1.68-1.79 (m, 1H), 1.56-1.67 (m, 1H), 1.48 (s, 9H), 1.44 (s, 1H), 0.97 (d, J = 4.1 Hz, 3H), 0.95 (d, J = 4.4 Hz, 3H). |
| 29 | (2R)-2-({(4-bromophenyl)carbamoyl}amino)4-methylpentanoic acid | ¹H NMR (acetone-D6, 300 MHz) δ: 8.17 (s, NH), 7.43-7.50 (m, 2H), 7.33-7.41 (m, 2H), 6.04 (d, J = 7.9 Hz, NH), 4.42-4.52 (m, 1H), 1.71-1.87 (m, 1H), 1.52-1.69 (m, 2H), 0.97 (d, J = 2.1 Hz, 3H), 0.95 (d, J = 2.3 Hz, 3H). |
| 30 | tert-butyl (2S)-4-methyl-2-({[4-(methylthio)phenyl]carbamoyl}amino)pentanoate | ¹H NMR (CD3OD, 300 MHz) δ: 7.27-7.32 (m, 2H), 7.18-7.23 (m, 2H), 4.22-4.29 (m, 1H), 2.42 (s, 3H), 1.70-1.79 (m, 1H), 1.51-1.61 (m, 2H), 1.47 (s, 9H), 0.97 (t, J = 6.7 Hz, 6H). |
| 31 | (2S)-4-methyl-2-({[4-(methylthio)phenyl]carbamoyl}amino)pentanoic acid | ¹H NMR (CD3OD, 300 MHz) δ: 7.25-7.31 (m, 2H), 7.14-7.20 (m, 2H), 4.37 (dd, J = 9.2, 5.1 Hz, 1H), 2.39 (s, 3H), 1.68-1.83 (m, 1H), 1.51-1.67 (m, 2H), 0.96 (dd, J = 6.2, 2.3 Hz, 6H). |

TABLE 4-continued

| | | |
|---|---|---|
| 32 | (2S)-4-methyl-2-{({4-[(trifluoromethyl)thio]phenyl}carbamoyl}amino)pentanoic acid | $^1$H NMR (CD3OD, 300 MHz) δ: 7.52-7.58 (m, 2H), 7.47-7.52 (m, 2H), 4.37 (dd, J = 9.4, 5.0 Hz, 1H), 1.70-1.82 (m, 1H), 1.53-1.69 (m, 2H), 0.99 (d, J = 3.2 Hz, 3H), 0.97 (d, J = 3.2 Hz, 3H). |
| 33 | tert-butyl (2S)-4-methyl-2-{({4-[(trifluoromethyl)thio]phenyl}carbamoyl}amino)pentanoate | $^1$H NMR (CD3OD, 300 MHz) δ: 7.53-7.57 (m, 2H), 7.47-7.51 (m, 2H), 4.26 (dd, J = 8.9, 5.7 Hz, 1H), 1.74 (td, J = 13.6, 6.7 Hz, 1H), 1.51-1.65 (m, 2H), 1.47 (s, 9H), 0.97 (t, J = 6.7 Hz, 6H). |
| 34 | (2S)-2-({(4-bromophenyl)carbamoyl}amino)4-(methylthio)butanoic acid | $^1$H NMR (CD$_3$OD, 300 MHz) δ: 7.23-7.41 (m, 4H), 4.31-4.42 (m, 1H), 2.56 (d, J = 15.5 Hz, 2H), 2.12-2.23 (m, 1H), 2.08 (s, 3H), 1.98 (dt, J = 14.0, 7.2 Hz, 1H). |
| 35 | 2-({(4-bromophenyl)carbamoyl}amino)3-(1H-imidazol-4-yl)propanoic acid | $^1$H NMR (CD$_3$OD, 300 MHz) δ: 8.76 (s, 1H), 7.23-7.40 (m, 6H), 4.65 (m, 1H), 3.03-3.27 (m, 2H). |

Biological Data

Biological activity of compounds according to Formula II is set forth in Table 5 below. CHO-Gα16 cells stably expressing FPRL-1 were cultured in (F12, 10% FBS, 1% PSA, 400 μg/ml geneticin and 50 μg/ml hygromycin) and HEK-Gqi5 cells stable expressing FPRL-1 were cultured in (DMEM high glucose, 10% FBS, 1% PSA, 400 μg/ml geneticin and 50 μg/ml hygromycin). In general, the day before the experiment, 18,000 cells/well were plated in a 384-well clear bottom poly-d-lysine coated plate. The following day the screening compound-induced calcium activity was assayed on the FLIPR$^{Tetra}$. The drug plates were prepared in 384-well microplates using the EP3 and the MultiPROBE robotic liquid handling systems. Compounds were tested at concentrations ranging from 0.61 to 10,000 nM. Results are expressed as EC$_{50}$ (nM) and efficacy values.

TABLE 5

| IUPAC Name Compound | FPRL-1 Gα16-CHO EC$_{50}$ (nM) (Rel. eff.) |
|---|---|
| {[2-{[(4-bromophenyl)carbamoyl]amino}-3-(1H-imidazol-4-yl)propanoyl]amino}acetic acid | 10.0 (0.95) |
| tert-butyl {[2-{[(4-bromophenyl)carbamoyl]amino}-3-(1H-imidazol-4-yl)propanoyl]amino}acetate | 263 (0.95) |
| {[(2S)-2-{[(4-bromophenyl)carbamoyl]amino}-4-(methylsulfonyl)butanoyl]amino}acetic acid | 247 (1.01) |
| tert-butyl {[(2S)-2-{[(4-bromophenyl)carbamoyl]amino}-4-(methylsulfonyl)butanoyl]amino}acetate | 1238 (0.97) |
| {[(2S)-2-{[(4-bromophenyl)carbamoyl]amino}-4-(methylsulfanyl)butanoyl]amino}acetic acid | 7 (1.03) |
| tert-butyl {[(2S)-2-{[(4-bromophenyl)carbamoyl]amino}-4-(methylsulfanyl)butanoyl]amino}acetate | 127 (0.98) |
| 2-methyl-2-{[(2S)-4-methyl-2-({[4-(trifluoromethyl)phenyl]carbamoyl}amino)pentanoyl]amino}propanoic acid | 2.3 (0.92) |

TABLE 5-continued

| IUPAC Name Compound | FPRL-1 Gal6-CHO EC$_{50}$ (nM) (Rel. eff.) |
|---|---|
| tert-butyl 2-methyl-2-{[(2S)-4-methyl-2-({[4-(trifluoromethyl)phenyl]carbamoyl}amino)pentanoyl]amino}propanoate | 1016 (1.07) |
| {[(2S)-4-methyl-2-({[4-(methylsulfonyl)phenyl]carbamoyl}amino)pentanoyl]amino}acetic acid | 459 (1.12) |
| tert-butyl {[(2S)-4-methyl-2-({[4-(methylsulfonyl)phenyl]carbamoyl}amino)pentanoyl]amino}acetate | 1083 (0.90) |
| {[(2S)-4-methyl-2-({[4-(methylsulfinyl)phenyl]carbamoyl}amino)pentanoyl]amino}acetic acid | 358 (1.21) |
| tert-butyl {[(2S)-4-methyl-2-({[4-(methylsulfinyl)phenyl]carbamoyl}amino)pentanoyl]amino}acetate | 668 (0.97) |
| 2-{[(2S)-2-({[[(4-bromophenyl)amino]carbamoyl}amino)-4-methylpentanoyl] amino}-2-methylpropanoic acid | 1 (0.96) |
| tert-butyl 2-{[(2S)-2-{[(4-bromophenyl)carbamoyl]amino}-4-methylpentanoyl]amino}-2-methylpropanoate | 133 (1.16) |
| ({(2S)-4-methyl-2-[({4-[(trifluoromethyl)sulfanyl]phenyl}carbamoyl)amino]pentanoyl}amino)acetic acid | 560 (1.07) |
| tert-butyl ({(2S)-4-methyl-2-[({4-[(trifluoromethyl)sulfanyl]phenyl}carbamoyl)amino]pentanoyl}amino)acetate | 3103 (0.78) |
| {[(2S)-4-methyl-2-({[4-(methylsulfanyl)phenyl]carbamoyl}amino)pentanoyl]amino}acetic acid | 2.95 (1.05) |
| tert-butyl {[(2S)-4-methyl-2-({[4-(methylsulfanyl)phenyl]carbamoyl}amino)pentanoyl]amino}acetate | 116 (0.98) |
| {[(2R)-2-{[(4-bromophenyl)carbamoyl]amino}-4-methylpentanoyl]amino}acetic acid | 1229 (0.97) |
| tert-butyl {[(2R)-2-{[(4-bromophenyl)carbamoyl]amino}-4-methylpentanoyl]amino}acetate | 3657 (0.92) |
| {[(2R,3R)-2-{[(4-bromophenyl)carbamoyl]amino}-3-methylpentanoyl]amino}acetic acid | 19315 (0.45) |
| tert-butyl {[(2R,3R)-2-{[(4-bromophenyl)carbamoyl]amino}-3-methylpentanoyl]amino}acetate | 3974 (0.44) |
| {[(2S)-4-methyl-2-({[4-(trifluoromethyl)phenyl]carbamoyl}amino)pentanoyl]amino}acetic acid | 1.8 (0.99) |
| tert-butyl {[(2S)-4-methyl-2-({[4-(trifluoromethyl)phenyl]carbamoyl}amino)pentanoyl]amino}acetate | 309 (0.81) |
| {[(2R)-2-{[(4-bromo-2-fluorophenyl)carbamoyl]amino}-4-methylpentanoyl]amino}acetic acid | 1489 (0.87) |
| (2S)-2-{[(4-bromophenyl)carbamoyl]amino}-N-[2-(dimethylamino)-2-oxoethyl]-4-methylpentanamide | 1.4 (0.90) |
| [(2-{[(4-bromophenyl)carbamoyl]amino}-2-methylpropanoyl)amino]acetic acid | 480 (0.99) |
| tert-butyl [(2-{[(4-bromophenyl)carbamoyl]amino}-2-methylpropanoyl)amino]acetate | 114 (1.02) |
| [(2-{[(4-bromophenyl)carbamoyl]amino}-2-ethylbutanoyl)amino]acetic acid | 19 (1.04) |
| tert-butyl [(2-{[(4-bromophenyl)carbamoyl]amino}-2-ethylbutanoyl)amino]acetate | 31 (1.03) |
| [(2-{[(4-bromophenyl)carbamoyl]amino}-2,4-dimethylpentanoyl)amino]acetic acid | 22 (0.98) |
| tert-butyl [(2-{[(4-bromophenyl)carbamoyl]amino}-2,4-dimethylpentanoyl)amino]acetate | 58 (0.98) |
| (2S)-N-[(1S)-2-amino-2-oxo-1-phenylethyl]-2-{[(4-bromophenyl)carbamoyl]amino}-4-methylpentanamide | 84 (0.99) |
| (2S)-{[(2S)-2-{[(4-bromophenyl)carbamoyl]amino}-4-methylpentanoyl]amino}(phenyl)ethanoic acid | 9.1 (1.08) |
| tert-butyl (2S)-{[(2S)-2-{[(4-bromophenyl)carbamoyl]amino}-4-methylpentanoyl]amino}(phenyl)ethanoate | 122 (1.02) |
| (2S)-N-[(2S)-1-amino-1-oxopentan-2-yl]-2-{[(4-bromophenyl)carbamoyl]amino}-4-methylpentanamide | 6.4 (1.03) |
| (2S)-2-{[(2S)-2-{[(4-bromophenyl)carbamoyl]amino}-4-methylpentanoyl]amino}pentanoic acid | 1.0 (0.89) |
| tert-butyl (2S)-2-{[(2S)-2-{[(4-bromophenyl)carbamoyl]amino}-4-methylpentanoyl]amino}pentanoate | 13 (1.06) |
| (2S)-2-{[(4-bromophenyl)carbamoyl]amino}-N-[(2R)-1-hydroxypropan-2-yl]-4-methylpentanamide | 3.0 (1.00) |
| (2S)-2-{[(4-bromophenyl)carbamoyl]amino}-N-(2,3-dihydroxypropyl)-4-methylpentanamide | 5.1 (0.98) |
| (2S)-2-{[(4-bromophenyl)carbamoyl]amino}-N-(1,3-dihydroxypropan-2-yl)-4-methylpentanamide | 7.4 (0.96) |
| (2S)-2-{[(4-bromophenyl)carbamoyl]amino}-N-(2-hydroxy-2-methylpropyl)-4-methylpentanamide | 2.1 (1.01) |
| (2S)-N-[(2S)-1-amino-3-methyl-1-oxobutan-2-yl]-2-{[(4-bromophenyl)carbamoyl]amino}-4-methylpentanamide | 1.3 (1.03) |
| (2S)-2-{[(2S)-2-{[(4-bromophenyl)carbamoyl]amino}-4-methylpentanoyl]amino}-3-methylbutanoic acid | 1.83 (1.13) |
| tert-butyl (2S)-2-{[(2S)-2-{[(4-bromophenyl)carbamoyl]amino}-4-methylpentanoyl]amino}-3-methylbutanoate | 68 (0.98) |
| (2S)-N-[(2S)-1-amino-1-oxopropan-2-yl]-2-{[(4-bromophenyl)carbamoyl]amino}-4-methylpentanamide | 24 (0.96) |
| (2S)-2-{[(2S)-2-{[(4-bromophenyl)carbamoyl]amino}-4-methylpentanoyl]amino}propanoic acid | 11 (1.05) |
| tert-butyl (2S)-2-{[(2S)-2-{[(4-bromophenyl)carbamoyl]amino}-4-methylpentanoyl]amino}propanoate | 147 (0.96) |
| (2S)-N-[(2S)-1-amino-1-oxopropan-2-yl]-2-{[(4-bromo-2-fluorophenyl)carbamoyl]amino}-4-methylpentanamide | 31 (1.05) |
| (2S)-2-{[(2S)-2-{[(4-bromo-2-fluorophenyl)carbamoyl]amino}-4-methylpentanoyl]amino}propanoic acid | 12 (0.95) |
| tert-butyl (2S)-2-{[(2S)-2-{[(4-bromo-2-fluorophenyl)carbamoyl]amino}-4-methylpentanoyl]amino}propanoate | 174 (1.00) |
| (2S)-2-{[(4-bromo-2-fluorophenyl)carbamoyl]amino}-N-(2-hydroxyethyl)-4-methylpentanamide | 77 (1.05) |
| (2S)-2-{[(4-bromo-2-fluorophenyl)carbamoyl]amino}-4-methyl-N-(2-oxopropyl)pentanamide | 20 (0.99) |
| (2S)-N-(2-amino-2-oxoethyl)-2-{[(4-bromo-2-fluorophenyl)carbamoyl]amino}-4-methylpentanamide | 4.5 (0.95) |
| {[(2S)-2-{[(4-bromo-2-fluorophenyl)carbamoyl]amino}-4-methylpentanoyl]amino}acetic acid | 3.6 (1.10) |
| tert-butyl {[(2S)-2-{[(4-bromo-2-fluorophenyl)carbamoyl]amino}-4-methylpentanoyl]amino}acetate | 134 (1.19) |
| (2S)-N-(2-amino-2-oxoethyl)-2-{[(4-bromo-2-fluorophenyl)carbamoyl]amino}pentanamide | 5.2 (0.98) |
| (2S)-N-(2-amino-2-oxoethyl)-2-{[(4-bromophenyl)carbamoyl]amino}pentanamide | 2.5 (0.97) |
| (2S)-2-{[(4-bromophenyl)carbamoyl]amino}-4-methyl-N-(2-oxopropyl)pentanamide | 4.7 (0.82) |
| (2S)-N-(2-amino-2-oxoethyl)-2-{[(4-bromophenyl)carbamoyl]amino}-4-methylpentanamide | 1.05 (1.08) |
| {[(2S)-2-{[(4-bromophenyl)carbamoyl]amino}-4-methylpentanoyl]amino}acetic acid | 0.88 (0.91) |
| (2S)-2-{[(4-bromophenyl)carbamoyl]amino}-N-(2-hydroxyethyl)-4-methylpentanamide | 11 (0.92) |
| tert-butyl {[(2S)-2-{[(4-bromophenyl)carbamoyl]amino}-4-methylpentanoyl]amino}acetate | 140 (0.85) |
| {[(2S)-2-{[(4-bromo-2-fluorophenyl)carbamoyl]amino}pentanoyl]amino}acetic acid | 4.8 (0.92) |
| tert-butyl {[(2S)-2-{[(4-bromo-2-fluorophenyl)carbamoyl]amino}pentanoyl]amino}acetate | 83 (0.95) |
| (2S)-2-{[(4-bromo-2-fluorophenyl)carbamoyl]amino}-N-(2-oxopropyl)pentanamide | 92 (0.92) |
| (2S)-2-{[(4-bromophenyl)carbamoyl]amino}-N-(2-oxopropyl)pentanamide | 35 (1.05) |
| propan-2-yl {[(2S)-2-{[(4-bromophenyl)carbamoyl]amino}pentanoyl]amino}acetate | 14 (1.04) |
| ethyl {[(2S)-2-{[(4-bromophenyl)carbamoyl]amino}pentanoyl]amino}acetate | 57 (1.18) |
| methyl {[(2S)-2-{[(4-bromophenyl)carbamoyl]amino}pentanoyl]amino}acetate | 17 (0.88) |
| (2S)-2-{[(4-bromo-2-fluorophenyl)carbamoyl]amino}-N-(2-hydroxyethyl)pentanamide | 105 (0.87) |
| (2S)-2-{[(4-bromophenyl)carbamoyl]amino}-N-(2- | 38 |

TABLE 5-continued

| IUPAC Name Compound | FPRL-1 Gα16-CHO EC$_{50}$ (nM) (Rel. eff.) |
|---|---|
| hydroxyethyl)pentanamide | (0.92) |
| (2S)-2-{[(4-bromo-2-fluorophenyl)carbamoyl]amino}-N-(2-hydroxyethyl)-3-phenylpropanamide | 16 (0.98) |
| {[(2S)-2-{[(4-bromophenyl)carbamoyl]amino}pentanoyl]amino}acetic acid | 3.2 (0.91) |
| tert-butyl {[(2S)-2-{[(4-bromophenyl)carbamoyl]amino}pentanoyl]amino}acetate | 31 (0.95) |
| (2S)-2-{[(4-bromo-2-fluorophenyl)carbamoyl]amino}-N-(2-oxopropyl)-3-phenylpropanamide | 12 (0.94) |
| (2S)-2-{[(4-bromophenyl)carbamoyl]amino}-N-(2-oxopropyl)-3-phenylpropanamide | 29 (0.96) |
| (2S,3S)-2-{[(4-bromo-2-fluorophenyl)carbamoyl]amino}-N-(2-hydroxyethyl)-3-methylpentanamide | 62 (1.00) |
| (2S,3S)-2-{[(4-bromophenyl)carbamoyl]amino}-N-(2-hydroxyethyl)-3-methylpentanamide | 24 (1.00) |
| (2S,3S)-2-{[(4-bromo-2-fluorophenyl)carbamoyl]amino}-3-methyl-N-(2-oxopropyl)pentanamide | 36 (1.01) |
| (2S,3S)-2-{[(4-bromophenyl)carbamoyl]amino}-3-methyl-N-(2-oxopropyl)pentanamide | 10 (0.97) |
| (2S,3S)-N-(2-amino-2-oxoethyl)-2-{[(4-bromo-2-fluorophenyl)carbamoyl]amino}-3-methylpentanamide | 10 (1.00) |
| (2S,3S)-N-(2-amino-2-oxoethyl)-2-{[(4-bromophenyl)carbamoyl]amino}-3-methylpentanamide | 4.6 (0.81) |
| {[(2S,3S)-2-{[(4-bromophenyl)carbamoyl]amino}-3-methylpentanoyl]amino}acetic acid | 2.7 (1.00) |
| tert-butyl {[(2S,3S)-2-{[(4-bromophenyl)carbamoyl]amino}-3-methylpentanoyl]amino}acetate | 280 (0.85) |
| {[(2S,3S)-2-{[(4-bromo-2-fluorophenyl)carbamoyl]amino}-3-methylpentanoyl]amino}acetic acid | 5.5 (0.95) |
| tert-butyl {[(2S,3S)-2-{[(4-bromo-2-fluorophenyl)carbamoyl]amino}-3-methylpentanoyl]amino}acetate | 757 (0.86) |
| (2S)-2-{[(4-bromophenyl)carbamoyl]amino}-N-(2-hydroxyethyl)-3-phenylpropanamide | 6 (0.92) |
| 3-{[(2S)-2-{[(4-bromophenyl)carbamoyl]amino}-3-phenylpropanoyl]amino}propanoic acid | 18 (0.98) |
| tert-butyl 3-{[(2S)-2-{[(4-bromophenyl)carbamoyl]amino}-3-phenylpropanoyl]amino}propanoate | 255 (1.00) |
| {[(2S)-2-{[(4-bromophenyl)carbamoyl]amino}-3-phenylpropanoyl]amino}acetic acid | 7.7 (0.99) |
| tert-butyl {[(2S)-2-{[(4-bromophenyl)carbamoyl]amino}-3-phenylpropanoyl]amino}acetate | 118 (0.91) |
| tert-butyl 2-{[(2R)-2-{[(4-bromophenyl)carbamoyl]amino}-4-methylpentanoyl]amino}-2-methylpropanoate | 2725 (0.74) |
| 2-{[(2R)-2-{[(4-bromophenyl)carbamoyl]amino}-4-methylpentanoyl]amino}-2-methylpropanoic acid | 490 (0.74) |
| {[2-{[(4-bromophenyl)carbamoyl]amino}-3-(1H-indol-3-yl)propanoyl]amino}acetic acid | 0.73 (0.97) |
| tert-butyl {[2-{[(4-bromophenyl)carbamoyl]amino}-3-(1H-indol-3-yl)propanoyl]amino}acetate | 305 (1.03) |
| [(4-amino-2-{[(4-bromophenyl)carbamoyl]amino}-4-oxobutanoyl)amino]acetic acid | 2938 (0.81) |
| tert-butyl [(4-amino-2-{[(4-bromophenyl)carbamoyl]amino}-4-oxobutanoyl)amino]acetate | 2306 (0.90) |

What is claimed is:

1. A method of treating rheumatoid arthritis in a subject in need of such treatment, the method comprising administering to the subject a therapeutically effective amount of a compound of Formula II:

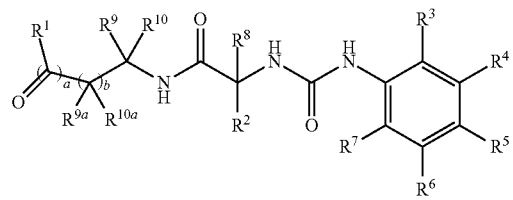

Formula II wherein:

a is 1 and b is 0;

$R^1$ is optionally substituted $C_{1-8}$ alkyl, optionally substituted $C_{3-8}$ cycloalkyl, optionally substituted heterocycle, optionally substituted $C_{6-10}$ aryl, optionally substituted $C_{3-8}$ cycloalkenyl, —$NR^{11}R^{12}$ or —$OR^{13}$;

$R^2$ is optionally substituted $C_{1-8}$ alkyl or optionally substituted $C_{6-10}$ aryl;

$R^3$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;

$R^4$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;

$R^5$ is halogen;

$R^6$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;

$R^7$ is hydrogen, optionally substituted $C_{1-8}$ alkyl, halogen, —$COOR^{15}$, —$OR^{13}$, —$NR^{11}R^{12}$, $NO_2$, optionally substituted heterocycle, optionally substituted $C_{3-8}$ cycloalkyl, optionally substituted $C_{6-10}$ aryl or optionally substituted $C_{3-8}$ cycloalkenyl;

$R^8$ is hydrogen, optionally substituted $C_{1-8}$ alkyl or optionally substituted $C_{6-10}$ aryl;

$R^9$ is hydrogen;

$R^{10}$ is hydrogen;

$R^{11}$ is hydrogen or optionally substituted $C_{1-8}$ alkyl, provided that $R^{11}$ is not

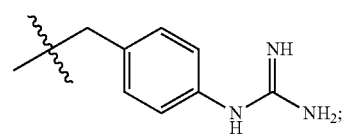 [SMILES: *Cc1ccc(NC(=N)N)cc1]

$R^{12}$ is hydrogen;

$R^{13}$ is hydrogen or optionally substituted $C_{1-8}$ alkyl; and $R^{15}$ is hydrogen or optionally substituted $C_{1-8}$ alkyl;

or an enantiomer, diastereomer, tautomer, hydrate or solvate thereof;

or a pharmaceutically acceptable salt of the foregoing;

provided that the compound is not:

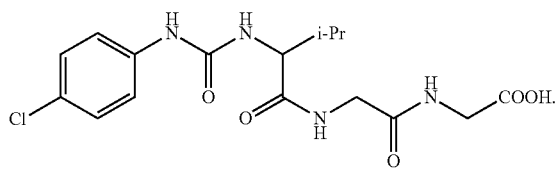 [SMILES: CC(C)C(NC(=O)Nc1ccc(Cl)cc1)C(=O)NCC(=O)NCC(=O)O]

2. The method of claim 1, wherein:
   $R^1$ is optionally substituted $C_{1-8}$ alkyl, —$NR^{11}R^{12}$ or —$OR^{13}$;
   $R^2$ is optionally substituted $C_{1-8}$ alkyl;
   $R^3$ is hydrogen, optionally substituted $C_{1-8}$ alkyl, halogen, —$COOR^{15}$, —$OR^{13}$ or —$NR^{11}R^{12}$;
   $R^4$ is hydrogen, optionally substituted $C_{1-8}$ alkyl, halogen, —$COOR^{15}$, —$OR^{13}$ or —$NR^{11}R^{12}$;
   $R^6$ is hydrogen, optionally substituted $C_{1-8}$ alkyl, halogen, —$COOR^{15}$, —$OR^{13}$ or —$NR^{11}R^{12}$;
   $R^7$ is hydrogen, optionally substituted $C_{1-8}$ alkyl, halogen, —$COOR^{15}$, —$OR^{13}$ or —$NR^{11}R^{12}$; and
   $R^8$ is hydrogen or optionally substituted $C_{1-8}$ alkyl.

3. The method of claim 2, wherein:
   $R^1$ is —$OR^{13}$;
   $R^2$ is unsubstituted $C_{1-8}$ alkyl;
   $R^3$ is hydrogen;
   $R^4$ is hydrogen;
   $R^6$ is hydrogen;
   $R^7$ is hydrogen; and
   $R^8$ is hydrogen.

4. The method of claim 1, wherein the compound is selected from:

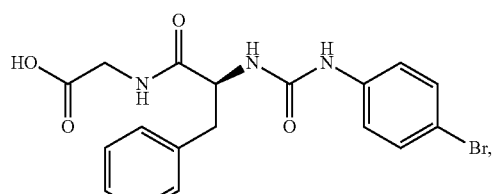

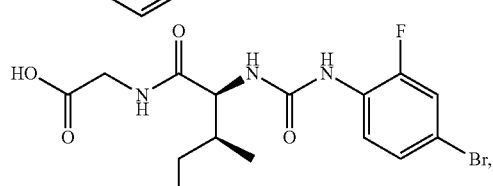

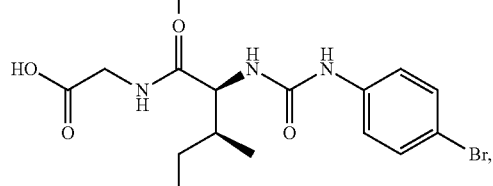

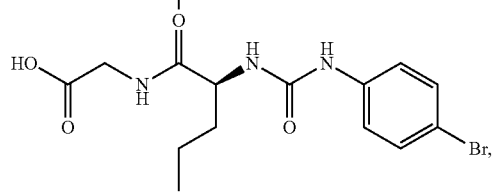

-continued

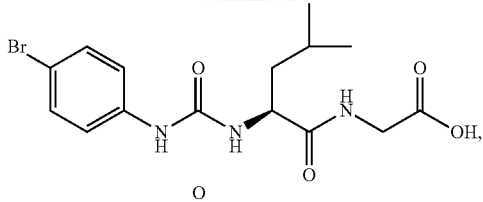

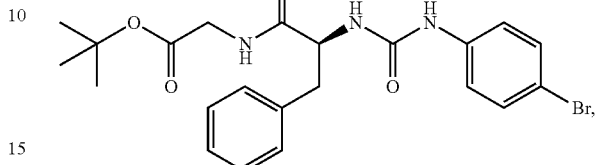

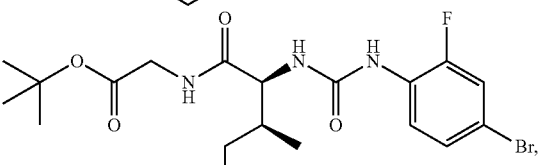

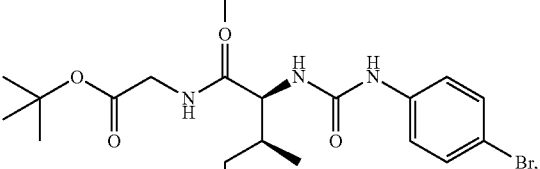

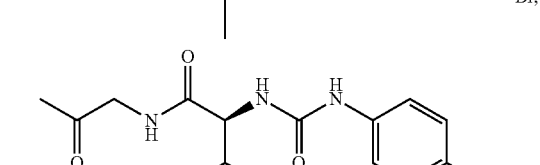

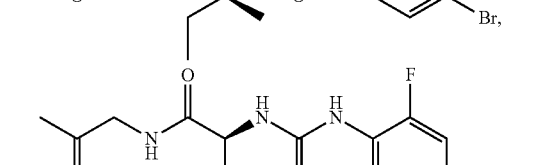

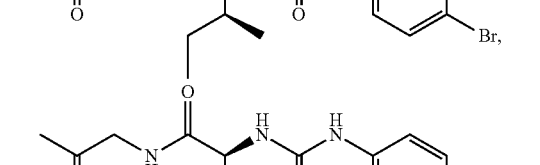

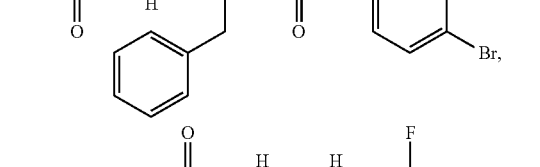

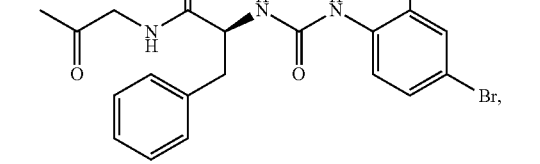

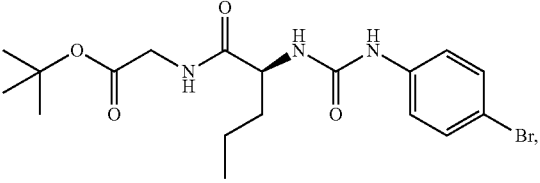

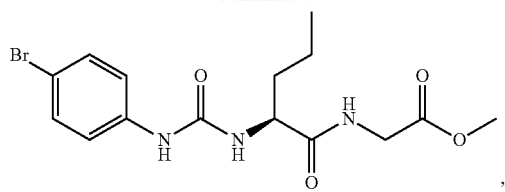
,
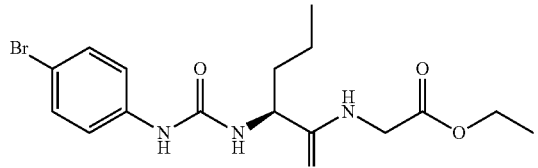
,
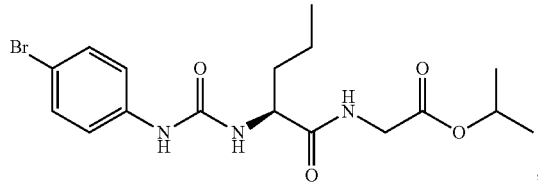
,
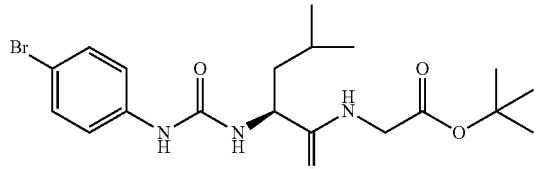
,
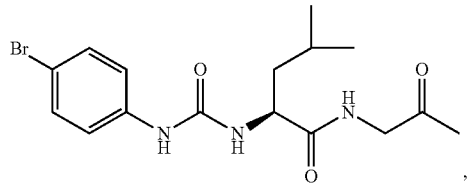
,
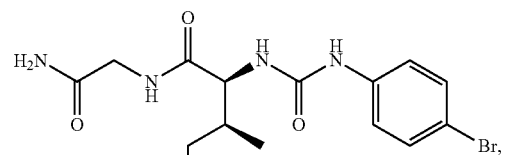
,
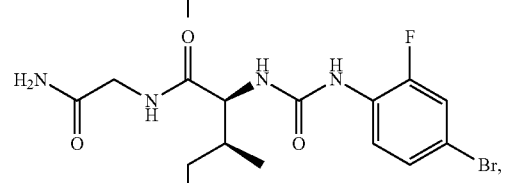
,
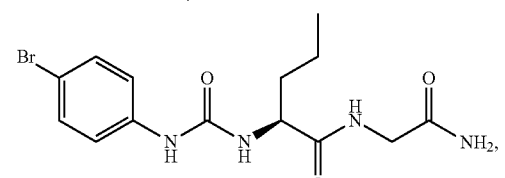
,
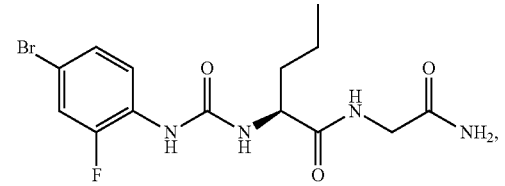
,
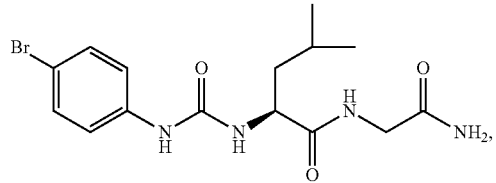
,
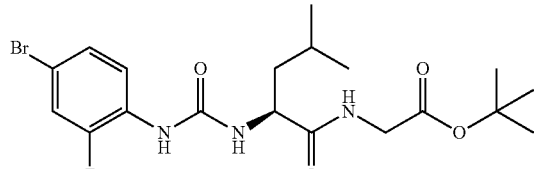
,
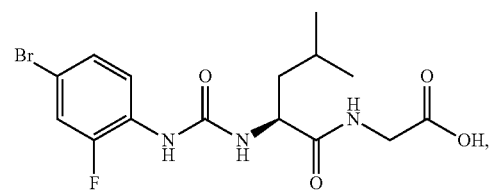
,
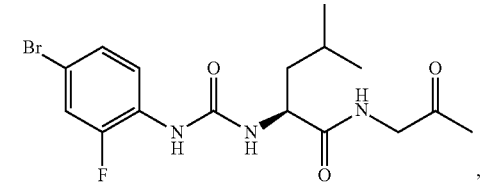
,
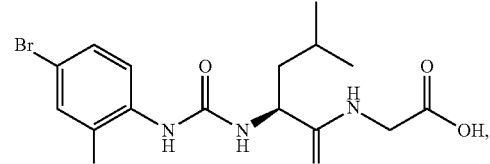
,
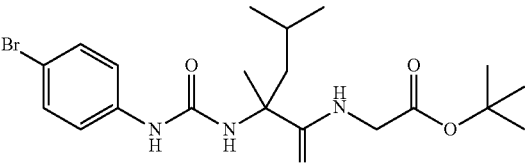
,
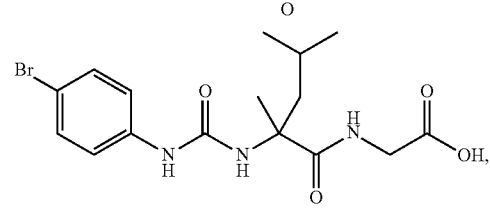
,
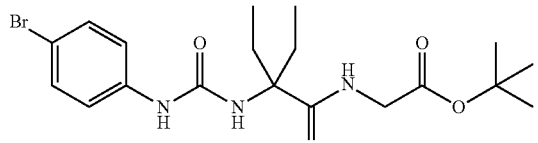
,
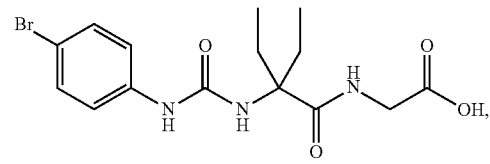
, -continued
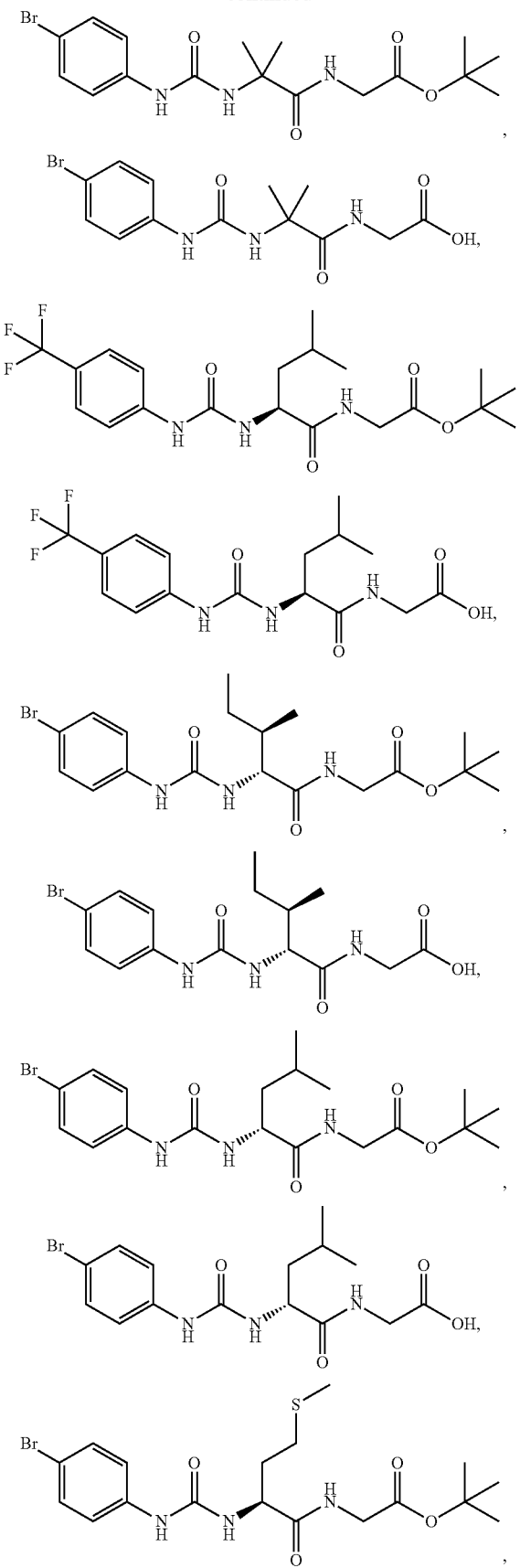
-continued
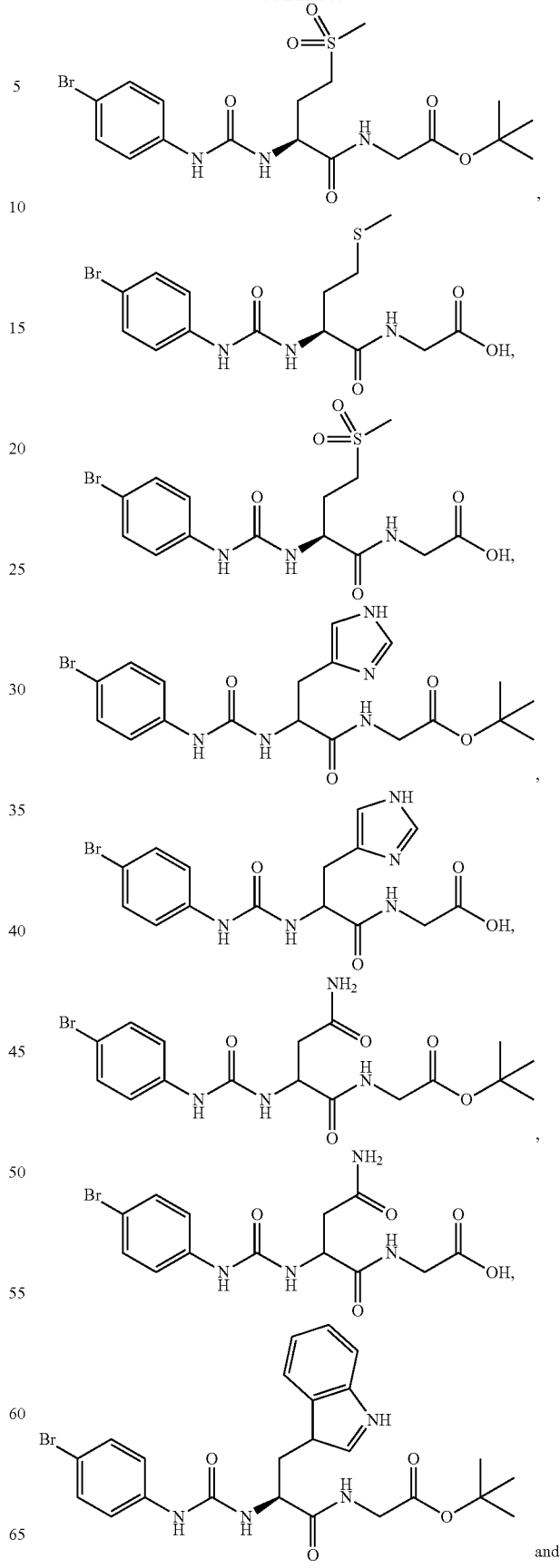
and

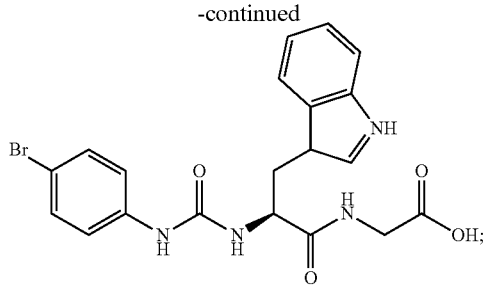

and enantiomers, diastereoisomers, tautomers, hydrates and solvates thereof;
and pharmaceutically acceptable salts of the foregoing.

5. A method of treating rheumatoid arthritis in a subject in need of such treatment, the method comprising administering to the subject a therapeutically effective amount of a compound having the following structure:

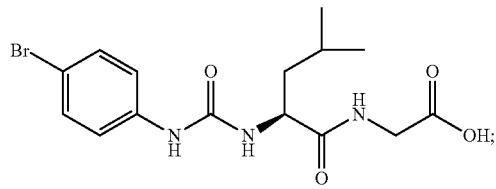

or a pharmaceutically acceptable salt thereof.

6. The method of claim 1, 4 or 5, wherein the subject is a human.

* * * * *

UNITED STATES PATENT AND TRADEMARK OFFICE
CERTIFICATE OF CORRECTION

PATENT NO. : 9,974,772 B2  
APPLICATION NO. : 15/408643  
DATED : May 22, 2018  
INVENTOR(S) : Richard L. Beard et al.

It is certified that error appears in the above-identified patent and that said Letters Patent is hereby corrected as shown below:

On the Title Page

Column 1, in (Notice), Line 3, after "0 days." delete "days.".

In the Specification

In Column 6, Line 52, delete "$R^{19}$" and insert -- $R^{10}$ --, therefor.

In Column 7, Line 1, delete "$R^{1}$" and insert -- $R^{11}$ --, therefor.

In Column 13, Line 1, delete "$S(O)_nR^{14}$;" and insert -- —$S(O)_nR^{14}$; --, therefor.

In Column 18, Line 64, delete "—$COOR^{15}$—$OR^{13}$," and insert -- —$COOR^{15}$, —$OR^{13}$, --, therefor.

In Column 21, Line 2, below "and" insert -- $R^{11}$ is not: --.

In Column 21, Line 52, delete "-$NR^{11}R^{12}$, $NO_2$," and insert -- -$NR^{11}R^{12}$; --, therefor.

In Column 25 (Structure), Lines 1-6, after " 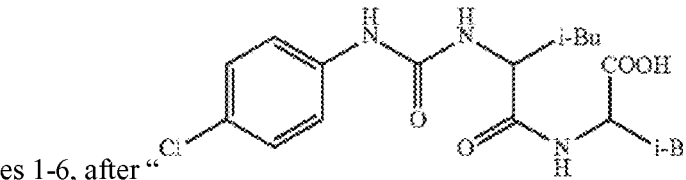 " delete ";".

In Column 25, Line 25, after " 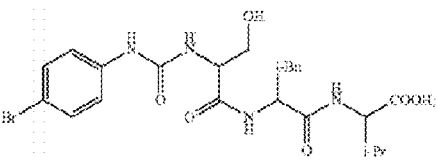 " insert -- or --.

Signed and Sealed this  
Seventeenth Day of July, 2018

Andrei Iancu  
*Director of the United States Patent and Trademark Office*

CERTIFICATE OF CORRECTION (continued)
U.S. Pat. No. 9,974,772 B2

In Column 31, Line 40, delete "-S(O)$_N$R$^{14}$;" and insert -- -S(O)$_n$R$^{14}$; --, therefor.

In Column 31, Line 48, delete "R$^{10A}$" and insert -- R$^{10a}$ --, therefor.

In Columns 57-58, Line 1 (Comp. No. 18), delete "$^1$$^H$ NMR" and insert -- $^1$H NMR --, therefor.

In Columns 57-58, Line 2 (Comp. No. 20), delete "pentanamid" and insert -- pentanamide --, therefor.

In Columns 59-60, Line 1 (Comp. No. 26), delete "(CD$_3$ OD," and insert -- (CD$_3$OD, --, therefor.

In Columns 61-62, Line 1 (Interm. No. 9), delete "δ(ppm)" and insert -- δ (ppm) --, therefor.

In Columns 61-62, Line 4 (Interm. No. 9), delete "0H)," and insert -- OH), --, therefor.

In Columns 67-68, Line 1 (Comp. No. 46), delete "3methyl" and insert -- 3-methyl --, therefor.

In Columns 73-74, Line 4 (Comp. No. 57), delete "(dq," and insert -- (d, --, therefor.

In Columns 77-78, Lines 1-2 (Comp. No. 71), delete "}c arbamoyl)" and
insert -- }carbamoyl) --, therefor.

In Columns 81-82, Line 4 (Comp. No. 82), delete "(m.," and insert -- (m, --, therefor.

In Columns 81-82, Line 1 (Comp. No. 85), delete "(DMSO-D$_6$," and insert -- (DMSO-d$_6$, --, therefor.

In Columns 81-82, Line 4 (Comp. No. 85), delete "(m.," and insert -- (m, --, therefor.

In Columns 81-82, Line 5 (Comp. No. 85), delete "(m.," and insert -- (m, --, therefor.

In Columns 83-84, Line 2 (Comp. No. 87), delete "2NH)," and insert -- 2H), --, therefor.

In Columns 83-84, Line 4 (Comp. No. 87), delete "(m" and insert -- (m, --, therefor.

In Columns 91-92, Line 3 (Interm. No. 27), delete "(dq," and insert -- (d, --, therefor.

In Columns 91-92, Line 1 (Interm. No. 28), delete "(CDCl $_3$," and insert -- (CDCl$_3$, --, therefor.

In Columns 91-92, Line 1 (Interm. No. 29), delete "(acetone-D6," and insert -- (acetone-d6, --, therefor.

In Column 93, Line 3 (Structure) (Interm. No. 34), delete " 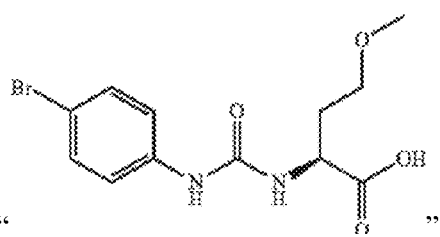 "
and insert -- 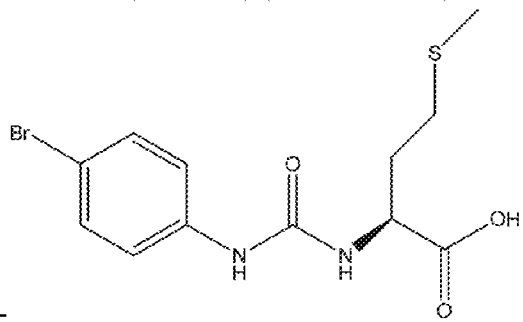 --, therefor.